(12) United States Patent
Lee

(10) Patent No.: US 10,729,354 B2
(45) Date of Patent: Aug. 4, 2020

(54) SYSTEM AND METHOD FOR MODELING BRAIN DYNAMICS IN NORMAL AND DISEASED STATES

(71) Applicant: THE REGENTS OF THE UNIVERSITY OF CALIFORNIA, Oakland, CA (US)

(72) Inventor: Jin Hyung Lee, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1114 days.

(21) Appl. No.: 14/765,144

(22) PCT Filed: Jan. 31, 2014

(86) PCT No.: PCT/US2014/014318
§ 371 (c)(1),
(2) Date: Jul. 31, 2015

(87) PCT Pub. No.: WO2014/121146
PCT Pub. Date: Aug. 7, 2014

(65) Prior Publication Data
US 2015/0366482 A1 Dec. 24, 2015

Related U.S. Application Data

(60) Provisional application No. 61/759,363, filed on Jan. 31, 2013.

(51) Int. Cl.
*A61B 5/05* (2006.01)
*A61B 5/0484* (2006.01)
(Continued)

(52) U.S. Cl.
CPC .......... *A61B 5/0484* (2013.01); *A61B 5/0476* (2013.01); *A61B 5/04842* (2013.01);
(Continued)

(58) Field of Classification Search
CPC ...................................................... A61B 5/00
See application file for complete search history.

(56) References Cited

U.S. PATENT DOCUMENTS

2004/0092809 A1* 5/2004 DeCharms ......... G01R 33/4806
600/410
2009/0088680 A1 4/2009 Aravanis et al.
(Continued)

FOREIGN PATENT DOCUMENTS

| JP | 2010-057899 A | 3/2010 |
| JP | 2011-509697 A | 3/2011 |
| WO | WO 2008/106694 A2 | 9/2008 |
| WO | WO 2011/116238 A2 | 9/2011 |
| WO | WO2012/061744 A2 | 5/2012 |

OTHER PUBLICATIONS

Ranjbar et al (Automatic focal seizures suppression system: An application of optogenetic gene silencing.*
(Continued)

*Primary Examiner* — Joel F Brutus
(74) *Attorney, Agent, or Firm* — Morgan, Lewis & Bockius LLP

(57) ABSTRACT

A system and method is provided for modeling brain dynamics in normal and diseased states.

18 Claims, 35 Drawing Sheets

(51) Int. Cl.
| | |
|---|---|
| G16H 50/50 | (2018.01) |
| A61B 5/0476 | (2006.01) |
| A61B 5/055 | (2006.01) |
| A61B 5/00 | (2006.01) |
| G06F 19/00 | (2018.01) |
| A61N 1/36 | (2006.01) |
| G01R 33/561 | (2006.01) |

(52) U.S. Cl.
CPC ............ *A61B 5/055* (2013.01); *A61B 5/4064* (2013.01); *A61B 5/4094* (2013.01); *A61N 1/3606* (2013.01); *A61N 1/36053* (2013.01); *G01R 33/5616* (2013.01); *G06F 19/3481* (2013.01); *G16H 50/50* (2018.01); *A61B 5/4848* (2013.01); *A61B 5/7278* (2013.01); *A61B 5/7285* (2013.01); *A61B 2576/026* (2013.01)

(56) References Cited

U.S. PATENT DOCUMENTS

| | | | | |
|---|---|---|---|---|
| 2009/0093403 | A1* | 4/2009 | Zhang | A01K 67/0333 514/8.1 |
| 2010/0160240 | A1* | 6/2010 | Gurd | A61K 38/1787 514/1.1 |
| 2011/0105998 | A1 | 5/2011 | Zhang et al. | |
| 2012/0083700 | A1* | 4/2012 | Osorio | A61B 5/0245 600/483 |
| 2012/0155904 | A1 | 6/2012 | Kawaguchi et al. | |
| 2012/0165904 | A1 | 6/2012 | Lee et al. | |
| 2012/0179029 | A1 | 7/2012 | Kircher et al. | |
| 2012/0271151 | A1 | 10/2012 | Lavoilette et al. | |

OTHER PUBLICATIONS

Communication Pursuant to Rules 161(2) and 162, EP14745909.3, dated Sep. 29, 2015, 2 pgs.
The Regents of the University of California, International Search Report and Written Opinion, PCT/US2014/014318, dated May 20, 2014, 9 pgs.
The Regents of the University of California, International Preliminary Report on Patentability, PCT/US2014/014318, dated Aug. 4, 2015, 6 pgs.
Lee, Jin Hyung, "Tracing Activity Across the Whole Brain Neural Network with Optogenetic Functional Magnetic Resonance Imaging," Oct. 25, 2011, Frontiers in Neuroinformatics, vol. 5, Article 21, 7 pgs.
Lee, Jin Hyung et al., "Global and Local FMRI Signals Driven by Neurons Defined Optogenetically by Type and Wiring," Jun. 10, 2010, Nature, vol. 465, 5 pgs.
Lee, Jin Hyung, et al., "Informing Brain Connectivity with Optogenetic Functional Magnetic Resonanace Imaging," Feb. 3, 2012, Neuroimage, vol. 62, 6 pgs.
Tye, Kay M. et al., "Optogenetic Investigation of Neural Circuits Underlying Brain Disease in Animal Models," Apr. 2012, Nature Reviews Neuroscience, vol. 13, 16 pgs.
The Regents of the University of California, Extended European Search Report, EP14745909.3, dated Oct. 31, 2016, 10 pgs.
The Regents of the University of California, Communication Pursuant to Rule 70(2) and 70a(2), EP14745909.3, dated Nov. 17, 2016, 1 pg.
The Regents of the University of California, Communication Pursuant to Article 94(3), EP14745909.3, dated Feb. 14, 2018, 6 pgs.
The Regents of the University of California, 1st Office Action, CN201480019606.8, dated May 24, 2017, 6 pgs.
The Regents of the University of California, 2nd Office Action, CN201480019606.8, dated Feb. 7, 2018, 7 pgs.
The Regents of the University of California, 3rd Office Action, CN201480019606.8, dated Sep. 3, 2018, 6 pgs.
The Regents of the University of California, 4th Office Action, CN201480019606.8, dated Feb. 2, 2019, 2 pgs.
The Regents of the University of California, 5th Office Action, CN 201480019606.8, dated Jun. 3, 2019, 9 pgs.
The Regents of the University of California, Office Action, JP2015-556189, dated Nov. 2, 2017, 6 pgs.
The Regents of the University of California, Office Action, Decision of Rejection, CN201480019606.8, dated Aug. 19, 2019, 10 pgs.

* cited by examiner

FIG. 4
a) TON-RST, pixel p<0.001, cluster p<0.05
b) VNS-RST, pixel p<0.001, cluster p<0.05
 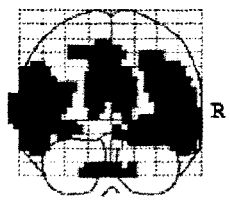 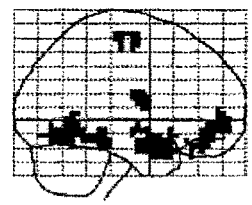 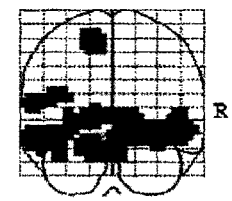
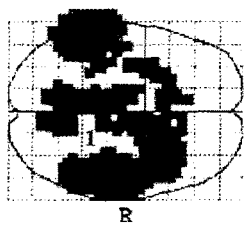
1. Noise
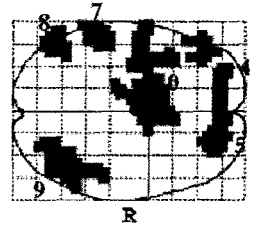
4. L. orbitofrontal
5. R. orbitofrontal
7. L. temporal
8. L. parieto-
   occipital
9. R. parieto-
   occipital

FIG. 12
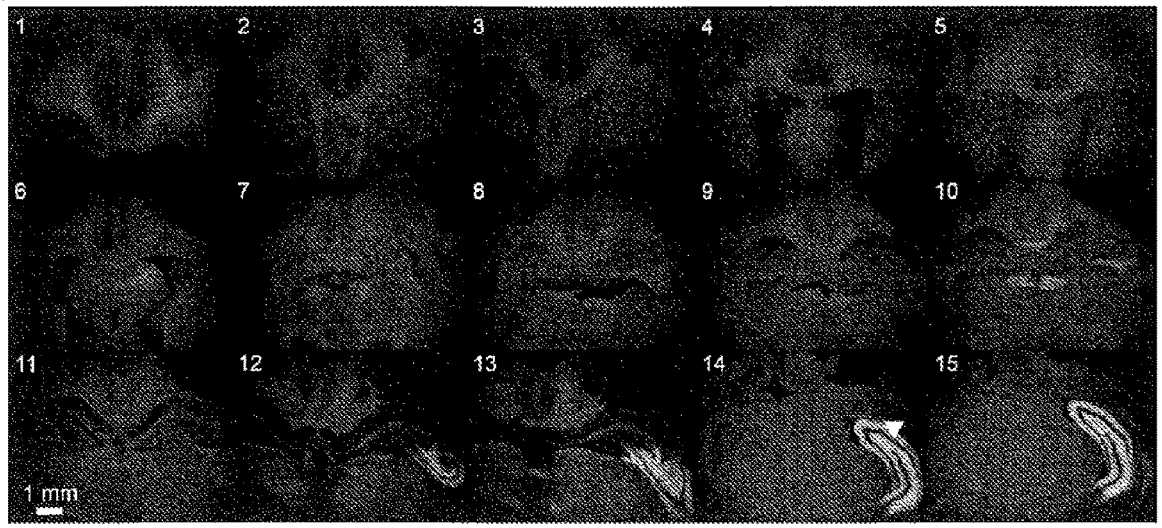
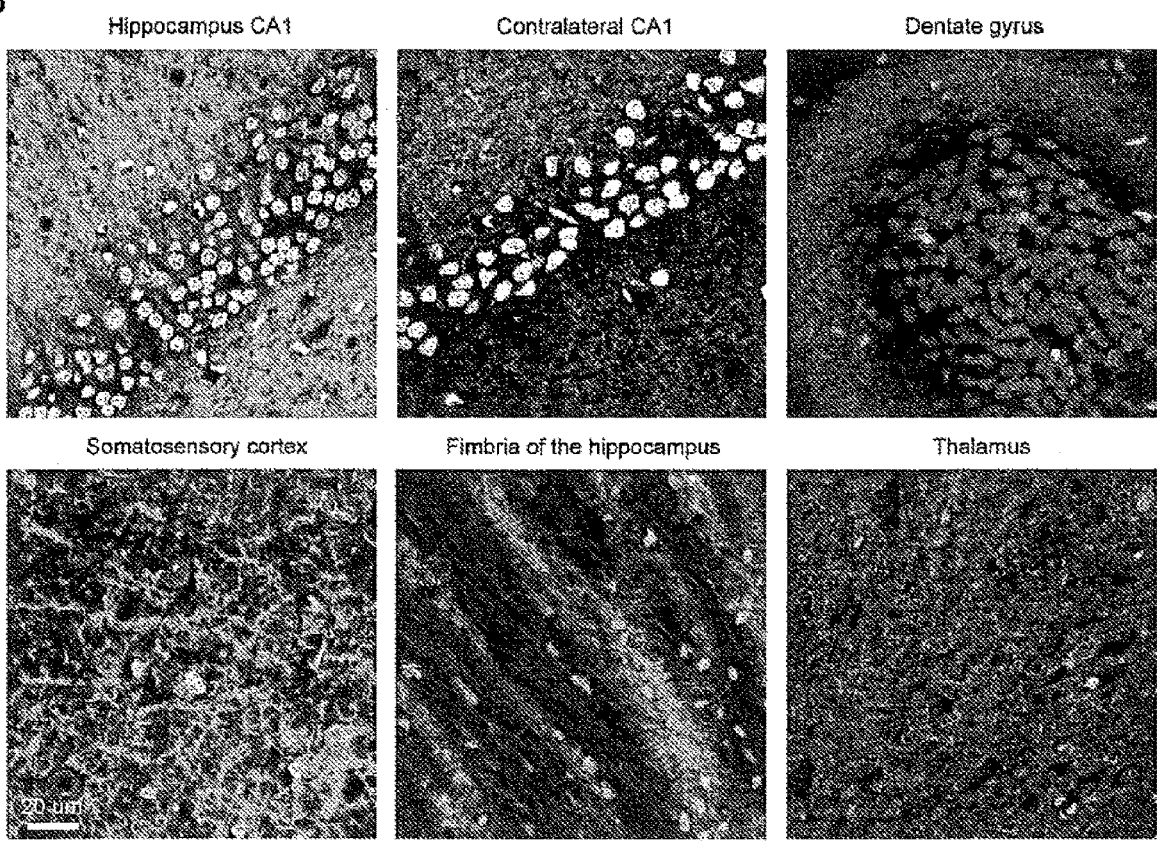

Bicuculline 0.1 mM, 2 μL into left hippocampus via cannula in a rat. LH = left hippocampus, LP = left posterior bone screw, RA = right anterior bone screw.

FIG. 23
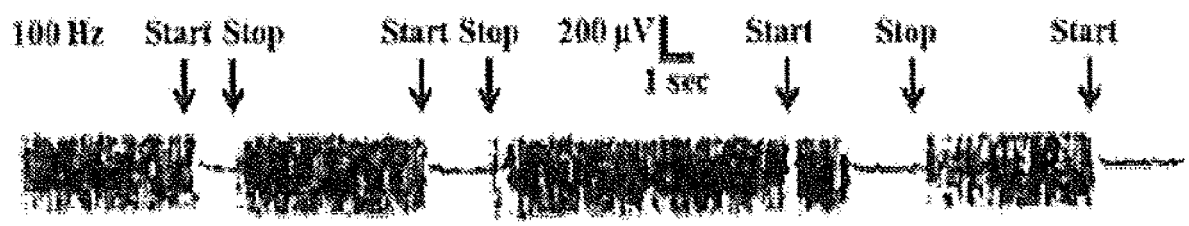
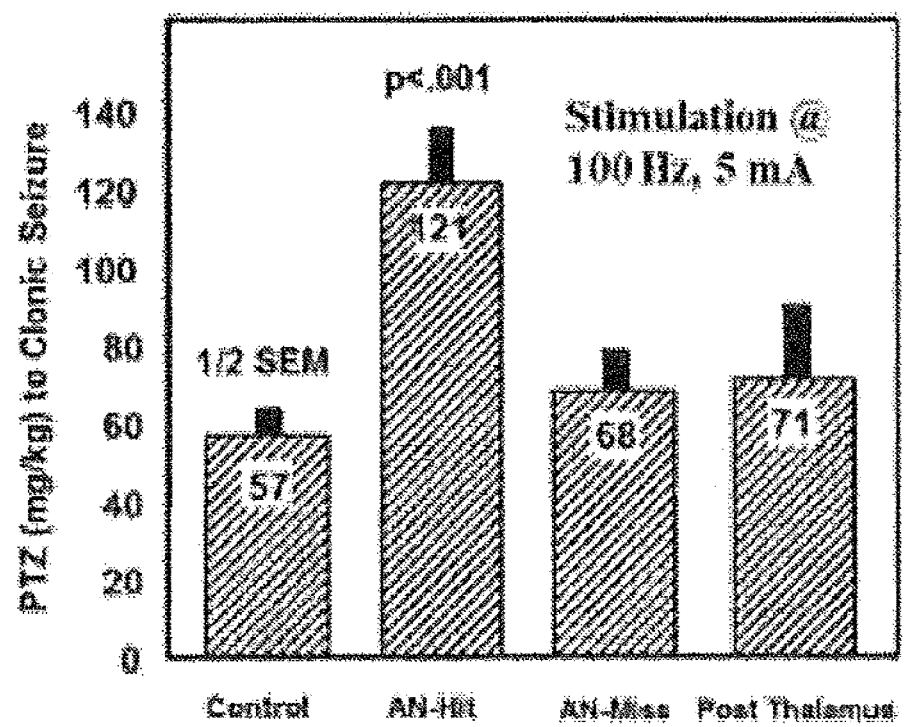

FIG. 25

|       | Year 1 | Year 2 | Year 3 | Year 4 | Year 5 |
|-------|--------|--------|--------|--------|--------|
| Aim 1 | Opto.Seizure Model Gen. and Validation in Rats | Opto.Seizure Model Gen. and Validation in Mice | | | |
| Aim 2 | | Inhibit Seizures: Pyramidal Inhib. in Rats | Inhibit Seizures: Pyramidal Excit. in Rats | Inhibit Seizures: Serotonergic Cholinergic Trig. in mice | |
| Aim 3 | | | Electrical ANT. Stim. in Rats | Emulate Optimal Opto. Stim with Electrical Stim. in Rats | Study Optimal Timing of Elec. Stim |

SYSTEM AND METHOD FOR MODELING BRAIN DYNAMICS IN NORMAL AND DISEASED STATES

CROSS-REFERENCES TO RELATED APPLICATIONS

This application is a United States National Stage Application filed under 35 U.S.C. 371 of PCT Patent Application Ser. No. PCT/US2014/014318 filed Jan. 31, 2014, which claims priority to U.S. Provisional Patent Application No. 61/759,363 filed Jan. 31, 2013, entitled MODELING THE BRAIN DYNAMICS IN NORMAL AND DISEASED STATES, the entire contents of which is incorporated herein for all purposes by this reference.

STATEMENT REGARDING FEDERALLY SPONSORED RESEARCH OR DEVELOPMENT

This invention was made with Government support under Grant No. EB008738 awarded by the National Institutes of Health. The Government has certain rights in the invention.

BACKGROUND OF INVENTION

Field of Invention

The present invention relates, in general, to systems and methods for modeling brain dynamics and more particularly to modeling brain dynamics in normal and diseased states.

Description of Related Art

Brain network function dynamics for normal and neurologically diseased states are mostly unknown. The present invention provides for a new methodology designed to create a disease model with high-precision knowledge of the associated brain network function dynamics and to longitudinally probe the brain function network dynamics enabling quantitative design and evaluate therapeutic options. Using this approach, therapeutics can be designed and evaluated to directly aim at altering specific brain dynamics. For example, this approach can benefit developments of drugs, neurostimulation, focal surgery, cell, and gene therapy.

Conventional animal models to study neurological diseases are generated using mechanical injury, drug delivery, electrical stimulation, and genetic alterations. The animal models are then characterized by behavioral assays, electrical recordings, anatomical evaluation, and ex vivo immunohistochemistry. The approach of the present invention is beneficial and overcomes various disadvantages of conventional modeling.

BRIEF SUMMARY

The proposed invention creates a unique, first opportunity to create, define, and categorize neurological disorders based on its precise, cell-type specific brain function. Furthermore, they can be monitored longitudinally with precision while therapeutics is administered to evaluate efficacy. In addition to evaluation, it also enables active design of therapeutics to alter the diseased brain function.

Optogenetic stimulation and functional magnetic resonance imaging readout may be used to identify ways to create animal models with precise origin and corresponding brain network dynamics. Models related to seizures and other diseased states may be created.

Various aspects of the proposed invention may be used as a pre-clinical method to guide human therapy development.

Various aspects of the present invention have been used to study and identify seizure models with precise origin and associated network, Alzheimer's disease network, Parkinson's disease addiction network, minimally conscious patient related DBS target network and other normal and diseased states.

Various aspects of the present invention are directed to a method for modeling brain dynamics in normal and diseased states includes creating a diseased state model in a brain, and categorizing the model based on optogenetic stimulation and functional magnetic resonance imaging (fMRI) imaging.

The method may further include making further measurements to interpret electroencephalography (EEG) measurement based on the categorizing during light responsive stimulation.

The further measurements may be made using EEG.

The diseased state model may be a model of a seizure.

The diseased state mode may be an animal model of a seizure.

The seizure may be generated from by at least one of dorsal CA1 stimulation, intermediate CA1 stimulation, ventral CA1 stimulation or subiculum stimulation.

The method may further include using the animal model of the seizure for neurostimulation and drug design.

Various aspects of the present invention provide for a method for modeling brain dynamics in normal and diseased states that includes identifying vagus nerve stimulation (VNS) mechanism of action through optogenetic functional magnetic resonance imaging (ofMRI) with cell-type specificity, generating distinct seizure types and evaluate efficacy of VNS for each seizure type to identify which seizure types, and identifying unique electroencephalography (EEG) signatures for each seizure type, and identifying an EEG signature in a patient by EEG and seizure synchronized ofMRI.

The method may further include conducting VNS-synchronized ofMRI to confirm VNS mechanisms of action.

Various aspects of the present invention provide for a method for modeling brain dynamics in normal and diseased states including creating a diseased state model in a brain, and categorizing the model based on optogenetic stimulation and functional magnetic resonance imaging (fMRI) imaging.

The method may further include making further measurements to interpret electroencephalography (EEG) measurement based on the categorizing during light responsive stimulation.

The further measurements may be made using EEG.

The diseased state model may be a model of a seizure.

The diseased state mode may be an animal model of a seizure.

The seizure may be generated from by at least one of dorsal CA1 stimulation, intermediate CA1 stimulation, ventral CA1 stimulation or subiculum stimulation.

The method may further include using the animal model of the seizure for neurostimulation and drug design.

Various aspects of the present invention provide for a method for modeling brain dynamics in normal and diseased states, the method including identifying neurostimulation mechanism of action through optogenetic functional magnetic resonance imaging (ofMRI) with cell-type specificity, generating distinct seizure types and evaluate efficacy of neurostimulation for each seizure type to identify which seizure types, and identifying unique electroencephalography (EEG) signatures for each seizure type, and identifying an EEG signature in a patient by EEG and seizure synchronized ofMRI.

The method may further include neurostimulation may be one of vagus nerve stimulation (VNS), deep brain stimulation (DBS), and responsive neurostimulation (RNS).

The method may further include conducting neurostimulation-synchronized ofMRI to confirm neurostimulation mechanisms of action.

The neurostimulation may be one of vagus nerve stimulation (VNS), deep brain stimulation (DBS), and responsive neurostimulation (RNS).

Various aspects of the present invention provide for a method for modeling brain dynamics in normal and diseased states, the method including optogenetically stimulating pyramidal neurons in dorso-medial, medial, ventro-medial and/or lateral CA1 regions, monitoring the seizure through linked brain networks with optogenetic functional magnetic resonance imaging (ofMRI), measuring local field potentials and single unit recordings at the location of ofMRI activity.

The step of optogenetically stimulating may be accomplished without incurring direct stimulation of inhibitory interneurons or fibers of passage.

The step of optogenetically stimulating may be accomplished utilizing frequency stimulation of below 20 Hz to generate short lasting activity.

The step of optogenetically stimulating may be accomplished utilizing frequency stimulation of 6-10 Hz to generate short lasting activity.

The step of optogenetically stimulating may be accomplished with frequency stimulation above 20 Hz.

The step of optogenetically stimulating may be accomplished utilizing frequency stimulation of 20-60 Hz to generate long lasting activity.

The step of optogenetically stimulating may be accomplished with 40 Hz light stimulation.

The method may further include injecting at least one of AAV5-CamKIIa-ChR2-EYFP or AAV5-CamKIIa-NpHR-mCherry to stimulate or inhibit pyramidal neurons, and applying at least one of blue and yellow light to optogenetically trigger the neurons.

Blue light may be delivered in 1, 10, 60, or 100 cycles per second.

Blue light may be delivered in 1, 10, 60, or 100 cycles per second for 20 seconds every minute for a total of six minutes while scanning the brain.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 3a illustrates an anterior thalamus (AV) is not engaged in a same seizure type of FIG. 2, while FIG. 3b illustrates clear involvement observed originating from excitatory neurons in subiculum.

FIG. 4a and FIG. 4b illustrate VNS synchronized fMRI.

FIG. 5, FIG. 5b, FIG. 5c, FIG. 5d, FIG. 5e, FIG. 5f and FIG. 5g illustrate optogenetic theta frequency excitation of pyramidal dorsal CA1 cells drives robust BOLD and EEG responses. FIG. 5a illustrates transduced cells (triangles), light and location of coronal slices (1 . . . 20). FIG. 5b illustrates fluorescent (left) and confocal (right) images of ChR2-EYFP expression in dorsal CA1. The arrows point to cells that show EYFP expression. FIG. 5c illustrates skull EEG and optical stimulation locations, in which the reference electrode is placed 3.0 mm anterior and 2.0 mm to the right of bregma and the recording electrode is placed on top of the cerebral cortex above dorsal CA1. FIG. 5d illustrates a diamond-shaped chamber with three cameras was custom designed to record behavior with detailed view of subtle facial and body movements. FIG. 5e illustrates evoked EEG spikes shown in concert with 6 Hz optical stimulation. FIG. 5f illustrates BOLD activation is observed predominantly in ipsilateral dorsal hippocampal formation (HF), ipsilateral thalamus (T), and ipsilateral retrosplenial cortex (RSC) (P<0.001; lower tip of triangle: optical stimulation site). The ofMRI dataset is averaged from six independent experiments in five animals. Each individual experiment consists of six fMRI scans. FIG. 5g illustrates, on the left, 750 ms temporal resolution sliding window reconstructed ofMRI hemodynamic response (averaged across all active voxels) is shown in response to each blue light stimulation, and on the right, a single epoch trace that shows BOLD signal peaks within the optical stimulation with significant decay after the stimulation stops.

FIG. 6, FIG. 6b and FIG. 6c illustrate Gamma frequency excitation of pyramidal dorsal CA1 cells generates evolving electrographic seizures with bilateral recruitment. FIG. 6a illustrates an evolving EEG seizure pattern that is shown when dorsal CA1 undergoes 40 Hz optical stimulation. Evoked spikes convert to higher voltage polyspike-slow waves. Ictal activity outlasts the stimulation. FIG. 6b illustrates, compared to 6 Hz stimulation of dorsal CA1, that 40 Hz stimulation incurs more extensive BOLD activation at bilateral dorsal hippocampal formation, bilateral thalamus, ipsilateral retrosplenial cortex, and the septum (P<0.001; triangle bottom tip: optical stimulation site). FIG. 6c, on the left, illustrates that 40 Hz dorsal CA1 stimulation evokes a prolonged BOLD HRF that is synchronized with the blue optical stimulation, and on the right, that single epoch HRF shows the sustained activation in ofMRI, which is consistent with the EEG result that ictal activity outlasts the 40 Hz light stimulation.

FIG. 7, FIG. 7b, FIG. 7c and FIG. 7d illustrate theta frequency excitation of pyramidal ventral CA1 cells gives robust BOLD and EEG responses. FIG. 7a illustrates transduced cells (triangles), light and location of ofMRI coronal slices (1 . . . 20). FIG. 7b illustrates fluorescent (left) and confocal (right) images of ChR2-EYFP expression in ventral CA1. The arrows point to cells that show EYFP expression. FIG. 7c illustrates that 6 Hz ventral hippocampus stimulation leads to evoked EEG spike-waves synchronous with stimulation. FIG. 7d illustrates that BOLD signal is observed in ipsilateral more than contralateral hippocampal formation, ipsilateral more than contralateral thalamus, bilateral lateral septal nuclei and ipsilateral retrosplenial cortex (P<0.001; lower tip of triangle: optical stimulation site). The ofMRI dataset is averaged from six independent experiments in four animals. Each individual experiment consists of six fMRI scans.

FIG. 8 and FIG. 8b illustrate gamma frequency excitation of pyramidal ventral CA1 cells generates EEG and behavioral seizure with extensive BOLD signal. FIG. 8a illustrates that 20 s, 40 Hz stimulation resulted in an evolving EEG seizure pattern outlasting the stimuli. Behaviors, including wet dog shakes, face twitching, clonic seizures and running jumping are robustly seen in different rodent subjects. FIG. 8b illustrates, compared to 6 Hz stimulation, that extensive BOLD activation is observed in different regions: ventral hippocampal formation, thalamus and septal region show more sustained responses while dorsal hippocampus and cingulate cortex show shorter lasting responses.

FIG. 10a is a fluorescent image that shows AAV5-CaMKII::hChR2-eYFP expression in dorsal hippocampal CA1, contralateral CA1, motor cortex, fimbria of the hippocampus, septal nucleus and thalamus. FIG. 10b is a confocal image that shows AAV5-CaMKII::hChR2-eYFP that is expressed in cell bodies located near the site of virus injection (dorsal hippocampus CA1 region, upper row left panel) and throughout axonal fibers projecting from those cell bodies. A small portion of cell bodies in contralateral dorsal hippocampus CA1 region and motor cortex layer VI is observed adjacent to the injection site expressing eYFP (<2%). However, since none of these regions directly project to the site of stimulation, fiber expression of ChR2 from neurons with cell body in these locations is not expected, which therefore doesn't interfere with a goal of directly stimulating only neurons with cell body in CA1. The eYFP expression is limited to axons in fimbria of the hippocampus, septal nucleus and thalamus.

FIG. 11a: 6 Hz and 10 Hz stimulation at dorsal hippocampus produced evoked spikes that did not outlast the stimulus. In contrast, stimulation at 20, 40 and 60 Hz produced evolving hippocampal ictal electrographic events and normal behavior in six experiments (ten experiments, two animals). The numbers inside circles indicate stimulation frequency. FIG. 11b: 6 Hz stimulation at ventral hippocampus produces three episodes of spike-waves during stimulation and one evolving seizure. 6 Hz ventral experiments correlated one each with normal behavior, two with wet dog shakes and one with a clonic seizure. In contrast, stimulation at 10, 20, 40, 60 Hz always result in a full evolving ictal pattern and seizure behaviors, including wet dog shakes, face twitching, clonic seizures, or a running jumping seizure (twenty one experiments, three animals). The replicability of the seizure pattern was evaluated by delivering three 20-second trains of light stimulation at 5, 10 and 15 minutes after the start of each experiment. The EEG and behavior patterns were similar for each of the three consecutive stimulations (only the most prolonged electrographic seizure was scored for data summary, usually the first). Duration of the EEG changes for the first seizure was 80.8±44.1 seconds, of the second seizure 40.9±34.3 seconds and of the third seizure 66.0±56.9 seconds. The first seizure had longer duration than did the second (p=0.00002, two-tailed paired t-test), but not the third (p=0.21). The mean duration of dorsal hippocampal seizures was 64.7±42.2 sec versus 86.9±44.0 sec for ventral seizures (p=0.08). Because ofMRI was recorded in rats anesthetized with inhalation of $O_2$ (35%), $N_2O$ (63.5%) and isoflurane (~1.2-1.5%), additional video-EEG was analyzed in thirty experiments in three animals inhaling the same mixture. Baseline EEGs before light stimulation all showed burst suppression as is expected from anesthesia, while light stimulation at 6, 10, 20, 40 and 60 Hz evoked electrographic evolving seizures, indistinguishable in duration and pattern from an EEG event in an awake rat.

FIG. 12a and FIG. 12b illustrate fluorescent and confocal images that show AAV5-CaMKII::hChR2-eYFP that is expressed in ventral hippocampal CA1 and connected regions. FIG. 12a: Fluorescent image shows AAV5-CaMKII::hChR2-eYFP is expressed in ventral hippocampal CA1, contralateral CA1, dentate gyrus, somatosensory cortex, fimbria of the hippocampus and thalamus. FIG. 12b: AAV5-CaMKII::hChR2-eYFP is expressed in cell bodies located near the site of virus injection (ventral hippocampus CA1, upper row left panel) and throughout axonal fibers projecting from those cell bodies, except a few cell bodies in somatosensory cortex layer VI adjacent to the injection site expressed eYFP (<1%). However, somatosensory cortex neurons do not directly project to the site of stimulation, we do not expect any fiber expression of ChR2 from neurons with cell body in somatosensory cortex, which therefore doesn't interfere with the goal of directly stimulating only neurons with cell body in CA1. The eYFP expression is limited to axons in contralateral hippocampus CA1, dentate gyrus, fimbria of the hippocampus, and thalamus.

FIG. 14, FIG. 14b, FIG. 14c, FIG. 14d and FIG. 14e illustrate ofMRI: optically-driven local excitation in defined rodent neocortical cells drives positive BOLD. FIG. 14a is a schematic of transduced cells (triangles) and blue light delivery shown in M1 at cannula implantation and stimulation site. Coronal imaging slices marked as "1 . . . 9". FIG. 14b shows confocal images of ChR2-EYFP expression in M1 (left); higher magnification reveals transduced neuronal cell bodies and processes (right). FIG. 14c shows extracellular optrode recordings during 473 nm optical stimulation. FIG. 14d, BOLD activation is observed at near the site of optical stimulation (arrowhead: injection/stimulation site). Coronal slices are consecutive and 0.5 mm thick. FIG. 14e shows ofMRI hemodynamic response during 6 consecutive epochs of optical stimulation (left); stimulus paradigm was 20 s of 20 Hz/15 ms 473 nm light stimulation repeated every 60 s (blue bars); Hemodynamic response was averaged across all voxels with coherence coefficient >0.35 in motor cortex: and mean of all stimulation epochs (right); baseline corresponds to mean pre-stimulation signal magnitude.

FIG. 16, FIG. 16b, FIG. 16c and FIG. 16d illustrate control of cells defined by location, genetic identity, and wiring during ofMRI. FIG. 16a shows M1 injection of MV5-CaMKIIa::ChR2-EYFP and optical stimulation of thalamus. Coronal slices shown in FIG. 16c marked as "1 . . . 6" and "7 . . . 12". FIG. 16b shows ChR2 expression pattern confirming expression in cortical neurons (left) and cortico-thalamic projections. FIG. 16c shows BOLD ofMRI data obtained in thalamus (above) and cortex (below). FIG. 16d shows ofMRI-HRF for cortical (gray) and thalamic (black) BOLD signals elicited by optical stimulation of cortico-thalamic fibers in thalamus. Both ofMRI-HRFs ramp slowly by comparison with intracortical results in FIG. 13.

FIG. 18a shows that serotonergic terminal staining is prominent in anteroventral thalamus FIG. 18b shows that cholinergic markers are especially dense in the posterior portions of anteroventral thalamus

FIG. 20, FIG. 20b, FIG. 20c, FIG. 20d, FIG. 20e and FIG. 20f illustrate ofMRI with pyramidal neuron stimulation in the hippocampus that evokes frequency-dependent, cell-type-specific activity. FIG. 20a shows 20 s, 10 Hz stimulation of medial CA1 pyramidal neurons elicit recruitment of temporal lobe regions both rostral and caudal to the injection site. FIG. 20b shows 20 Hz stimulation that yields enhanced rostral, caudal, and bilateral propagation of the induced activity. Number of active voxels for FIG. 20c shows 10 Hz and FIG. 20d shows 20 Hz were plotted for active anatomical regions. 20 Hz stimulation result in larger activation volume and phase. Subiculum has a particularly large phase difference. FIG. 20e shows ofMRI-HRF at the subiculum plotted for stimulation frequency of 6, 10, 20, 40, 60 Hz. Higher than 20 Hz stimulation gives sustained response for ~20 s after stimulation offset. FIG. 20f shows ofMRI-HRF at subiculum for 5, 10, 20 s of 20 Hz stimulation. Regardless of stimulation duration, they all give ~20 s sustained response after stimulation offset.

FIG. 21, FIG. 21b, FIG. 21c, FIG. 21d, FIG. 21e and FIG. 21f illustrate LFP and single unit recording show frequency dependence matching ofMRI results. FIG. 21a shows 20 s, 10 Hz stimulation of medial CA1 pyramidal neurons that results in LFP increase during optical stimulation. FIG. 21b shows, in contrast, 20 Hz stimulation that gives sustained LFP that lasts after stimulation offset. FIG. 21c shows single unit recording during 10 Hz stimulation that shows spike rate increase during stimulation. FIG. 21d shows 20 Hz and e, 60 Hz stimulation that results in sustained neural spiking after stimulation offset. FIG. 21f, interestingly, contra-lateral side recording in CA1 with 40 Hz stimulation shows a cell with inhibition upon stimulation which is sustained after stimulation offset.

FIG. 22a shows 20 s, 60 Hz stimulation of lateral CA1 pyramidal neurons that elicit recruitment of temporal lobe regions as well as other circuit elements in the circuit of Papez. FIG. 22b illustrates the number of active voxels in each region that is plotted. The phase shows larger diversity compared to medial CA1 stimulation.

FIG. 23a and FIG. 23b illustrate electrical stimulation of ANT in the PTZ model of seizures. FIG. 23a: 100 Hz stimulation of ANT stops cortical seizure activity. FIG. 23b: ANT stimulation is shown to increase the amount of PTZ necessary to produce clonic seizures.

FIG. 24a: Conventionally acquired and reconstructed passband b-SSFP fMRI. FIG. 24b: Undersampled high-resolution acquisition with compressed sensing reconstructed passband b-SSFP fMRI achieves 6 times smaller voxel volume with the same acquisition time.

FIG. 25 illustrates an exemplary research timeline.

FIG. 26a ofMRI-HRF at the subiculum with 20 s stimulation of dorso-medial CA1 pyramidal neurons at 6, 10, 20, 40, 60 Hz. Higher than 20 Hz stimulation gives sustained response for ~20 s after stimulation offset. b, ofMRI-HRF at subiculum for 5, 10, 20 s of 20 Hz stimulation. Regardless of stimulation duration, ~20 s sustained response is observed after stimulation offset. FIG. 26c and FIG. 26d show that 20 s, 6 and 10 Hz stimulation result in LFP increase during optical stimulation. FIG. 26e and FIG. 26f, show, in contrast, 20 and 40 Hz stimulation gives sustained LFP that lasts after stimulation offset. FIG. 26g illustrates single unit recording during 10 Hz stimulation that shows spike rate increase during stimulation. h, 40 Hz and i, 60 Hz stimulation results in sustained neural spiking after stimulation offset. FIG. 26j illustrates, contra-lateral side recording in CA1 with 40 Hz stimulation shows a cell with inhibition upon stimulation which is sustained after stimulation offset. These findings demonstrate the accuracy of ofMRI-HRF signal in representing temporal neural activity patterns.

FIG. 28a shows that 20 s, 40 Hz stimulation of medial CA1 pyramidal neurons elicit larger recruitment of temporal lobe regions both rostral and caudal to the injection site (blue star, +2.0 mm, −4.8 mm, −3.5 mm). upper left corner: Paxino's atlas slice number. FIG. 28b shows the number of active voxels that were plotted for active anatomical regions (5 animals). Behavior test shows a modified Racine scale of A and EEG score of 3.

FIG. 29a shows that 20 s, 40 Hz stimulation of ventro-lateral CA1 pyramidal neurons elicit distinct recruitment of the classical circuit of Papez (injection site: blue star, +5.4 mm, −6.6 mm, −4.2 mm). FIG. 29b shows the number of active voxels that were plotted for active anatomical regions (5 animals). Behavior test shows a modified Racine scale of 5

FIG. 30a is a photomicrograph of APP immunolabeling for dystrophic neurites (left) and Thioflavin S staining for amyloid plaques (right) in hippocampus of APPL/S mice given vehicle or LM11A-31 as indicated. Scale bars=25 µm. FIG. 30b is a photomicrograph of choline acetyltransferase-immunostained basal forebrain sections. Treatment of APPL/S mice with LM11A-31 was associated with increased length, volume, and branching of cholinergic neurites. FIG. 30c shows that LM11A-31 normalizes LTP in APP/PS1 mice: APP/PS1-vehicle vs. wt-vehicle, p=0.003; APP/PS1-vehicle vs. APP/PS1-LM11A-31, p=0.02; wt-vehicle vs. wt-LM11A-31, NS. FIG. 30d shows LM11A-31 prevented object recognition deficits in APPL/S mice. Statistical significance was determined using ANOVA and post-hoc Student-Neuman-Keuls testing.

FIG. 32a illustrates cholinergic neurons in the basal forebrain MSDBB that were selectively targeted for stimulation. FIG. 32b is an anatomical MRI image showing location of cannula implantation near imaging slice 2 in FIG. 32c. FIG. 32c is a gamma (40 Hz) frequency stimulation of cholinergic neurons in MSDBB that leads to a large area recruitment including the hippocampus. Active regions include M2 (supplementary motor cortex), Cg (cingulated cortex), septal nuclei, VHC (ventral hippocampal commissure), HF (hippocampal formation), and RSC (retrosplenial cortex). Grayscale represents phase, i.e. duration, peak timing of activity. White inverted triangle points to stimulation location.

FIG. 34a illustrates M1 injection of AAV5-CaMKIIa::ChR2-EYFP and optical stimulation of thalamus. Coronal slices are marked as "1 . . . 6" and "7 . . . 12". FIG. 34b illustrates BOLD ofMRI data obtained in thalamus (above) and cortex (below). This study demonstrates that ofMRI with stimulation of axonal fibers expressing ChR2 can elicit robust signal.

FIG. 35a illustrates cholinergic neurons in the basal forebrain were selectively targeted for stimulation. 12 coronal image slices selected from 23 slices that span the whole brain are labeled by dots below the diagram of the brain. FIG. 35b illustrates an anatomical MRI image showing the location of cannula implantation near imaging slice 2 in c. FIG. 35c illustrates gamma (40 Hz) frequency stimulation of cholinergic neurons in basal forebrain leads to a broad network recruitment including the hippocampus. Active regions include M2 (supplementary motor cortex), Cg (cingulate cortex), septal nuclei, VHC (ventral hippocampal commissure), HF (hippocampal formation) including DG (dentate gyms), and RSC (retrosplenial cortex). Color represents phase, i.e. duration, peak timing of activity. White inverted triangle points to stimulation location.

DETAILED DESCRIPTION

Figure 1:
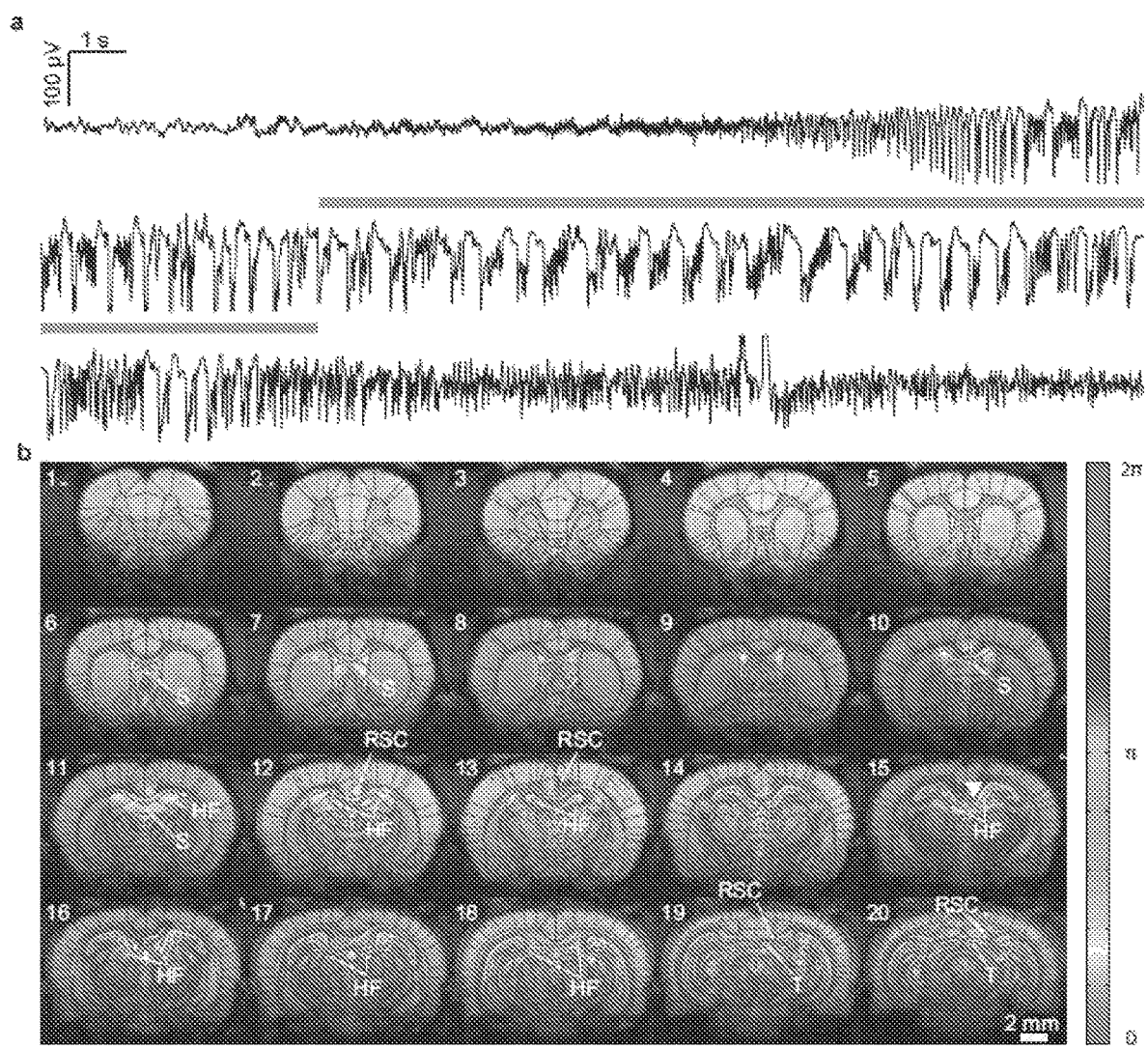
FIG. 1a and FIG. 1b illustrate a seizure generated from excitatory neurons in the dorsal CA1. Electrographic seizure with no behavioral output. Seizure does not propagate to frontal cortex and does not engage Anterior Thalamus.

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Various aspects of the present invention have various implications.

First, from the perspective of the field of epilepsy, the present invention represents a fundamental transformation on how therapies can be designed.

For example, Medtronics spent $200 MM on clinical trial for deep brain stimulation (DBS) therapy in epilepsy. This therapy was not approved in the US due to the ~40% efficacy which was deemed insufficient by the FDA.

The target and parameters for stimulation in this trial was chosen empirically based on evidence that the stimulation of the anterior thalamus has the potential to antidromically suppress seizures originating from the hippocampus. While this is a plausible and was also shown to result in efficacious treatment for many patients with epilepsy, it was not efficacious in the majority of patients.

Importantly, the approach outlined in Example A and Example B, below, provides a direct explanation to this varying efficacy. For example, modeling in accordance with the present invention has shown that many types of seizures generated from the hippocampus do not engage anterior thalamus as part of their seizure network. Therefore, it is unlikely that anterior thalamus stimulation would stop seizures that involve these pathways. However, an alternative subset of hippocampally-generated seizures utilize anterior thalamus as their propagation pathway. Therefore, these seizures would respond to anterior thalamus stimulation therapy. If such evidence now available through our studies undertaken in accordance with the present invention were available before Medtronics engaged in the clinical trial, a more efficient target and patient population selection would have been possible, saving hundreds of millions in cost while enabling faster delivery of more efficacious therapies to the patients in dire need.

Thus, the ability to generate very precise seizures and track their network engagement is an extremely powerful approach which would enable fundamental transformation of the design of therapies in accordance with the present invention. Furthermore, ofMRI approach to identifying therapeutic targets in accordance with the present invention may potentially have a general impact on not only epilepsy but many other neurological diseases including Parkinson's, depression, Alzheimer's, obsessive compulsive disease, and pain.

Second, from the functional brain imaging perspective, the present invention is the first demonstration of the functional brain imaging's capability to capture the dynamic nature of the brain where simple change of stimulation parameter (frequency) results in distinct spatial recruitment of the brain network. Various aspects of the present invention provide for showing show theta vs. gamma frequency stimulation.

Various aspects of the present invention provide for the first showing of how the stimulation frequency not only changes recruitment in spatial network elements but also result in different temporal dynamics at each location that can be captured with functional magnetic resonance imaging (fMRI) hemodynamic response functions (HRF). The HRF from evolving seizures clearly show prolonged sustained response.

Various aspects of the present invention provide for the first showing of the ofMRI technology's ability to track network responses in the whole brain across multiple synapses. For example, FIG. 4 and FIG. 4 shows a network engagement in the frontal cortex area, which clearly have no direct projections from the hippocampus. The precise nature of the stimulation and the high quality imaging in accordance with the present invention, combined with the carefully chosen target enabled clear demonstration of such capability for the first time.

Third, from the perspective of the field of Direct Visualization of Neurostimulation Therapy Effects for (Vagus Nerve Stimulation (VNS), the optogenetic functional magnetic resonance imaging (ofMRI) of the present invention offers a fundamental transformation on how neurostimulation therapies can be designed and evaluated for its therapeutic efficacy. As noted above, Medtronics spent $200 MM on therapies that were not approved in the US.

Figure 2:
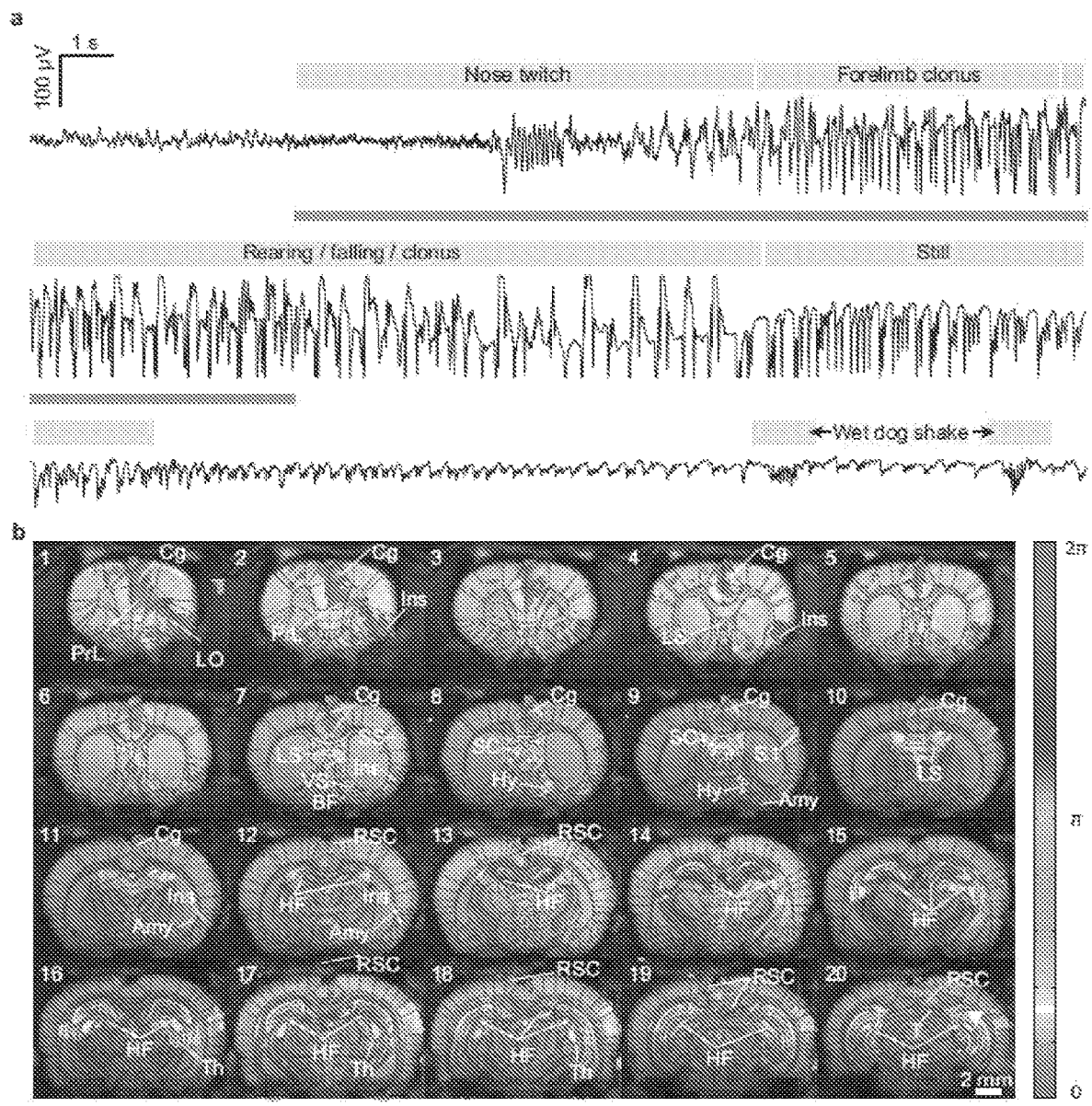
FIG. 2a and FIG. 2b illustrate a seizure generated from excitatory neurons in the ventral CA1. Electrographic seizure with tonic-clonic behavioral seizure. Seizure propagates to frontal cortex area but does not engage Anterior Thalamus.
Figure 3:
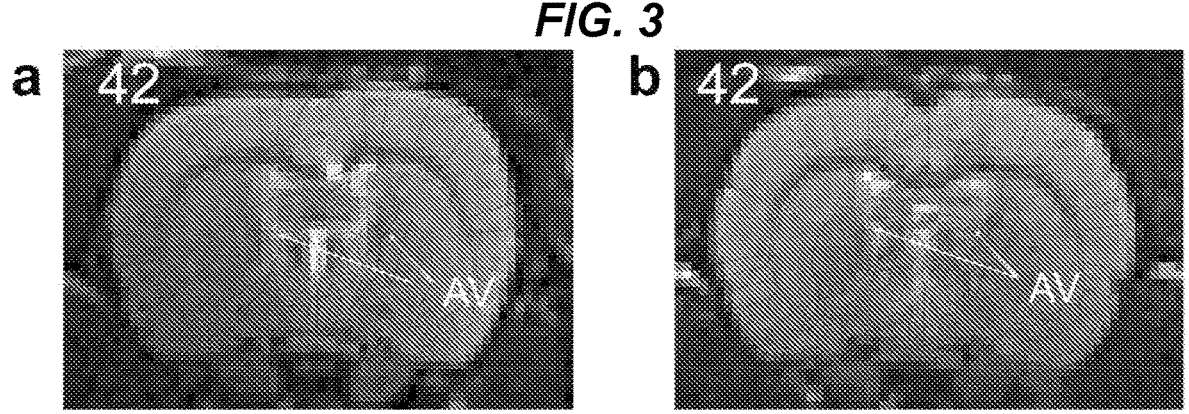

The ofMRI experiments in accordance with the present invention provides a direct explanation to this varying efficacy. Many types of seizures generated from the hippocampus do not engage anterior thalamus as part of their seizure network. Therefore, it is unlikely that anterior thalamus stimulation would stop seizures that involve these pathways. For example, FIG. 1 and FIG. 2 show seizures originating from hippocampus that do not engage the anterior thalamus. However, modeling in accordance with the present invention has shown that an alternative subset of hippocampally-generated seizures utilize anterior thalamus as their propagation pathway (see FIG. 3). Therefore, these seizures would respond to anterior thalamus stimulation therapy. If such evidences now available through our study outlined in this manuscript were available before Medtronics engaged in the clinical trial, a more efficient target and patient population selection would have been possible, saving hundreds of millions in cost while enabling faster delivery of more efficacious therapies to the patients in dire need.

As can be seen from this example, the ability to generate very precise seizures and track their network engagement in accordance with the present invention is an extremely powerful approach which would enable us to fundamentally transform the design of therapies. Similarly, such approach can precisely track the therapeutic stimulus impact with precision. The ofMRI approach in accordance with the present invention to identifying therapeutic targets and evaluating their impact may have a general impact on not only epilepsy but many other neurological diseases including depression, Alzheimer's, Parkinson's, obsessive compulsive disease, and pain.

Due to such high impact potential for neurological therapeutics development, such approaches in accordance with the present invention have the potential to eliminate hundreds of millions on failed trials and to promptly guide us to an optimal therapeutic target. Furthermore, such approaches in accordance with the present invention may these findings with EEG signatures to sort patient groups, and thus optimize therapy for each patient.

For the understanding of the underlying mechanism of action for VNS and to identify target population with efficacious outcome, various aspects of the present invention provide for:
1) Identifying VNS mechanism of action through optogenetic fMRI in rodents with cell-type specificity.
2) Generating distinct seizure types, evaluating efficacy of VNS for each type to identify which types of seizures VNS is effective for, and for each seizure type, identifying unique EEG signatures.
3) Identifying EEG signature in patients through EEG and seizure synchronized MRI, and conducting VNS synchronized fMRI to confirm VNS mechanism of action.

Feasibility of VNS-synchronized fMRI has been shown earlier demonstrating the VNS device's compatibility with MRI (see FIG. 4). Although the information may not have sufficient detail to fully understand underlying mechanism of action, various aspects of the present invention, through integrated approach utilizing integrated animal ofMRI, EEG, and human fMRI, aims to provide full detailed action of mechanism that will completely transform the landscape of target selection and patient selection process.

Example A

Uncovering Seizure Networks of Precise Origin with Optogenetic fMRI

Epilepsy is a disabling neurological disorder of high prevalence, affecting one in twenty-six people in the world, of which approximately one-third are intolerant or refractory to existing therapies. Moreover, its heterogeneous pathophysiology and current inability to observe direct neural pathways associated with seizure onset and propagation pose particular challenges for the development of more effective treatments. Utilizing the optogenetic functional magnetic resonance imaging (ofMRI) method of the present invention, seizures are generated for the first time with precise knowledge of their origin, including cell types, locations, temporal firing patterns, and onset times, while the associated whole brain downstream propagation networks are identified. Specific stimulation of CaMKIIa-expressing neurons at dorsal hippocampus with theta frequency results in a short-duration hemodynamic response mostly restricted to the hippocampal formation. Stimulation at higher gamma frequencies produces longer duration hemodynamic responses that outlast the stimulation in broader areas of the brain, including the septum. Video electroencephalography (EEG) monitoring of theta stimulation shows evoked EEG responses, while gamma stimulation induces electrographic seizures corresponding to the longer duration hemodynamic responses. However, no behavioral seizures are induced from stimulating the dorsal hippocampus. In contrast, gamma frequency stimulation of CaMKIIa-expressing neurons at ventral hippocampus results in electrographic seizures accompanied by behavioral seizures. Corresponding ofMRI-identified seizure network shows involvement of frontal cortical areas. Importantly, these observations illustrate the capability of ofMRI to reveal whole brain dynamic network functions across multiple synapses. While clinical epilepsy may represent a more complex process, direct visualization of repeatable seizure propagation pathways of precise origin will provide an unprecedented opportunity to systematically dissect networks involved in seizures and enable design of targeted therapeutic strategies for medications, focal surgery, and neurostimulation.

Epilepsy results from a variety of genetic and acquired etiologies that increase the susceptibility for spontaneously recurring seizures. Anatomically, such etiologies translate to focal or diffuse lesions with downstream neural network activities that are poorly delineated. Conventional epilepsy diagnostic methods, such as behavioral monitoring, EEG, structural or functional MRI and PET imaging, are of critical importance in the clinical and research settings, but they have limitations in uniquely defining brain networks underlying specific types of seizures. Currently, animal models used to study seizure mechanisms include acute or chronic electrical stimulation, focally-applied or systemically-administered chemical convulsants, focal injury, or genetically-inbred animals, among others. While these models provide pivotal insights and have led to the development of important therapies, conceptual and practical challenges remain. First, in many models, seizure onset is poorly localized, typically involving heterogeneous anatomical populations including fibers of passage and mixed excitatory-inhibitory cell populations, inducing great variability with poor repeatability. Second, seizures occur at unpredictable times, complicating study of time-dependent phenomena, such as tracking of network propagation. Third, without a method to precisely visualize the whole brain's functional involvement in each seizure, it has been difficult to define seizures based on its precise network activity.

Various aspects of the present invention provide for an approach that can precisely identify the network activated by seizures of specific anatomical and cell type of origin. The approach utilizes optogenetic functional magnetic resonance imaging (ofMRI), a pioneering technology that resolves many of the aforementioned challenges. Various aspects of the present invention provide for a method for generating and tracing seizures in otherwise healthy and non-epileptic rats, by modifying hippocampal pyramidal neurons in either dorsal or ventral regions of CA1 to render them excitable by blue light. Seizures can be triggered with millisecond temporal precision, and their propagation patterns subsequently tracked downstream from the seizure focus through the whole brain. Networks activated are dependent upon the site of origin and by the frequency of stimulation. Each seizure is validated by sham-controlled comparisons of EEG and video-recorded animal behavior.

Figure 5:
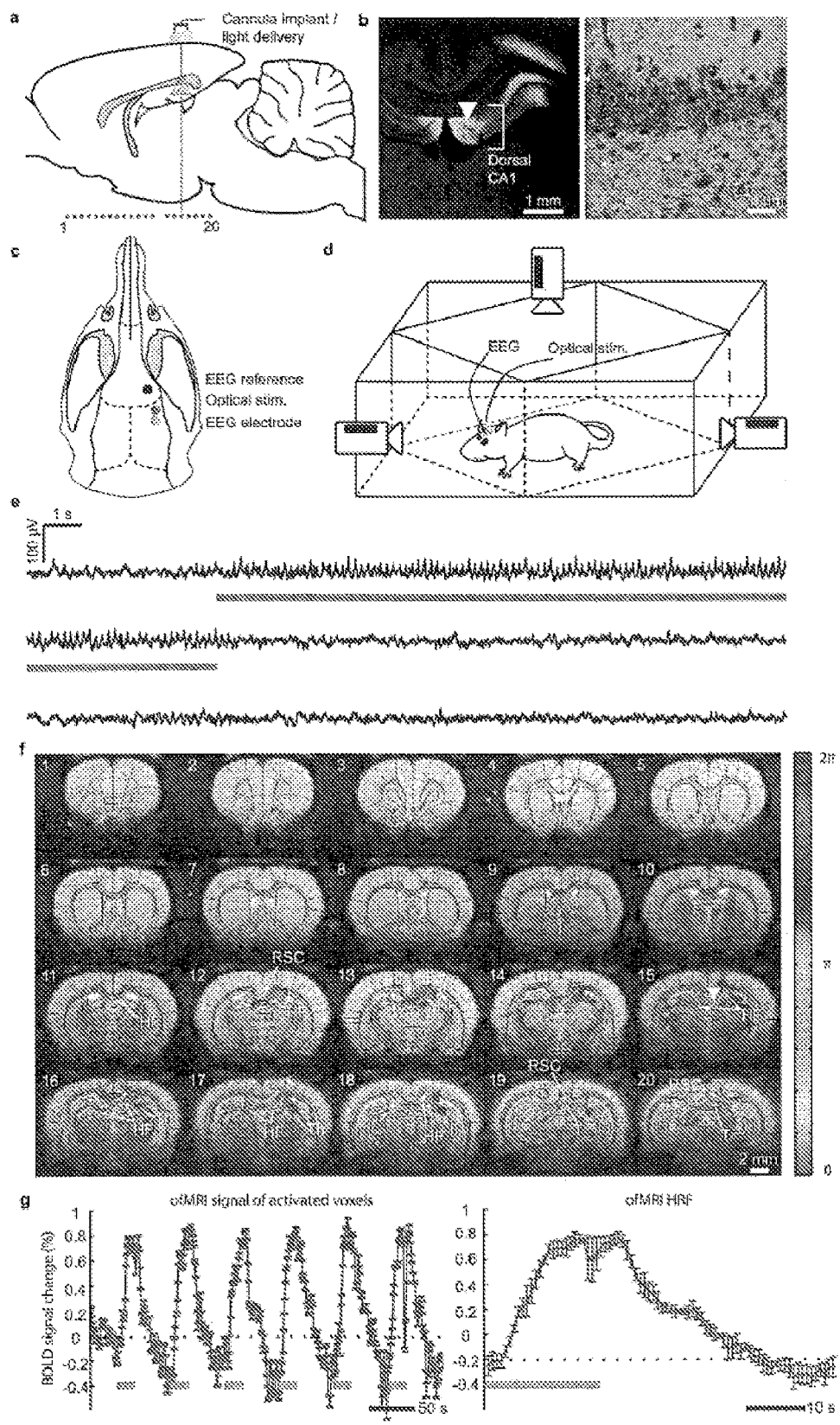

First, the dorsal hippocampal CA1 regions of adult rats were injected with the adeno-associated viral vector AAV5-CaMKIIa::ChR2(H134R)-EYFP. This produces specific expression of a channelrhodopsin (ChR2) specifically in hippocampal pyramidal neurons that express Ca2+/calmodulin-dependent protein kinase IIa (CaMKIIa), but not in GABAergic or glial cells. The dorsal hippocampal virus injection site was also used as the optical stimulation site for EEG, behavior and blood oxygenation level dependent (BOLD) fMRI studies (FIG. 5a). Fluorescent (FIG. 5b, left) and confocal (FIG. 5b, right) images were taken to validate the expression of ChR2-EYFP (enhanced yellow fluorescent protein). EEG and behavioral studies were conducted with the probe location shown in FIG. 5c and a diamond shaped behavioral chamber designed with 3 cameras to capture subtle movements such as facial twitches (FIG. 5d). For the EEG and behavior studies, 473 nm wavelength light was delivered for 20 seconds at 5, 10 and 15 min with a total experiment duration of 20 min. EEG and videos of behavior were recorded continuously during the experiment. Video-BEG recordings were scored blindly by a board-licensed electroencephalographer experienced with both rat and human video-EEGs.

Figure 7:
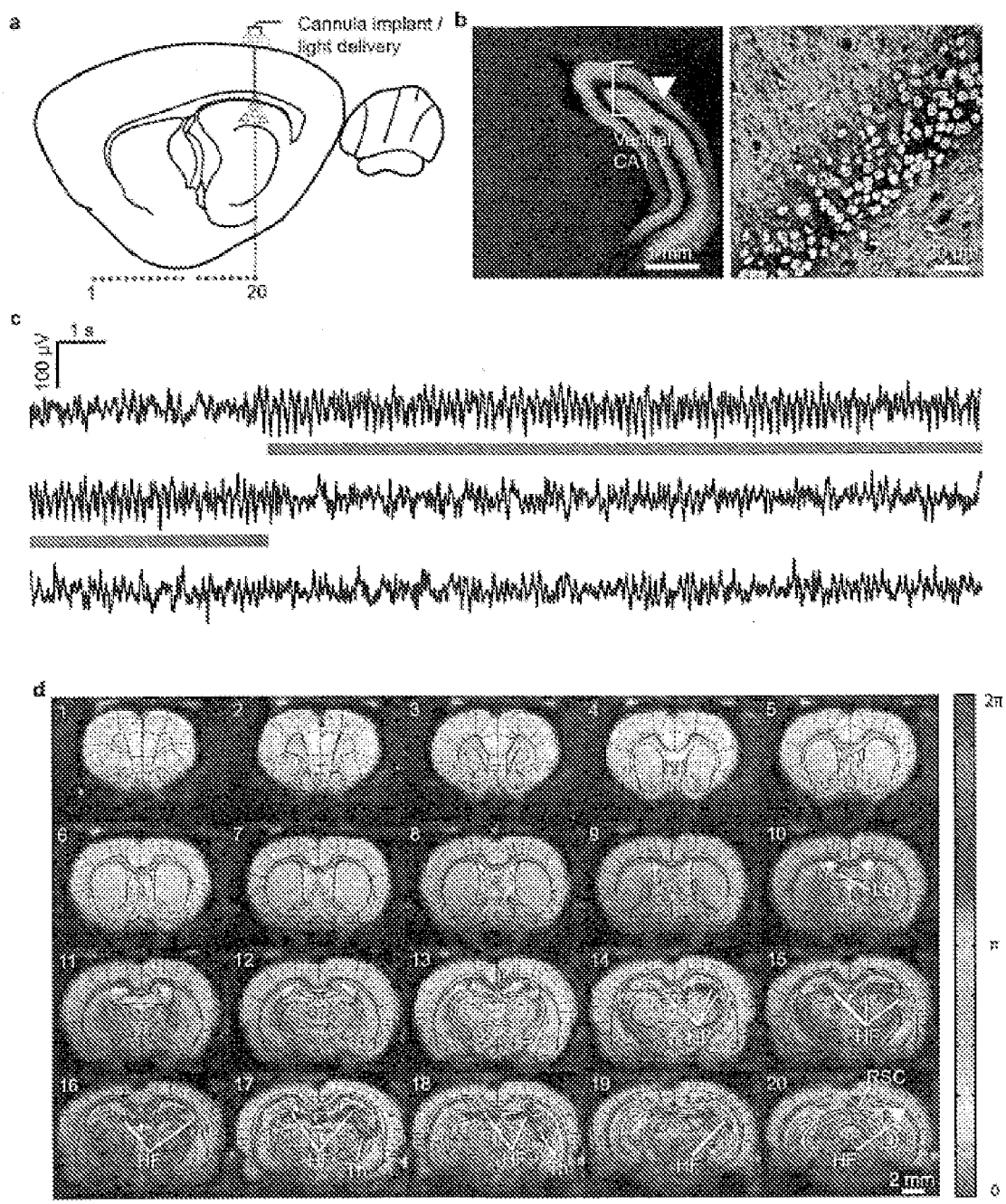

To investigate the impact of low frequency stimulation, blue 473 nm wavelength laser pulses at 6 Hz were delivered to dorsal CA1 at the time indicated by the blue bar (FIG. 5e), resulting only in evoked spikes in concert with each stimulus. With these stimulation parameters, only normal behavior was observed during and after stimulation (supplementary FIG. 7a). To assess associated network function, ofMRI images were acquired with consecutive 0.5 mm coronal slices, taken at least 10 days after virus injection (FIG. 1f). fMRI signals, which are averaged from six independent experiments in five animals, were observed at predominantly ipsilateral dorsal hippocampal formation, ipsilateral thalamus, and retrosplenial cortex. The ofMRI hemodynamic response function (ofMRI-HRF), averaged from all active voxels, is shown in response to each blue light stimulus (FIG. 5g, left). The single epoch trace (FIG. 5g, right) shows that the BOLD signal peaks within the time of stimulation and decays shortly after termination of light stimulation.

Figure 6:
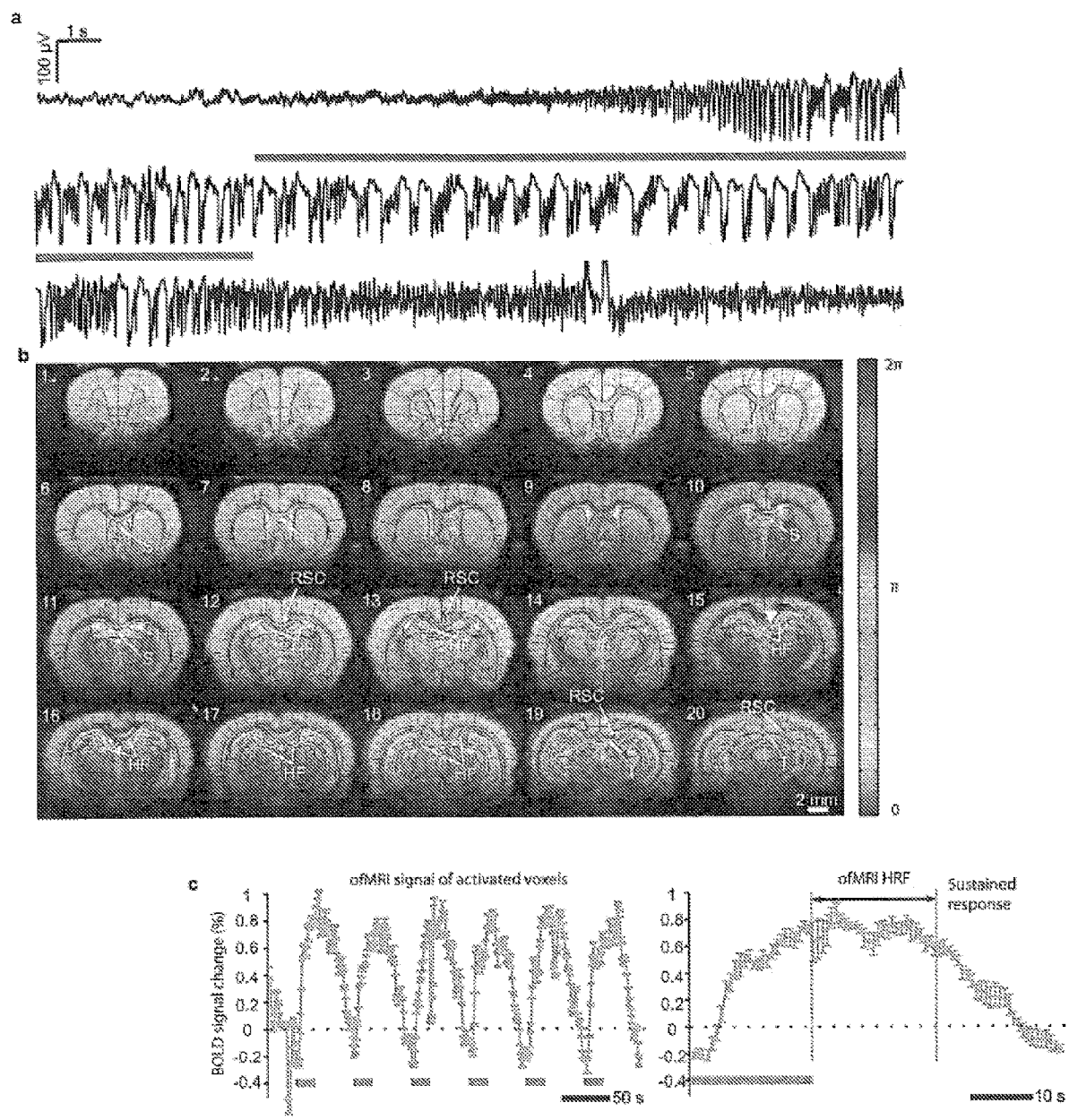

Blue 473 nm wavelength laser pulses at 40 Hz in dorsal CA1 produces an evolving EEG seizure pattern, beginning with evoked spikes, increasing in voltage, and converting to polyspike-slow waves and then rapid spikes (FIG. 6a). Ictal activity outlasts the light stimulation. Despite the ictal EEG pattern, no visible behavioral change accompanied this electrographic seizure (supplementary FIG. 7a). The BOLD response to 40 Hz stimulation at dorsal hippocampal CA1, averaged from six independent experiments in five animals, is shown in FIG. 6b. More extensive activation is observed compared to 6 Hz stimulation (FIG. 50, now involving bilateral dorsal hippocampal formation, bilateral thalamus, ipsilateral retrosplenial cortex, and the septum. Color coding reflects the phase (timing) of the response, with an earlier peak response shown by red marks and later responses in yellow or green. The ofMRI-HRF for 40 Hz (FIG. 6c) shows a significantly prolonged BOLD signal, as compared to 6 Hz stimulation in the same location (FIG. 5g). This corresponds well with the EEG activity that shows ictal activity outlasting the light stimulation for 40 Hz stimulation. This demonstrates the strong correlation between the ofMRI-HRF shape and the underlying neural activity.

In the next studies, adult rats were injected and cannulated (FIG. 7a) at the ventral hippocampal CA1 region. Fluorescent (FIG. 7b, left) and confocal (FIG. 7b, right) images are taken to validate the expression of ChR2-EYFP. Stimulation by blue laser pulses at 6 Hz evokes EEG spike-waves at 6 per second, lasting for the 20 seconds of stimulation (FIG. 7c) with no evident behavioral changes in the video recording for the majority of the experiments. In four experiments with 6 Hz stimulations in ventral hippocampus, the EEG shows spike-waves in three and an evolving seizure in one. Corresponding behaviors are normal in one, wet dog shakes in two, and clonic forelimb and head jerking in one (supplementary FIG. 7b). OfMRI from six averaged experiments in four animals stimulated in ventral hippocampus at 6 Hz show BOLD activation in ipsilateral more than contralateral hippocampal formation, ipsilateral more than contralateral thalamus, bilateral lateral septal nuclei and ipsilateral retrosplenial cortex (FIG. 7d).

Figure 8:
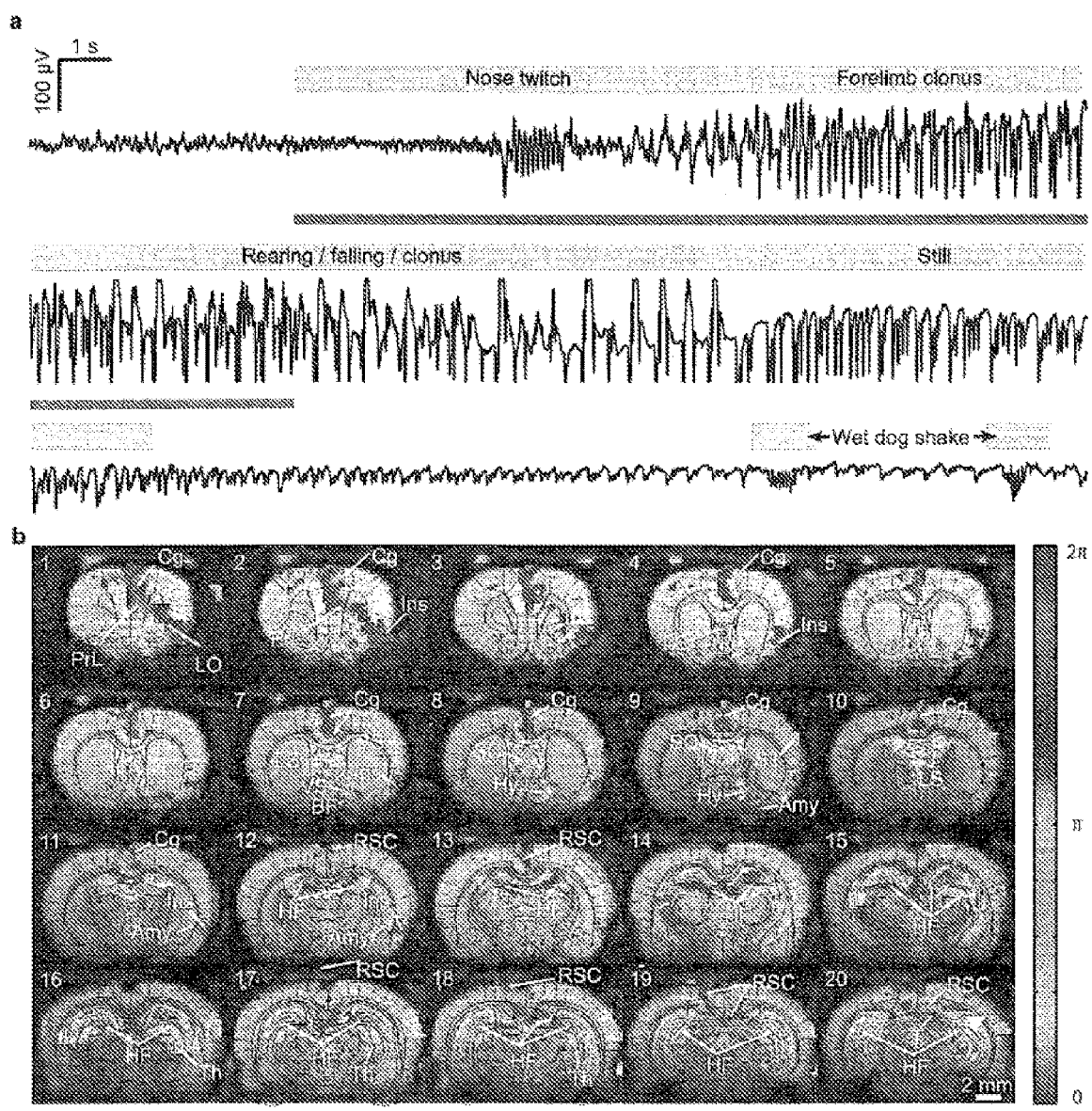
Figure 9:
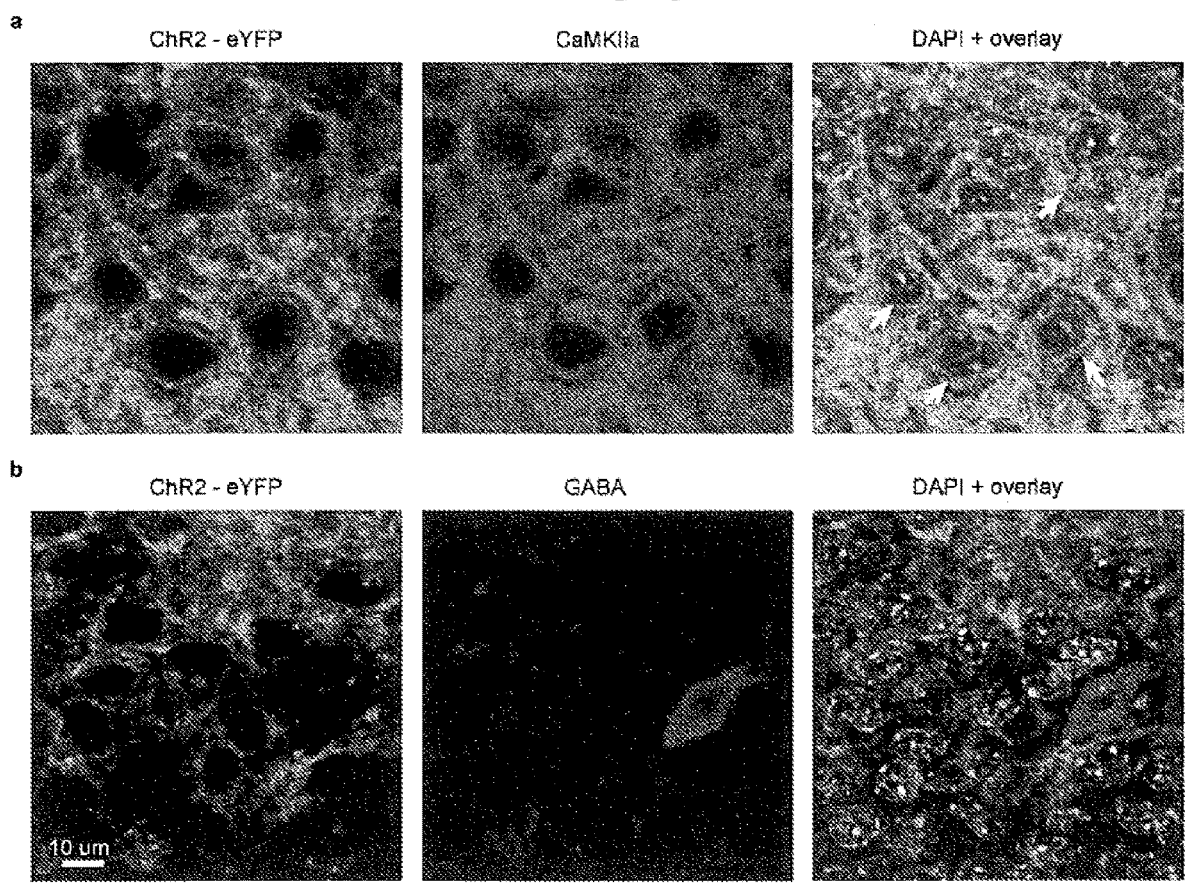
FIG. 9a and FIG. 9b illustrate immunohistochemical characterization of AAV5-CaMKII::hChR2-eYFP that shows specific expression in excitatory neurons. AAV5-CaMKII::hChR2-eYFP: Costaining for the excitatory marker CaMKIIa, inhibitory marker GABA and nuclear marker DAPI. ChR2-eYFP (left), CaMKIIa and GABA (middle), DAPI+overlay (right) are shown. Overlay of eYFP with CaMKII, GABA and DAPI shows CaMKIIa positive cells (FIG. 9a, white arrows) but not GABA positive cell coexpressing eYFP (FIG. 9b). 98% of cells expressing eYFP were positive for CaMKII (1745/1786 cells, n=5 animals). 51% (1786/3479, n=5 animals) of all CaMKII cells counted in the opsin expression CA1 region of 0.5 mm$^3$ were eYFP positive.
Figure 10:
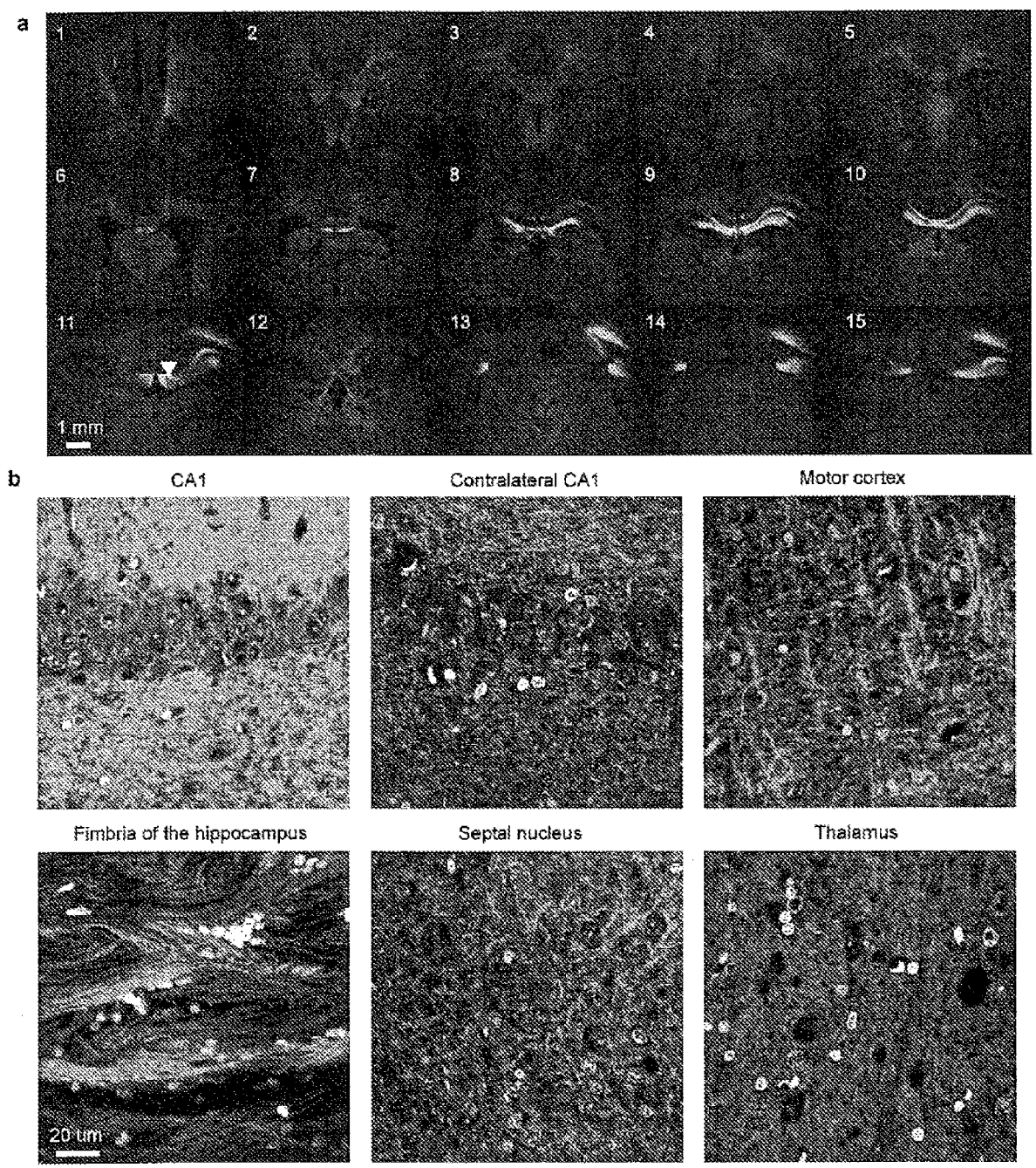
FIG. 10a and FIG. 10b illustrate fluorescent and confocal images that show AAV5-CaMKII::hChR2-eYFP is expressed in dorsal hippocampal CA1 and anatomically connected regions.
Figure 11:
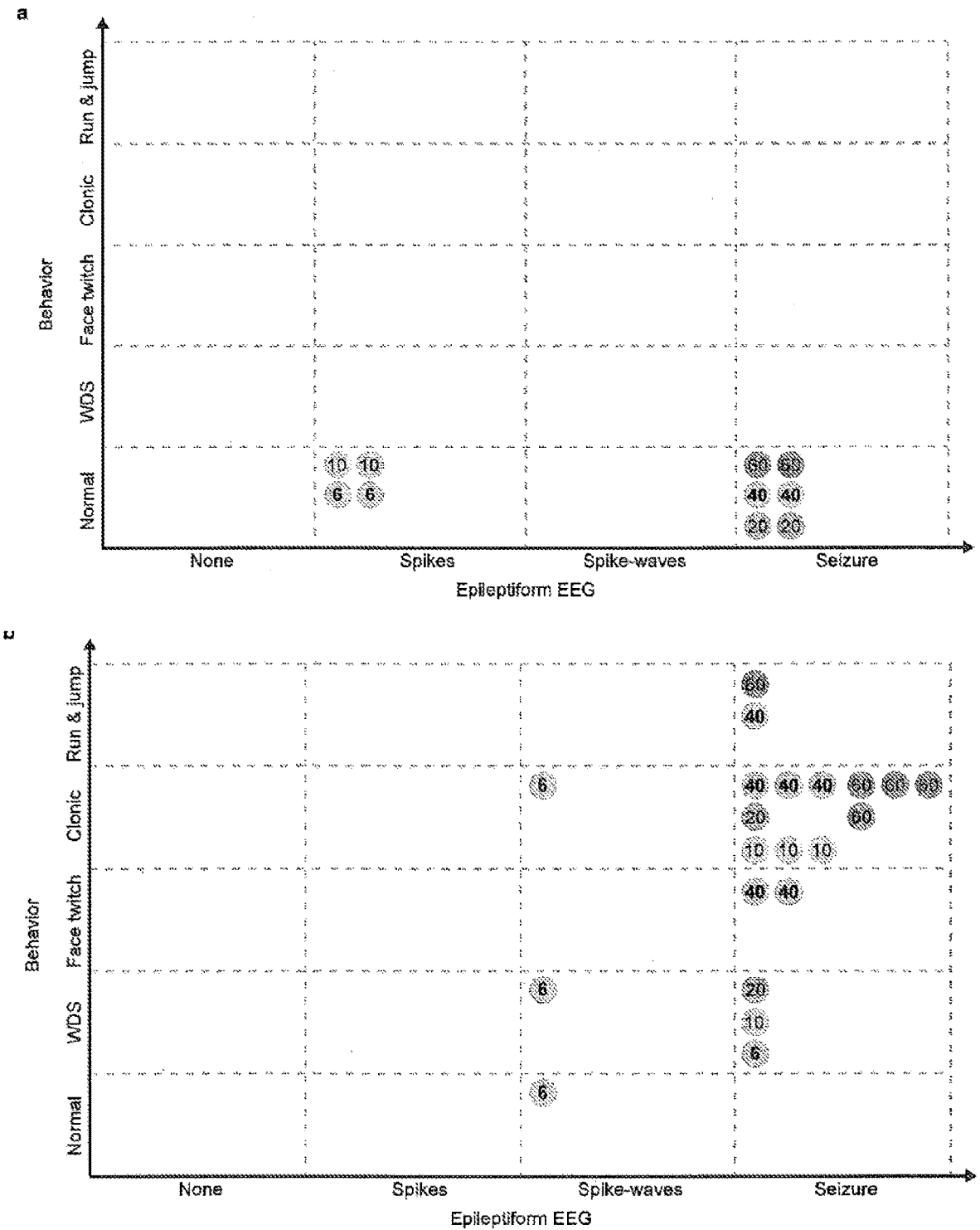
FIG. 11a and FIG. 11b illustrate an EEG and behavior of dorsal and ventral hippocampus stimulation.

Ventral hippocampal stimulation at 40 Hz produces an evolving EEG seizure pattern (FIG. 8a) during and after the light stimulation. Corresponding behaviors include face twitching, clonic seizures or a running jumping seizure (supplementary FIG. 7b). Consistent with the EEG readings, the 40 Hz ventral hippocampal stimulation BOLD signal from six averaged experiments in four animals is also extensive (FIG. 8b). Bilateral activations are observed at ventral and dorsal hippocampus, septal nucleus, ventral striatum, and horizontal band of Broca. Unilateral activations are seen in rostral regions of the brain including claustrum, anterior cingulate cortex, prelimbic regions, ventral and lateral orbital cortex, anterior insular regions and amygdala areas. Less prominent or delayed activation takes place in the retrosplenial cortex and somatosensory regions.

Various aspects of the present invention demonstrate the feasibility of tracking brain network activation across the whole brain by optogenetically-triggered seizures of known origin and onset time. With "hyper-specific" origin, the electro-behavioral manifestations of the seizures presented are comparable to those seen with other animal models and to human electroencephalographic seizures, while having reproducible dependency on the cell-type of origin and stimulation parameters. In accordance with the present invention, four distinct patterns of network recruitment are seen with dorsal or ventral hippocampae stimulation at theta and gamma frequencies. With dorsal hippocampal stimulation, gamma frequency stimulation results in more extensive network recruitment with longer duration ofMRI-HRF and BEG-detected electrographic seizures, compared to theta frequency stimulation. However, dorsal hippocampal stimulation fails to activate the anterior regions of the brain or the subcortical areas involved in executive and motor functions. The limited network involvement observed with ofMRI is in good agreement with the lack of ictal behavior in these animals. Stimulation of the ventral hippocampus, in particular at 40 Hz, recruits an extensive set of structures that encompass anterior cortical and subcortical regions. The extensive activation is consistent with fully expressed clonic seizures. Electrographic seizures evoked from ventral hippocampus always manifest in motor seizure behaviors, in contrast to seizures in dorsal hippocampus, which are behaviorally silent. The patterns of ofMRI activation with dorsal or ventral hippocampal stimulation also correspond to the anatomical connectivity of these two regions of hippocampus. Network mapping of the seizures by ofMRI therefore enables dissection of network components and electro clinical manifestations of seizures originating from specific cell populations.

It should not be assumed that the ofMRI-visualized networks represent all elements involved in seizures due to incomplete understanding of neuro-vascular coupling and uncertainty about the minimum metabolic activation necessary for visualization. Nevertheless, the strong correlation between ofMRI maps and BEG/behavioral recordings represents the highest definition and fidelity for the study of neurological disease networks using ofMRI. In accordance with the present invention, EEG recordings were made from a single channel near the stimulation site for simple validation of seizure activities. However, further investigation in combination with multi-channel EEG will be useful to spatially correlate EEG recordings with ofMRI signals.

Precisely delivered optogenetic stimulation and subsequent time-locked high-resolution fMRI pathway imaging reveals different network activations associated with seizures beginning in highly focal neuronal populations. The networks activated during seizures are highly reproducible and correlate well with EEG and behavioral observations. The duration of the hemodynamic response function accurately reflects the temporal duration of the network activation, illustrating ofMRI technology's capability to investigate temporal neural activity patterns in addition to providing spatial information. The recruitment of areas known to be poly-synaptically connected with ventral hippocampus also demonstrates ofMRI's capability to reveal dynamic network activities across multiple synapses. While clinical seizures likely arise from mixed and complex cell populations, the approach in accordance with the present invention will facilitate systematic dissection and analysis of the components of complex seizures. Therapies that depend upon precise anatomical knowledge, such as surgical lesions, focal neurostimulation or focal drug application will benefit from a clearer understanding of the specific brain networks that are involved with various electro-clinical patterns.

Methods Summary

Optogenetic fMRI Data Acquisition and Analysis

Anesthetized (~1.0-1.5% isoflurane) animals were connected to the 473 nm laser and stimulated while being scanned by a gradient recalled echo (GRE) BOLD imaging sequence using a 7 T small animal dedicated MRI scanner. Acquired data was reconstructed every 750 ms, motion corrected, and aligned to a common selected image for averaging. The averaged datasets were then analyzed by frequency domain analysis that computes significance of frequency components synchronous to stimulus.

EEG and Behavioral Studies

After the ofMRI studies, each rodent subject was implanted with a skull EEG electrode. The animal was then acclimated and tested in a diamond-shaped box with three cameras to record behavior. In all experiments, the subjects were stimulated after 5 minutes of baseline acquisition for 20 or 40 seconds at 5, 10, and 15 minutes from the start of data acquisition. The EEG signal was recorded at 1 kHz sampling rate. Five different types of trials with 6, 10, 20, 40 Hz stimulation were performed.

Opsin Expression Validation and Immunohistochemistry

Brain slices were prepared for optical microscopy and immunohistochemistry to validate specificity, sensitivity and spatial distribution of opsin expression. Subjects' brains were first extracted and fixed in 4% PFA overnight and equilibrated in 10%, 20%, and 30% sucrose in PBS at 4° C. Coronal sections (50 μm) were prepared on a freezing microtome and consecutive sections (500 µm apart) were examined for opsin expression. Confocal fluorescence images were acquired on a laser confocal microscope using oil immersion objectives.

Example B

The following example is described with reference to FIG. 9 to FIG. 12.

Adeno-Associated Virus Production and Transduction.

The pAAV-CaMKIIα-ChR2(H134R)-EYFP plasmid was constructed by cloning pAAV-CaMKIIα-ChR2(H134R)-EYFP into an AAV backbone using MluI and EcoRI restriction sites. The map is available online at www.optogenetics.org. The recombinant AAV vector was serotyped with AAV5 coat proteins and packaged by the University of North Carolina viral vector core; titer was 2×10 particles/mL.

Stereotactic Injection of Virus and Cannula Placement

AAV5-CamKIIa-ChR2-EYFP viral vectors were obtained from the Deisseroth lab, packaged at the University of North Carolina vector core and stored at −80° C. AAV5 was selected since it generates anterograde labeling and selectively targets neurons with cell bodies at the site of injection. The CamKIIa promoter was used to produce ChR2 only in CamKIIa-expressing excitatory neurons while EYFP was used to co-localize ChR2 expression for validation. Sprague-Dawley rats (>11 weeks old, 250-350 g) were used as subjects; animal husbandry and experimental manipulation were in strict accord with guidelines from the National Institute of Health and the UCLA Institutional Animal Care and Use Committee (IACUC). Rats were anesthetized with 5% isoflurane in an induction chamber and maintained at 2-3% with a nose cone during surgeries. After securing the animal onto a stereotactic frame and heating pad, artificial tears were applied on the eyes to prevent desiccation during surgery. Buprenorphine (0.05 mg/kg) was injected subcutaneously for pain relief. Heads were shaved and cleaned with 70% ethanol and betadine to minimize the possibility of infection. Following a midline incision, small craniotomies were made using a dental drill mounted to the stereotactic frame. Two types of surgeries were conducted: I) viral injections (one injection per rat, 2 µl/site) and cannula (3.4 mm projection) implantations in dorsal CA1 (+1.2 mm ML right hemisphere, −4.3 mm AP, injection at −3.6 mm DV); II) viral injections (one injection per rat, 2 µl/site) and cannula (4.4 mm projection) implantations in ventral CA1 (+5.2 mm ML right hemisphere, −5.8 mm AP, injection at −4.6 mm DV). MRI and immunohistochemistry validated the precision of viral expression and stimulation location. Animals with erroneous probe location were eliminated. Concentrated virus was delivered using a 10 µl syringe and a 34 gauge metal needle (World Precision Instruments Inc.) at a 150 nl/min flow rate driven by a micro-syringe pump controller. The syringe needle was left in place for ten minutes before being slowly withdrawn. Custom-designed fiber-optic cannulas with the optical fiber extending from the base into the desired DV coordinates were mounted on the skull and secured using one layer of metabond (Parkell Inc.) until solidification (ten minutes). The incisions were sutured closed with running 5-0 nylon skin sutures and animals were kept on the heating pad until recovery from anesthesia (typically about fifteen minutes). Buprenorphine was injected subcutaneously twice daily for 48 hours post-operatively to minimize post-operative discomfort.

ofMRI Experiment fMRI scanning was performed in a 7 T Broker Biospec small animal dedicated MRI system in Ahmanson-Lovelace Brain Mapping Center at UCLA. Animals were initially anesthetized in an induction chamber with 5% isoflurane and intubated before placing onto custom-made MRI-compatible cradles with ears and teeth secured. A 39 mm outer diameter 25 mm inner diameter custom-designed transmit/receive single-loop surface coil was centered over the region of interest on the skull to maximize signal-to-noise ratio. Optical fibers of 62.5 µm core diameter were connected to a blue laser source (473 nm) and coupled with fiber-optic cannulas. During fMRI scanning, animals were placed into the iso-center of the magnet while artificially ventilated (45-55 strokes/min) under light anesthesia using a ventilator (Harvard Apparatus, Model 683 Small Animal Ventilator) and calibrated vaporizer with a mixture of $O_2$ (35%), $N_2O$ (63.5%) and isoflurane (1.5%). Expiratory $CO_2$ was kept at 3-4% and body temperature was maintained at 36-38° C. using heated airflow. T2 weighted high-resolution anatomical images were acquired prior to fMRI scanning to check for brain damage and probe placement. Gradient recalled echo (GRE) BOLD methods. were used to acquire fMRI images following different optical stimulation parameters. One 60-second cycle of stimulation contained 20 seconds of optical stimulation in desired frequencies with a 30% duty cycle and 40 seconds without optical stimulation, allowing six cycles per experiment. Stimulation was performed at frequencies of 6, 10, 20, 40 and 60 Hz. The optical fiber output power was set to be approximately 2.5 mW, which did not induce any heating related artifacts in control experiments.

Image Acquisition and Reconstruction.

Gradient-echo (GRE)-BOLD sequences were used for the acquisition. The pulse sequences were designed to have 35×35 $mm^2$ in-plane field of view (FOV), 0.5×0.5×0.5 $mm^3$ spatial resolution and sliding window reconstruction that can update the images every repetition time (750 ms). The GRE-BOLD fMRI was designed to be a two-dimensional, multi-slice, gradient-echo sequence with four-interleave spiral readout; 750 ms repetition time (TR) and 12 ms echo time (TE) resulting in 23 slices covering 11.5 mm slice direction volume. This specific design allowed large-volume mapping of the brain during optogenetic control. Upon completion of custom-designed GPU-based parallel reconstruction and motion correction, frequency domain analysis was performed and coherence values were calculated. Activation maps were acquired following a 0.35 coherence value threshold using custom-written algorithms and software (MRVista). A digital standard rat brain atlas was used to confirm the location of implanted cannulas and localize activated voxels to specific brain regions.

ofMRI Data Analysis.

The ofMRI GRE BOLD spiral kspace sample was first reconstructed through a 2-dimensional (2D) gridding reconstruction method. For both dorsal and ventral CA1 experiments, the final fMRI image is averaged from eight independent experiments (each contains six scans) in six animals. For accurate averaging, all images were registered so that there are no misalignments. As a first step, an image was selected that had the median location so that the transitions and rotations required for other images to register are kept at a minimum. One 3D time frame of the selected experiment data was then extracted and used as a template for inter experiment image transformation matrix calculation for registration. A custom developed Matlab tool was first used to determine six-degree-of-freedom matrices that can transform each experiment's selected 3D images to be registered to the selected template images. Another custom written GPU-based parallel motion correction tool was then used to conduct the actual transformation for inter-experiment registration and then to correct for motion within each experiment's time series and six repeated scans. After all images were aligned, they were averaged to produce the final fMRI 4D image. The dataset was then analyzed by frequency domain analysis.

EEG Electrode Implantation

After completion of the ofMRI studies, the animals underwent additional surgeries for EEG electrode implantation. Animals were anesthetized with 5% isoflurane in an induction chamber and maintained at 2-3% with a nose cone during surgeries. Animals were secured onto a stereotactic frame and heating pad, artificial tears were applied to prevent desiccation during surgery and buprenorphine (0.05 mg/kg) was injected subcutaneously. The rats' heads were shaved. Ethanol 70% and betadine were applied to the bare scalp as antiseptics. A midline incision was made with a sterile scalpel and the regrown membranes on the skull were removed with sterile cotton applicators. Two stainless steel screws (0-80, 1.5 mm diameter, Plastics One Inc.) were attached to ~2.0 cm of insulated wire (30 gauge, R30Y0100, Wire Wrapping Wire, O.K. Industries) and affixed to the skull over the frontal cerebral cortex. One electrode was placed approximately 3.0 mm anterior and 2.0 mm to the right of bregma for a reference, and the other electrode for hippocampal EEG recording at the edge of the cerebral cortex above I) the dorsal CA1 or II) the ventral CA1 approximately 1.5 mm caudal to the optical fiber implant location in each animal. After the electrodes were mounted on the skull they were secured using one layer of metabond (Parkell Inc.) until solidification, requiring approximately ten minutes. The incisions were closed with running 5-0 nylon skin sutures. Animals were kept on the heating pad until recovery from anesthesia at approximately 15 minutes. The buprenorphine was injected subcutaneously every 12 hours post-operatively for 48 hours to minimize pain. Animals were closely observed for discomfort or infection for one week and provided with trimethoprim-sulfamethoxazole antibiotic (48 mg/100 ml) in their water.

Video-EEG Recording

Rats were acclimated to a diamond-shaped box with cameras mounted at each end and on top. This shape makes corners in the box more obtuse and helps to visualize the animal head-on. No distracters were placed in the cage. Animals received food and water between trials. EEG recordings were performed for five minutes of baseline, followed by 20 or 40 seconds of optogenetic light stimulation at 5, 10, and 15 minutes (4:20 of no stimulation between), such that each trial lasted for 20 min. A commercial digital EEG system, sampling at 1000 points per second per channel was used to record EEG. Different parameters of stimulation frequency were tested in a randomized trial order. Tests containing five trials (6, 10, 20, 40 and a sham) were repeated three times for each animal. The sham experiments lowered the power of the laser to a level that would attenuate the light by two orders of magnitude in the brain, thus making any effect negligible, but still able to produce a bright blue flash visible to the animal and investigators. During EEG recording, all three video cameras recorded the behavior of the animal. Because ofMRI was recorded in rats anesthetized with inhalation of $O_2$ (~35%), $N_2O$ (~63.5%) and isoflurane (1.5%), video-EEG also was analyzed in experiments in three animals inhaling this mixture.

Each video-EEG clip was classified by an observer blinded to treatment into one best category: normal, spikes, spike-waves or an evolving electrographic seizure. Video clippings paired to each EEG were classified according to a modified Racine scale for seizures: 1=mouth and facial movements, 2=head nodding, 3=forelimb clonus, 4=rearing, and 5=rearing and falling (a full clonic motor seizure with loss of postural control), and extra categories WDS for wet dog shakes and R for running-jumping seizures. Categories 3, 4 and 5 sometimes were combined into a super-category of "clonic seizure." The most electrographically prolonged seizure of the three produced in each session was be used for scoring, almost always the first.

Opsin Expression Validation

Upon completion of video-EEG recording, rats were deeply anesthetized with isoflurane (Sigma) in a knockdown box and transcardially perfused with 0.1M PBS and ice-cold 4% paraformaldehyde (PFA) in PBS. Brains were extracted and fixed in 4% PFA overnight at 4° C. The brains were equilibrated in 10%, 20% and then 30% sucrose in PBS at 4° C. Coronal sections (50 µm) were prepared on a freezing microtome (HM 430 Sliding Microtome, Thermo Scientific Inc.). Consecutive sections (500 µm apart) were mounted on microscope slides and the opsin expression was examined with a Leica fluorescent microscope (Leica EL6000).

For immunohistochemistry, free-floating sections were processed with 2% normal donkey serum, 1% bovine serum albumin and 0.2% Triton X-100 for 30 minutes and exposed 48 hours at 4° C. to primary antibodies against: Mouse monoclonal CaM-kinase IIa (CaMKIIα, 1:400, Abcam, Cambridge, Mass.); Mouse monoclonal pan-neuronal marker NeuN (1:200, EMD Millipore, Temecula, Calif.); Rabbit polyclonal parvalbumin (1:1000, Millipore, Billerica, Mass.); rabbit polyclonal gamma amino-butyric acid (GABA, 1:10K, Calbiochem, San Diego, Calif.); and rabbit polyclonal glial fibrillary acidic protein (GFAP, 1:400, Millipore, Billerica, Mass.). Sections were then washed with PBS and incubated for 2 hours at room temperature with secondary antibodies: Alexa Fluor®-594-conjugated AffiniPure donkey anti-mouse IgG and Alexa Fluor®647-conjugated AffmiPure donkey anti-rabbit IgG (both 1:1000, Jackson Laboratories, West Grove, Pa.). Double or triple immuno-fluorescence was assessed with a laser confocal microscope (Leica CTR 6500).

Example C

Transforming Neurostimulation for Epilepsy

1. Challenge, Innovation and Impact Statement:

Deep brain stimulation (DBS) is a potentially valuable new therapy for brain disorders, including Parkinson's disease, tremor, depression, pain, epilepsy and many others. However, a rudimentary understanding of DBS mechanisms limits effectiveness. DBS can inhibit or excite local tissue, disrupt network synchrony, activate fibers of passage and generate uncertain remote actions. Although the best targets are not necessarily known, the targets used are heterogeneous in their response to stimulation. Stimulation parameters in clinical trials are mostly guesswork. A new technology, optogenetic functional magnetic resonance imaging (ofMRI), is in a position to surmount these limitations. ofMRI can display specific brain networks involved in neurological conditions, visualizing neuronal activity in the whole 3D space of a brain. Optogenetics selectively can excite or inhibit specific neuronal populations by controllable and repeatable pulses of light. ofMRI may be used to dissect mechanisms of brain stimulation, employing the resulting insights to design rational approaches to electrical brain stimulation. Using epilepsy as an example, a controllable model of seizures may be developed propagating from hippocampus, track and inhibit these seizures through propagation networks, and tailor electrical stimulation to the subregions and parameters discovered by optogenetic mapping.

Figure 13:
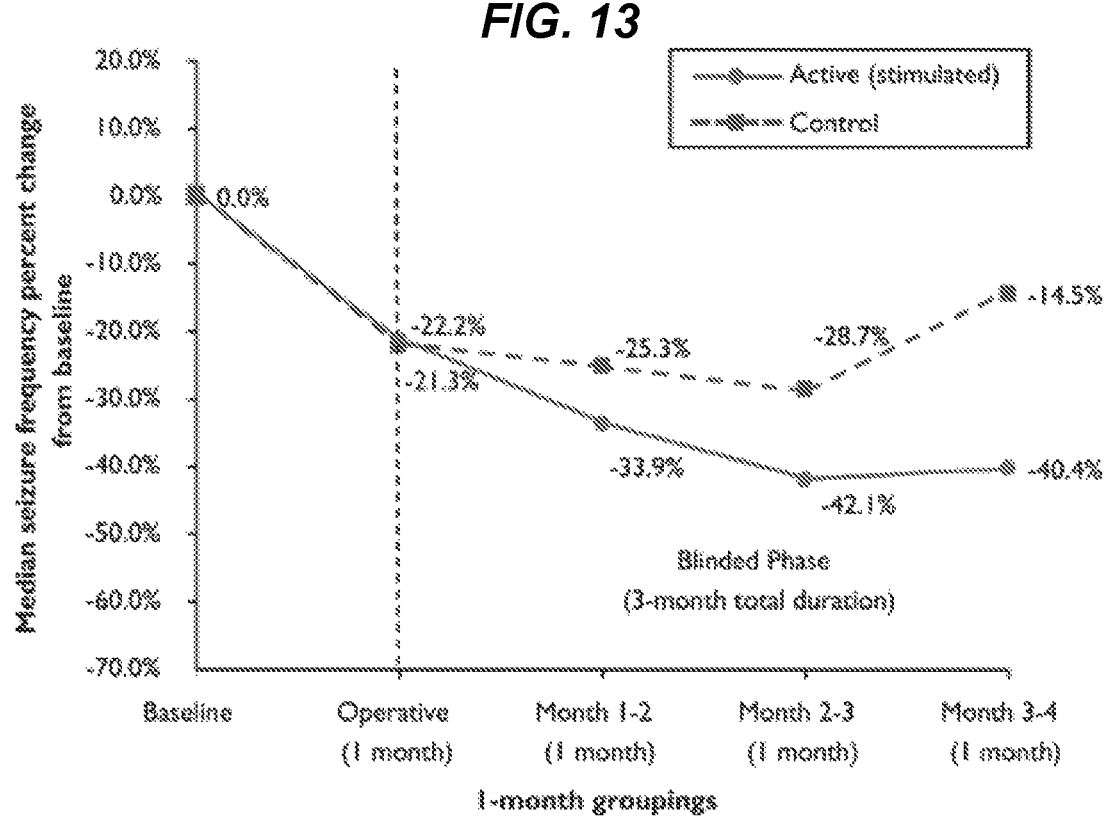
FIG. 13 illustrates ANT stimulation reduces seizures. 110 patients had electrodes implanted bilaterally in ANT and recovered for 1 month. For the next 3 months, patients were randomized to stimulation at 5 V (circles, solid line) or 0 V (squares, dotted line), unaware of their treatment group. Significantly fewer seizures (p<0.04) occurred in the group receiving 5 V active stimulation.

2. Rationale:

DBS for epilepsy can be taken as an illustrative example of the promise and limitations of therapeutic DBS. Two recent multicenter randomized, controlled trials of brain stimulation for medication-resistant epilepsy (one led by the current applicant) showed statistically significant benefit, but with only about a 40% median reduction of seizures (FIG. 13). The anterior nucleus of thalamus (ANT} was used as the target of stimulation in one of the trials, because of its ability to influence the frontal and mesial temporal regions where most seizures originate. The degree of benefit depended critically on parameters of stimulation. One patient, for example, had seizures triggered each time a 5 V stimulation was activated on a six-minute cycle, but subsequently had a substantial reduction in seizures with a 4 V stimulation. How much more benefit could be realized if the best parameters of stimulation were known? What is the best voltage (or current), stimulation frequency, pulse width, bipolar versus referential stimulation, continuous, intermittent or responsive stimulation? Most importantly, what are the best targets? Targeting encompasses not only the general region for placing an electrode, but efforts to stimulate specific cell populations, with or without activation of fibers of passage. Stimulation of the subthalamic nucleus, for example, has been said to inhibit seizures by antidromic activation of cortical-subthalamic fibers. Electrical stimulation of ANTS activates not only local neurons, but also the mammillothalamic tract, serotonergic, cholinergic and glutamatergic fibers of passage.

Optogenetics is a novel technology that can modulate brain circuits with much greater specificity than can electrical stimulation. Specific cell populations can be selectively excited or inhibited with negligible effects on adjacent fibers of passage. ofMRI, by combining optogenetic control with fMRI readout, can highlight downstream structures activated by optogenetic stimulation of specific cell populations. Such a degree of specificity would be immensely helpful in design of future clinical trials. Where, for example, should electrical stimulation take place to influence a mesial frontal supplementary motor region seizure focus, versus a mesial temporal or lateral temporal seizure focus? Does very high-frequency stimulation at several hundred hertz (Hz) better inhibit circuits involved in epilepsy than does low frequency stimulation? Can the deleterious biphasic excitation-inhibition effects of stimulation be minimized? The specificity of ofMRI mapping provides a previously unavailable opportunity to clarify these difficult questions. Using actual optogenetic techniques to treat epilepsy may be some years in the future. The precision and efficiency of optogenetics as an exploratory tool may transform how electrical stimulation is applied.

3. Approach:

Various aspects of the present invention may be summarized as follows.

Optogenetic Seizure Model Development: Develop and validate a model of hippocampal seizures produced by optogenetic stimulation, which will provide a model with an accurate anatomical starting point, cell types of origin, and seizure onset time. This will facilitate systematic study and optimization of neuro stimulation therapy for epilepsy.

Inhibit Seizures with Cell-type Specific Neurostimulation: Optogenetic stimulations that enable control of specific cell types will be used to identify optimal stimulation target and parameters, best able to inhibit (prevent, shorten or ameliorate behavioral intensity) seizures. Our search will start by investigating the propagation pathway of hippocampal seizures, as discussed in the background section below. Optogenetic inhibitory and disruptive stimulatory techniques may be used to determine the key structures along this pathway that can inhibit seizures.

Translate to Electrical Stimulation: In this section, the lessons learned from the first two aims will be used to accelerate optimization of electrical stimulation therapy. The metabolic anatomy produced by different electrical stimulation parameters in rat ANT may be investigated to obtain a better understanding of the current clinical variations. Parameters of electrical stimulation may be set to produce a brain activation pattern most like the one produced by successful optogenetic stimulation identified in aim 2. This will be evaluated by the ability of that stimulation to inhibit the optogenetic and a conventional generalized seizure model made by the GABA antagonist, pentylenetetrazol (PTZ). The temporally precise hippocampal optogenetic seizure model of aim 1 may be used to determine how long the anti-seizure effect endures after an electrical stimulation to ANT. These experiments may pave a path to transform the clinical role of DBS for epilepsy.

BACKGROUND

Optogenetics, is a revolutionary neuro-modulation technology in which single-component microbial light-activated trans-membrane conductance regulators are introduced into specifically targeted cell types and circuit elements using cell type specific promoters to allow millisecond-scale targeted activity modulation in vivo. Channelrhodopsin (ChR2) is a monovalent cation channel that allows Na+ ions to enter the cell following exposure to 470 nm blue light; whereas, the halorhopdopsin (NpHR) is a chloride pump that activates upon illumination with 580 nm yellow light. As the optimum activation wavelengths of these two proteins are over 100 nm apart, they can be controlled independently to either initiate action potential firing or suppress neural activity in intact tissue, and together may modulate neuronal synchrony. Both proteins have fast temporal kinetics, on the scale of milliseconds, making it possible to drive reliable trains of high frequency action potentials in vivo using ChR2 and suppress single action potentials within high frequency spike trains using NpHR. Thus far, one of the greatest challenges in neuroscience has been the difficulty of selectively controlling different circuit elements of the brain to understand its function. Optogenetics, by enabling in vivo control of genetically targeted circuit elements, allows the study of the systematic contributions of each circuit element.

Figure 15:
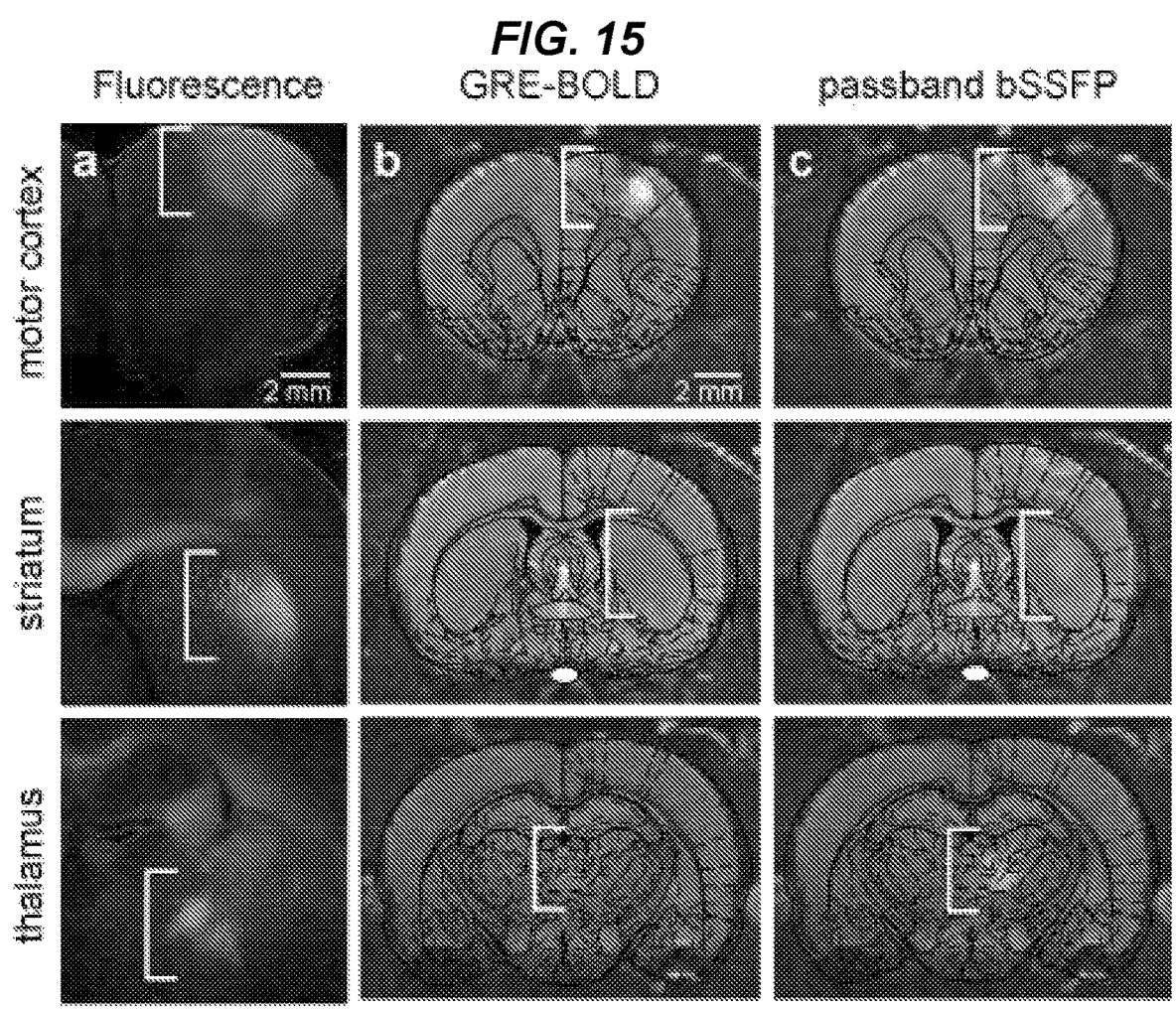
FIG. 15 illustrates ofMRI circuit mapping: conventional BOLD and passband bSSFP-fMRI. Injection of CaMKIIa::ChR2-EYFP in M1, as expected, leads to opsin expression in motor cortex, striatum, and thalamus, i.e. the primary site of injection and sites where axons of expressing neurons project to (left). Conventional BOLD fMRI activity map superimposed onto appropriate anatomical and atlas images. Passband bSSFP-fMRI activity map superimposed onto appropriate anatomical and atlas images, which more fully captures circuit-level activity.
Figure 16:
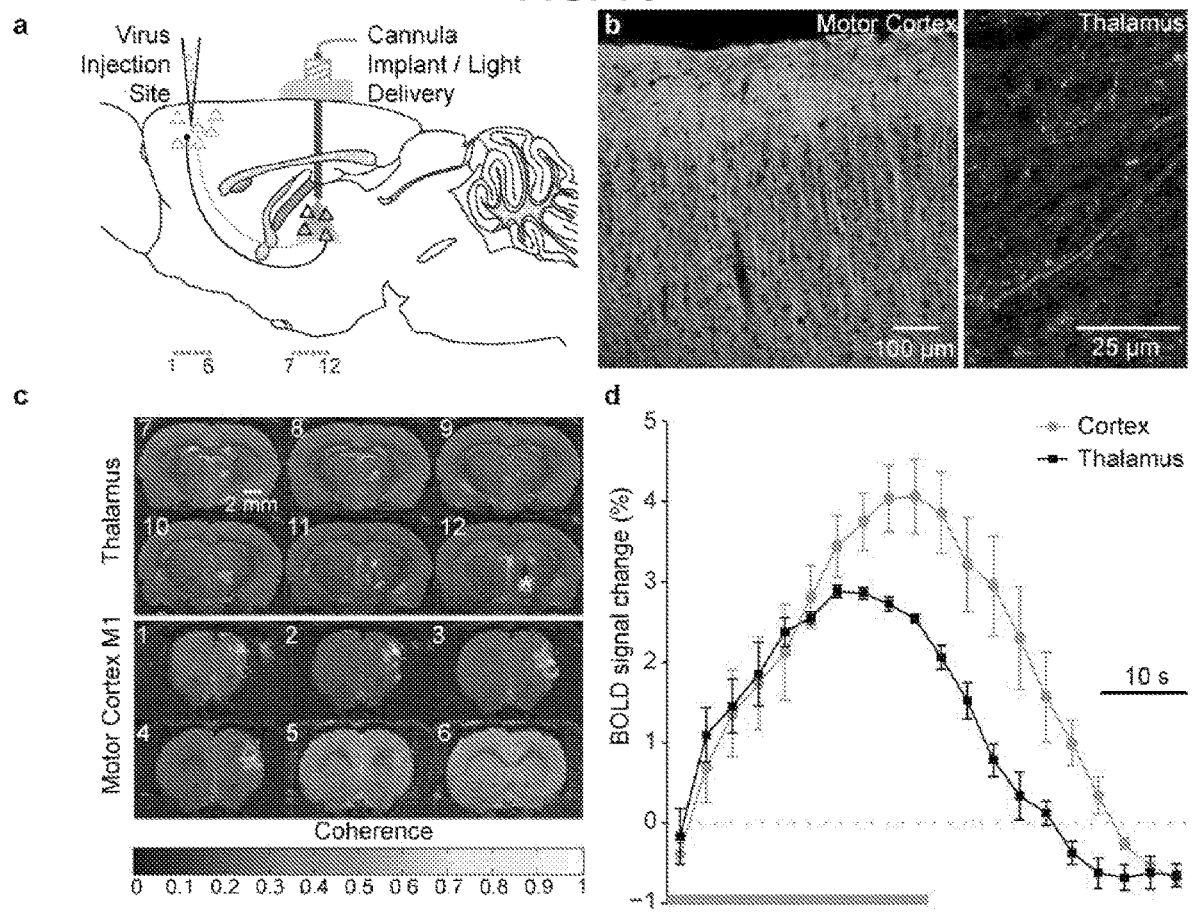

The ofMRI technology (FIG. 14 to FIG. 16), by combining optogenetic control with high-field fMRI, allows precise control of brain circuit elements and visualization of the resulting causal effects on the brain. In our initial study using ofMRI, brain circuit elements were successfully controlled and monitored based on their genetic identity, cell body location, and axonal projection target. Selective excitation of excitatory neurons with cell bodies in M1 cortex of rat resulted in robust activity measurement in local cortex (FIG. 14), distal areas including striatum, and thalamus (FIG. 15). It was also demonstrated that the neural activity is more accurately mapped throughout the brain in striatum and thalamus using the passband bSSFP fMRI technique (described in next paragraph) compared to the conventional GRE-BOLD fMRI technique (FIG. 15). The temporal dynamics of the fMRI signal also were shown to have strong correlations with the electrophysiological measurements with high temporal resolution, indicating that the fMRI hemodynamic response accurately reflects the temporal neural activity pattern. Targeting excitatory neurons in anterior and posterior thalamus also demonstrated robust local and long-range activity consistent with the existing literature regarding network connectivity of each region. In addition, selective excitation of axonal fibers projecting from M1 cortex showed that wiring patterns in addition to genetic identity can be used to selectively target and monitor the brain (FIG. 16). These findings demonstrate that ofMRI defines a potent tool that is suitable for functional circuit analysis as well as global phenotyping of dysfunctional circuitry.

Passband b-SSFP fMRI is a novel fMRI method that utilizes rapid radiofrequency excitation pulses combined with fully-balanced gradient pulses during each excitation repetition interval ($T_R$). Due to its short readout time and $T_R$, b-SSFP provides distortion-free 3D imaging suitable for full-brain, high-resolution functional imaging (FIG. 16). While the conventional fMRI is a highly successful technique that provides a non-invasive means to study the whole brain including deep-brain structures, it has significant limitations for the accurate assessment of neural function in its current form. Due to large spatial distortions, large portions of the brain cannot be imaged. Spatial resolution also needs significant improvement to provide information necessary for the state-of-the art neuroscience. Passband b-SSFP fMRI, by providing a way to obtain distortion-free 3D isotropic resolution images, greatly enhances the yield of fMRI for certain key questions.

Figure 17:
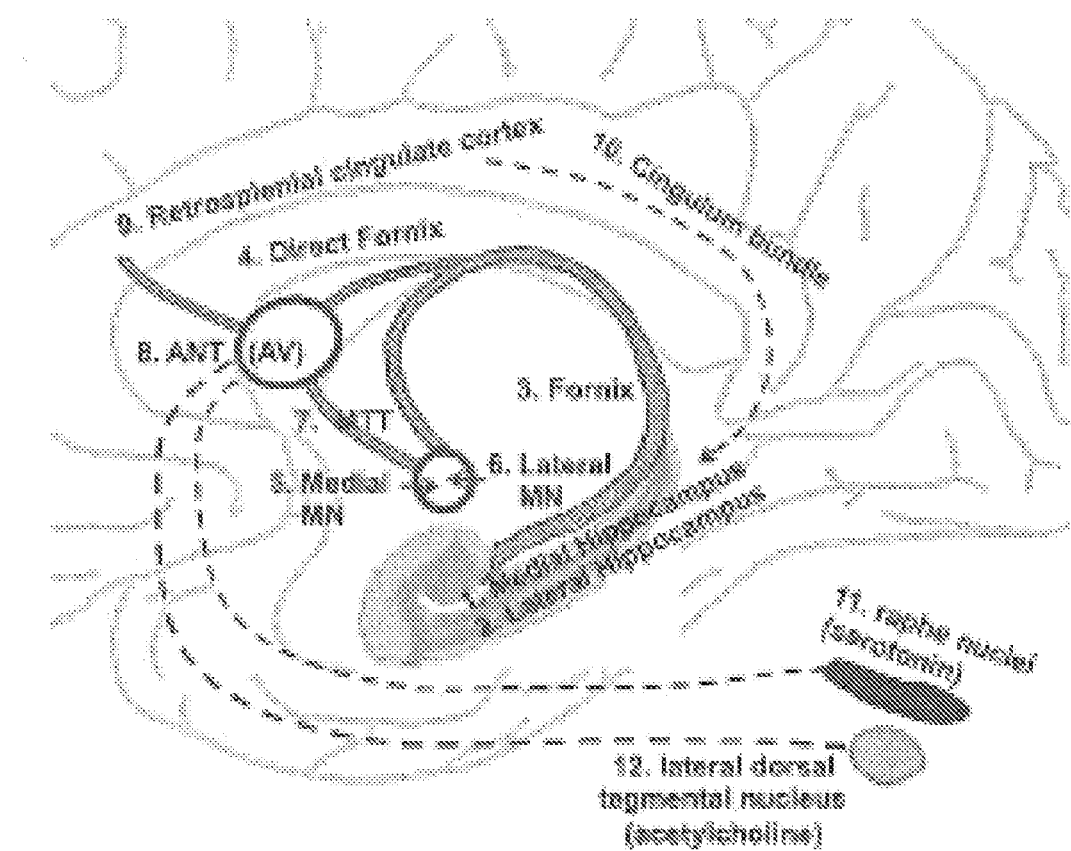
FIG. 17 illustrates Circuit of Papez, relevant to hippocampal seizure propagation. Medial (1) and -lateral (2) hippocampus gather outflow in fornix (3), among other efferents not depicted. Fornix (3) connects with the mammillary bodies of the posterior hypothalamus, and a direct fornix connection (4) synapses in the anteroventral nucleus of the anterior nucleus of thalamus (8). The mammillary bodies have medial (5) and lateral (6) nuclear groups. Mammillary bodies project via the MTT (7) to the ANT (8), which in turn projects to retrospenial cingulate cortex (9). The cingulum bundle (10) completes the loop back to subiculum and hippocampus.
Figure 18:
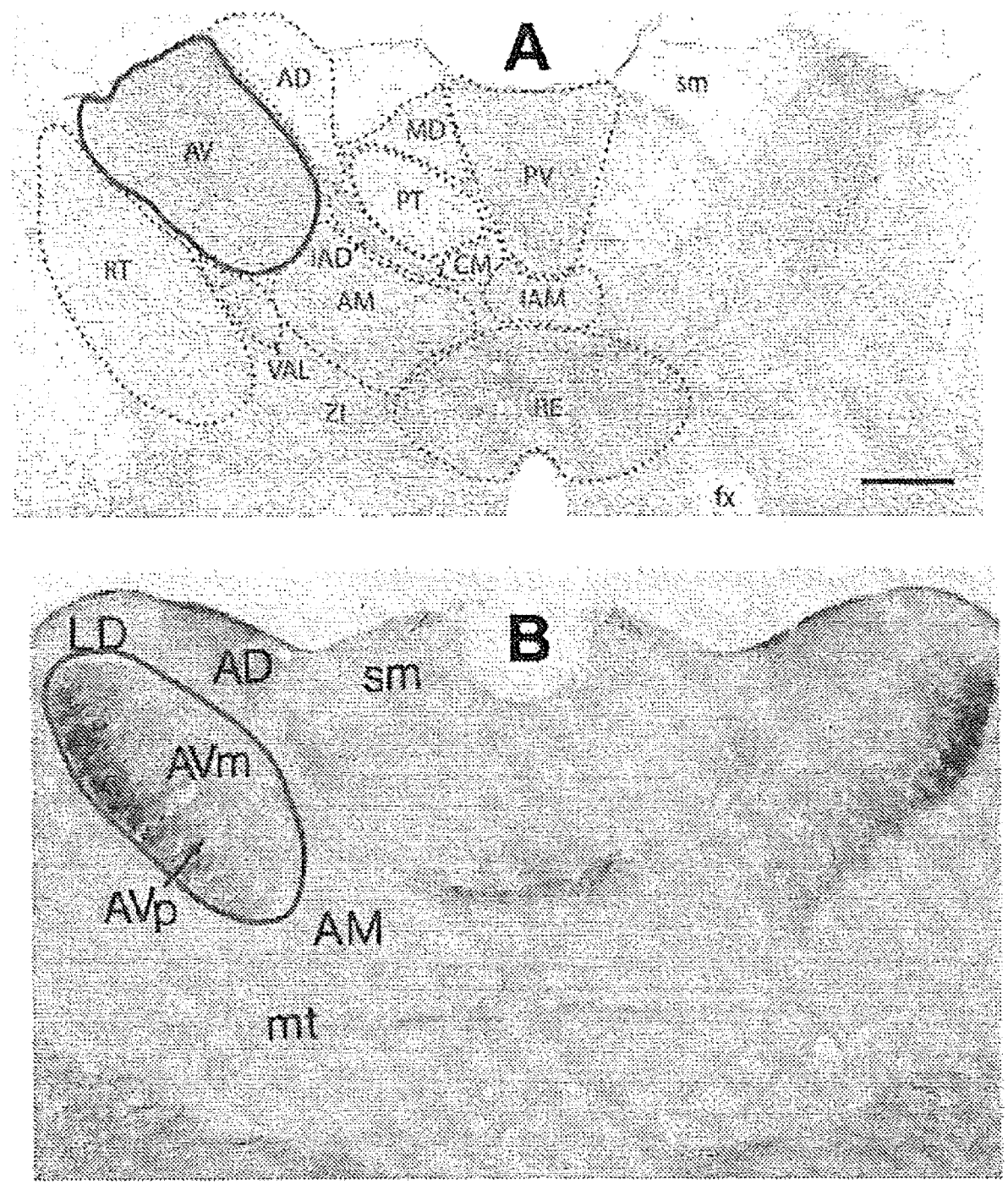
FIG. 18a and FIG. 18b illustrate aerotonergic and cholinergic projections to ANT (AV).

Anatomy of seizure spread from mesial temporal regions: In Aim. 1 below, the brain regions activated by precisely generated seizures in medial and lateral hippocampus may be visualized. The so-called Circuit of Papez may be activated. FIG. 17 depicts the main (although not the only) propagation pathway via the Circuit of Papez for seizures originating in the mesial temporal region. Complex partial and secondarily generalized seizures originating from the mesial temporal region comprise the most prevalent refractory seizures among adults with epilepsy. Hippocampal outflow from region CA1 gathers in fimbria and fornix (#3 in FIG. 17). The fornix provides input to the medial (#5) and lateral (#6) regions of the mammillary bodies in posterior hypothalamus. The lateral mammillary nuclei projects bilaterally to both anterodorsal portions of ANT; while, the medial mammillary nuclei project only ipsilaterally to anteroventral and anteromedial portions. Cutting the mammillothalamic tract (MTT) can increase threshold for PTZ-induced seizures. Conversely, electrically stimulating mammillary bodies in rats and patients inhibits seizures. In addition, fornix sends a retro-commissural branch directly to the anterior nucleus of thalamus (ANT, #8).

The anteroventral (AV) subgroup of ANT is the primary nucleus in this group of nuclei and animal literature usually defaults to the term anteroventral (AV) thalamus, unless specifically referring to the anteromedial or anterodorsal nuclei of ANT. ANT holds special significance as the only specific brain region proven effective in a large controlled clinical trial as a target of electrostimulation for epilepsy. Hippocampal outflow also flows to ANT via the MTT (#7). Other important inputs to AV come from the reticular thalamus, terminating on small-to-medium size synapses, cingulate cortex and brainstem.

ANT output is mainly to retrosplenial cortex, which is part of the cingulate gyms (#9), representing Brodmann's areas 26, 29 and 30. AV additionally projects to the septal part of the subiculum, postsubiculum, presubiculum, parasubiculum and to caudal entorhinal cortex. Cingulate cortex projects back to subiculum and hippocampus, completing the Circuit of Papez loop. In aim 2 below, seizure propagation and development may be inhibited by using optogenetic techniques at the waystations and subregions (e.g., medial and lateral mammillary body, direct fornix tract to ANT, and cell bodies in ANT) of the Papez system.

Neurotransmitter systems. Manipulation of neurotransmitter systems is another way to modulate the therapeutic effects of electrical stimulation. Traditional studies elucidate the role of neurotransmitter systems in therapeutic actions of drugs or devices by use of pharmacological blockade. Neurotransmitter antagonists have varying degrees of specificity and blockade almost always produces effects outside the system of interest. Optogenetic techniques allow inactivation or excitation of neurotransmitter systems in a specific pathway of interest. This approach will more usefully inform design of targeted stimulation therapies. Secondary benefit may accrue to drug design.

The AV nucleus of ANT is the most heavily labeled of any thalamic nuclei with markers of serotonin terminals from midline raphe. According to prior studies, elevating serotonin in AV of the rat inhibits seizures produced by the convulsant drug, PTZ. Conversely, the beneficial effect of ANT electrical stimulation to raise threshold for PTZ seizures, are largely blocked by the serotonin antagonist, methylsergide. Cholinergic fibers travel to AV from two cholinergic cell groups of the mesopontine tegmentum, mainly the laterodorsal tegmental nucleus, and to a lesser extent, the pedunculopontine tegmental nucleus. These ascending cholinergic afferents to AV can modulate excitatory inputs from mammillary bodies and cortex. AV participates in an input-output loop with retrosplenial cingulate cortex, using glutamatergic fibers to AV that predominantly innervate distal dendrites of thalamocortical projection neurons. About 12% of axon terminals in AV are positive for GABA markers, and these terminals may arise in reticular thalamus, basal forebrain or brainstem. These synapses are symmetric and form on dendrites and cell bodies. There is debate about whether AV contains GABAergic interneurons, but none were identified in one recent study.

Contribution of optogenetics: One likely reason for limited and variable success in stimulating ANT for epilepsy is the complexity of the nucleus. As the summary background on ANT anatomy above indicates, a variety of inputs, outputs, magnocellular and parvicellular portions of ANT, numerous neurotransmitter systems, ipsilateral and bilateral pathways all will influence the manifestations of anterior thalamic electrical stimulation. Optogenetic techniques are ideally suited to dissect out the important components of a therapeutic response to stimulation. Doing so will guide future work with more precisely targeted electrical stimulation. For example, finite element modeling of DBS effects in three dimensions demonstrates excitatory effects near the electrode for synapses and fibers of passage, with cell bodies having higher thresholds for firing. Therefore, if certain fiber systems in ANT were found to be of key importance, stimulation could be designed to preferentially activate those systems. Knowledge of important subpopulations also could help to minimize side effects of stimulation. Memory impairment was reported by patients receiving stimulation in the clinical trial of ANT stimulation for epilepsy. With tailored stimuli, guided by knowledge from optogenetic studies, cell soma inactivation, believed to be involved in memory impairments might be spared.

In this proposal, merger of the novel ofMRI technology with stimulation and seizure models will provide a groundbreaking opportunity to clarify potential mechanisms of seizure control by electrical and optogenetic stimulation. The description below will be divided into three parts according to the three specific aims this project proposes to achieve.

Aim 1. Optogenically induce seizures with precision of seizure origin and onset time: Seizures will be generated by optogenetically stimulating pyramidal neurons, without incurring direct stimulation of inhibitory interneurons or fibers of passage, in medial and lateral CA1. Seizures will then be tracked through linked brain networks with ofMRI. The neurophysiological basis of ofMRI signal will be investigated with measurements of local field potentials and single unit recordings at the location of ofMRI activity. The seizure model will also be validated by blinded comparisons of EEG and video-recorded animal behavior. The advantage of using this seizure model over other conventional seizure models made by chemical or electrical manipulations lies in knowledge of specific cells of origin, and ability to quickly and repeatedly generate a seizure with pulses of light. The three hypotheses to be tested in this section are: a, Optogenetic stimulation of pyramidal neurons in the hippocampus will lead to initiation of seizures comparable to those seen with conventional models of mesial temporal seizures. b, The seizures will depend on parameters of stimulation frequency, and specific location of stimulation within the hippocampus. c, Optogenetically generated hippocampal seizures produced by activation of selected cell populations will propagate to other brain structures in a repeatable, defined fashion.

Proposed Model: In order to initiate seizures, pyramidal neurons will be optogenetically stimulated in medial and lateral CA1, which is immediately connected with the outflow of hippocampus to the Circuit of Papez. Since CA1 is a large structure with potentially heterogeneous connections the brain network, medial and lateral locations will be selected for comparison. The stimulation will be applied at 1, 10, 60, 100 pulses per second. Based upon our preliminary experiments, distinct seizure responses depending on stimulation location and frequency are expected. With the optogenetics approach, our goal is to obtain unprecedented precise, reversible onset of seizures. Such precise seizure generation combined with ofMRI can potentially enable a groundbreaking ability to monitor seizure propagation within the intact whole brain network in vivo. This will help us characterize seizures and design strategies to inhibit them.

Selective Optogenetic Stimulation: Throughout this project, to specifically stimulate and inhibit pyramidal neurons, AAV5-CamKIIa-ChR2-EYFP and/or AAV5-CamKIIa-NpHR-mCherry will be injected. AAV5, since it generates anterograde labeling, will selectively target neurons with cell bodies at the site of injection. CamKIIa promoter is used to produce ChR2 or NpHR only in pyramidal neurons while EYFP and/or mCherry will be used to co-localize ChR2 and NpHR expression for validation. After recovery from surgery for injection of the virus and optical guide implantation, blue and/or yellow light will be used to optogenetically trigger the neurons. For selective stimulation of serotonergic and cholinergic neurons, TPH2-ChR2 and ChaT-ChR2 transgenic mice will be used, with serotonergic and cholinergic neurons selectively expressing ChR2. Surgery on the transgenic mice will comprise only implantation of an optical guide to deliver blue light stimulation. In aim 1, our goal is to generate a model of epilepsy by stimulating pyramidal neurons in CA1. However, in order to also facilitate different types of neuron targeting in aim 2 and 3, AAV5-CamKIIa-ChR2-EYFP will be injected in CA1 of normal rats as well as HP2-ChR2 and Chat-ChR2 transgenic mice.

ofMRI: With the precise temporal control of optogenetics, stimulation can be applied periodically, enabling ofMRI scans to monitor the resulting brain network activity. Blue light will be delivered in 1, 10, 60, 100 cycles per sec for 20 s every 1 min for a total of 6 min while scanning the whole brain. A 7-T-Bruker small animal dedicated MRI system will be used. Animal will be placed within a custom-designed stereotaxic cradle while intubated, ventilated with light isofluorane anesthesia (~1.3%). Images are continuously acquired at 1.34 frames per second with 0.5 mm isotropic resolution while covering the whole brain.

Figure 19:
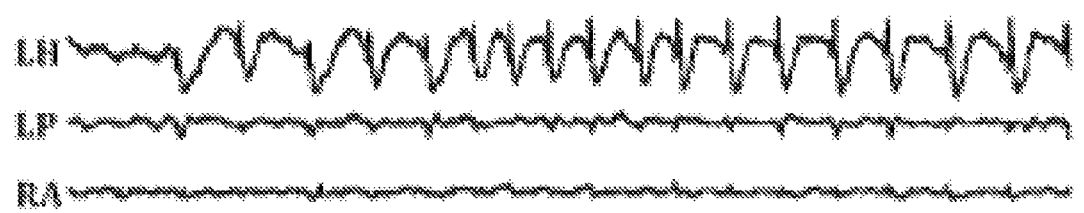
FIG. 19 illustrates focal seizure in the left hippocampus of a rat, produced by injecting bicuculline into hippocampus. Spike-waves are visible in the hippocampal electrode.

EEG and behavior: After ofMRI studies, for validation as a seizure model, behavioral studies will be conducted while recording EEG in the hippocampus and the skull surface. After ofMRI studies are finished, animals will undergo additional surgeries for EEG electrode implantation. After animals recover from the surgery, animals will be acclimated to a diamond-shaped box with no distracting stimuli. The shape cuts down on corners and helps to visualize the animal head-on. Animal will receive a banana piece between trials. Recordings are performed for 5 min of baseline, followed by 20 s of optogenetic light stimulation at 5, 10, and 15 minutes (4:20 of no stimulation recording in between) The experiment lasts 20 min. With 1 hour rest intervals, different parameters of stimulation frequency will also be tested in randomized order. Tests will be repeated twice for each animal. During the stimulation, videos will be recorded along with EEG recordings. The seizure model will be validated by blindly comparing digitally-clipped EEG segments and videos of rat behavior. Samples. will be taken for periods of no known seizure (rest, sleep, active exploration, feeding, sniffing), seizures from optogenetic stimulation and seizures from cannula injection of the GABA antagonist bicuculline methiodide (0.1 mM, 2 µL into left hippocampus at 2 mm to the left of the midline suture, 4 mm posterior to bregma, and 2.5 mm deep to the surface of cortex), according to the prior method of the co-investigator (FIG. 19). EEG's of clippings (without videos) (FIG. 19) of optogenetic stimulation, bicuculline injected animal, and intervening non-seizure times will be scored by two electroencephalographers unaware of treatment group. Each clip will be classified into one best category: 0=normal, 1=abnormal but no epileptiform activity, 2=interictal epileptiform activity, 3=ictal epileptiform activity. Video clippings from the same segments will be presented without EEGs and classified according to the Racine scale for seizures: 1=mouth and facial movements, 2=head nodding, 3=forelimb clonus, 4=rearing, 5=rearing and falling, a full motor seizure, with loss of postural control. Significances of differences among groups will be assessed by a nonparametric proportional difference test.

Local Field Potential (LFP) and Single Unit Recording: LFP and single unit recordings will be conducted at sites identified by ofMRI as active region to identify the underlying neural activity. Plexon 32 channel recording system with two silicon 16 channel probes will be used to record from multiple sites while stimulating. Acute recordings will be performed under isoflurane anesthesia. LFP and single unit will be recorded together at all times. Since these recordings will be conducted as a terminal procedure, this will be conducted after ofMRI, EEG and behavioral tests.

Figure 20:
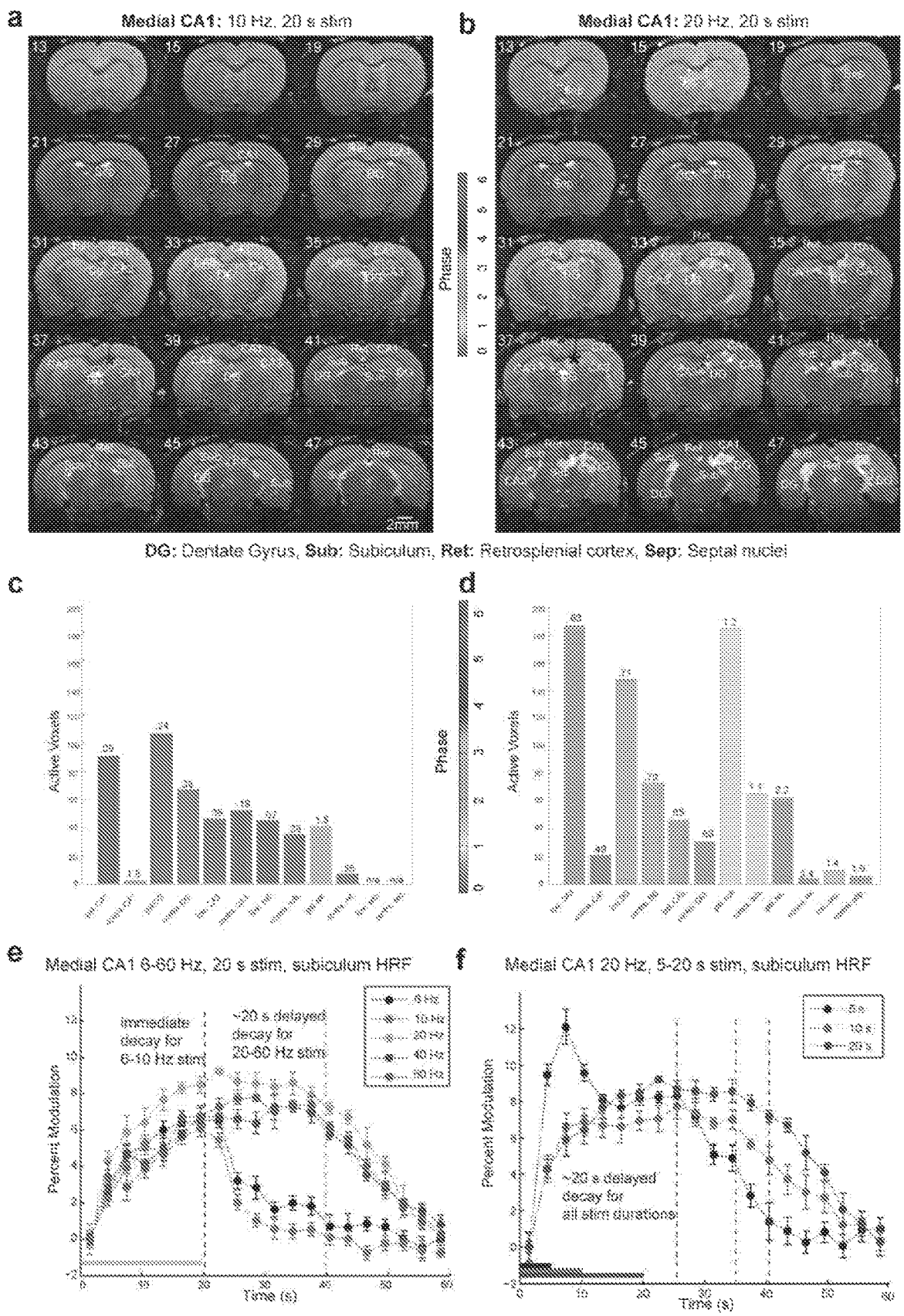

In our preliminary study, blue light was used to optogenetically trigger the neurons at 6, 10, 20, 40, and 60 cycles per sec for 20 s in 1 min interval for 6 minutes. Stimulation of pyramidal neurons in medial CA1 at low frequency (10 Hz) showed that activity spread to regions including parts of CA1, dentate gyrns (DG), CA3, subiculum, and the retrosplenial cortex (FIG. 20a). However, a striking difference was observed with stimulation at 20 Hz. A significantly larger area is recruited, now including the septal nuclei and larger portions of CA1, DG, CA3, subiculum, and the retrosplenial cortex (FIG. 20b). Further quantitative analysis of the spatial activation pattern was conducted by plotting the number of active voxels for each region. The color of the bar indicates average phase of the active voxels (FIG. 20c, d). This clearly demonstrates the significant increase in the active volume with 20 Hz stimulation compared to 10 Hz. In addition, all areas display significantly higher phase, especially in the subiculum. To investigate the source of the frequency-dependent phase, ofMRI-hemodynamic response function (HRF) was plotted at 6, 10, 20, 40, 60 Hz for the commonly active voxels in the subiculum (FIG. 20e). This shows a very clear trend in the HRF, where only above 20 Hz stimulation results in HRFs with approximately 20 s sustained high amplitude after the stimulation offset. Such sustained activity lasting for approximately 20 s was also found to be independent of the stimulation duration where 5, 10, 20 s stimulation all resulted in ~20 s sustained HRF (FIG. 20f).

Figure 21:
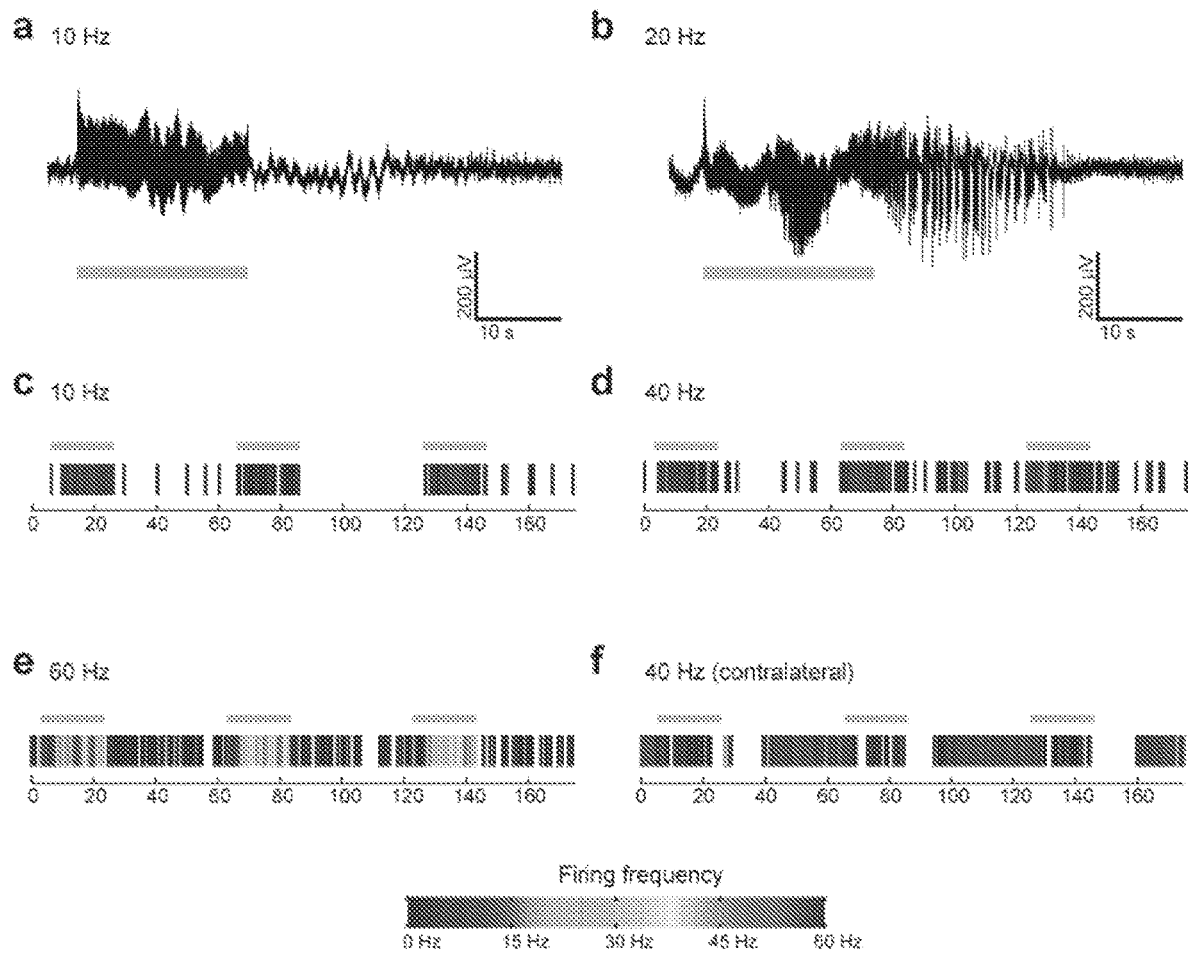

Such differences in HRF were also proven to be an accurate reflection of the underlying neural activity using local field potential (LFP) and single unit recordings (FIG. 21). LFP recorded with 10 Hz stimulation shows immediate decrease in neural activity after the stimulation offset (FIG. 21a) while 20 Hz stimulation shows sustained LFP signal for approximately 20 s after the stimulation stops (FIG. 21b), consistent with the ofMRI-HRF observations (FIG. 21e, f). Single unit recordings reveal similar trend where stimulation at rates above 20 Hz results in sustained neural spiking after the stimulation offset, while low frequency stimulation only gives spiking during stimulation (FIG. 21c-e). Interestingly, on the contralateral side, neurons that are inhibited as a result of the optical stimulation may also be observed. Furthermore, the inhibition lasted after the stimulation offset at high frequency stimulation (FIG. 21f).

These results suggest that above 20 Hz stimulation results in more effective generation of seizures, compared to 10 Hz.

To further explore location dependency, lateral CA1 was stimulated at high frequency (60 Hz). This resulted in a dramatically different activity pattern observed across the whole brain compared to the medial CA1 stimulation. Lateral CA1 optical stimulation activates the classical circuit of Papez (FIG. 17), invoking a pathway from hippocampus, to fornix, to mammillary bodies of hypothalamus, to anterior thalamus to cingulate cortex, to cingulum bundle, to entorhinal cortex and back to hippocampus (FIG. 21).

Preliminary behavioral studies with 40 s stimulation in the lateral CA1 (table below) show no, effect with sham stimulation at very low light power while sufficient light power stimulation at 10 Hz induces Racine stage 2 seizures. Stimulation at 20 and 40 Hz provokes Racine stage 5 seizures. This is in sharp contrast to the medial CA1 stimulation where only mild or Racine stage 1 behavior is observed for all frequencies (10, 20, 40 Hz). This is consistent with the ofMRI findings that show primarily local hippocampal regions recruited with the medial CA1 stimulation while the Circuit of Papez is recruited with lateral CA1 stimulation.

For this aim, 15 male Sprague-Dawley rats, 5 male TPH2-ChR2 and 5 male ChaT-ChR2 transgenic mice will be used. 5 rats each will be implanted and stimulated in medial and lateral CA1, and 5 rats will receive bicuculline methiodide injection. ofMRI will first be conducted for the 10 rats with CA1 optical guide implantation with stimulation frequency of 1, 10, 60, 100 cycles per sec. EEG and behavioral testing will be conducted in the 10 rats with optical guides in CA1 and the bicuculline injected rat for model validation. After this, the 10 rats that were subjected to ofMRI mapping will undergo LFP and single unit recording to identify the neurophysiological correlates of the ofMRI signal changes. TPH2-ChR2 and Chat-ChR2 mice will be then used to generate the proposed seizure model in mice with optimal seizure generation parameters as identified with rats, since the serotonergic and cholinergic optogenetic experiments of aim 2 can be performed only in mice. The mouse model will be validated in comparison to the rat model through ofMRI, EEG, and behavior. The preliminary data suggests that lateral CA1 stimulation with high frequency is the best candidate for generation of propagating seizures on demand.

Expected outcome: Optogenetic stimulation of hippocampal pyramidal cells will produce replicable and reliable seizures with a specific pattern of spread. Blinded evaluations of EEGs from non-seizure segments, seizures produced by a conventional convulsant (BMI) and optogenetic stimulation, will show the optogenetic seizure model to be quite comparable to the conventional model, but more experimentally controllable and interpretable.

Aim 2. Inhibiting Seizures with Cell-type Specific Neurostimulation. In this section, the optogenetically-induced hippocampal seizures may be tracked and the best optogenetic location and parameters to. inhibit the seizures may be determined. The effects of optogenetic inhibition with NpHR may be explored as well as disruptive excitation with ChR2. Disruptive excitatory optogenetic stimulation is to be tested, because it most closely approximates electrical stimulation, by desynchronizing and functionally inhibiting downstream structures. The hypotheses here are as follows: a, Neural inhibition with NpHR will block ofMRI, EEG, and behavioral evidence of hippocampal seizure spread to neocortex with different degrees of efficacy depending on the region of NpHR inhibition. b, Disruptive neural excitation with ChR2 will block ofMRI, EEG, and behavioral evidence of hippocampal seizure spread to neocortex with different degrees of efficacy depending on the region of ChR2 disruptive excitation and frequency of stimulation. c, Cell-type specific light-induced excitation of serotonergic and disruptive (inhibitory) excitation of cholinergic fibers in ANT will block ofMRI, EEG, and behavioral evidence of hippocampal seizure spread to neocortex. It this proves to be effective, combination DBS and drug therapy, for example, selective serotonin reuptake inhibitors can be considered.

For the study in aim 2, all animals will have AAV5-CamKIIa-ChR2-EYFP instilled in lateral CA1 along with an optical guide for blue light stimulation. Depending on the therapeutic target under investigation, they will have additional injections and/or probes at other locations. Unilateral optogenetic stimulation for therapeutic stimulation may be used, but if residual seizures are observed, then bilateral stimulation may be used. For the therapeutic inhibition and excitation of pyramidal neurons in aim 2 a and b, both AAV5-CamKIIa-ChR2-EYFP and AAV5-CamKIIa-NpHR-mCherry will be injected to our target regions. Our injection targets will include medial and lateral mammillary bodies, hippocampus (AP +5.3, DV +7.1, L ±0.7, relative to ear bars) where the fornix tract originates. By injecting anterograde virus into these regions and stimulating in AV, it may be possible to selectively inhibit or excite incoming fibers of specific anatomical origin. Injection in AV with AV stimulation will enable specific stimulation of pyramidal neurons with cell body in AV. The hypothesis is that selectively inactivating or disruptively stimulating one of these pathways will identify the generator of the anticonvulsant effect of electrical stimulation. To test the role of serotonergic and cholinergic projections to AV, the transgenic mice that have ChR2 expression specifically in serotonergic neurons and cholinergic neurons may be utilized. Based on prior studies, serotonergic neurons will be stimulated while cholinergic neurons will be disruptively stimulated (i.e. functionally inhibited) for therapeutic efficacy. For the total of 6 therapeutic groups, 5 animals each will be used.

Light stimulation will be tested with yellow light inhibition or blue light stimulation at 1, 10, 60, 100 pulses per second (only blue light for transgenic animals). Alternative opsins will be used to stimulate at frequencies greater than 100 Hz, if the trend is in favor of benefit from higher frequencies.

Optogenetic stimulation will be introduced in each experiment at two time points for 30 s: 10 s prior to initiation of a seizure and 10 seconds after termination of the 20-second-long stimulus used to generate the seizure. This will be repeated every 1 min for 6 min during ofMRI scans to obtain the global map of the seizure inhibition mechanism. In addition, EEG and behavioral test will be used to grade the efficacy of therapy. Tønnesen utilized inhibitory stimuli of 5-10 seconds in a hippocampal culture slice model. A sufficiently longer duration for the in vivo experiments may be chosen.

Expected outcome: It is expected that seizures generated in hippocampus will be inhibited—prevented, shortened or both—by optogenetic manipulations of the spread pathways. Both direct inhibition with NpHR and disruptive excitation with ChR2 will be effective. The degree of benefit will depend upon specific locations of stimulation as well as frequency and duration of optogenetic stimuli. Our experimental design starts without background assumptions about the Circuit of Papez. The circuit potentially is a conceptual oversimplification for seizure propagation, which can be improved by imaging the actual spread of a hippocampally-generated seizure. The feedback from the ofMRI data may be utilized to refine the search for an optimal target. The methods of the present invention may be one of the first in the field of epilepsy to distinguish anti-seizure effects of cell somas from fibers of passage.

Aim 3. Translate to Electrical Stimulation. In this section, electrical stimulation may be optimized to best imitate the beneficial optogenetic stimulation for more effective translation of the findings into clinical practice. The three hypotheses are as follows. a, Electrical stimulation of ANT at various amplitudes and frequencies while imaging with fMRI, monitoring behavior and EEG will reveal a characteristic pattern of electrical stimulation effects across the whole brain. b, By emulating the optimal optogenetic stimulation identified in aim 2 with electrical stimulation, seizures will be effectively inhibited for the optogenetic seizure model and for a generalized PTZ seizure model. c, Varying intervals of time between therapeutic electrical stimulation and an optogenetically-induced seizure, will disclose how long benefit of stimulation persists. This will greatly facilitate planning of clinical stimulation regimens.

First, in order to understand the global impact of electrical stimulation on brain, MR compatible platinum Teflon insulated wire electrodes (http://www.plastics1.com) may be implanted bilaterally in ANT of 5 male Sprague-Dawley rats. Then, the stimulation impact will be measured by fMRI with varying frequency and amplitude. The human clinical trial parameters of bipolar stimulation may begin at 145 Hz, 0.1 ms duration for 1-10 V in 1 V interval. The stimulation may be applied for 20 s in 1 min interval for 6 min. Earlier PET studies show that bilateral electrical stimulation in ANT increased glucose uptake in the target region, the thalamus and hippocampus, and decreased glucose uptake in the cingulate cortex and frontal cortex. This is a good indication that the impact of electrical stimulation involves these networks; however, studies with higher spatial resolution and temporal precision are necessary for our aims.

Based on the findings from the study above, a stimulating electrode will be placed in another set of 10 rats, and the stimulation intensity and frequency will be adjusted to most closely mimic the fMRI activation pattern produced by the optimal optogenetic stimulation for seizure inhibition as identified in aim 2. Electrical stimulation tailored to these parameters of location, frequency and intensity may inhibit seizures with a high degree of efficacy. This may be tested first in the optogenetic seizure model from aim 1 where the first 5 out of the 10 rats will have optogenetic stimulation cannula implanted in lateral CA1 in addition to the electrical stimulating electrode in thalamus. Clonic and tonic seizures produced by injection of the $GABA_A$ antagonist, PTZ, into a tail vein, a model previously employed by the co-investigator (FIG. 23), may be used to further test the findings in a generalized seizure model on the other 5 rats. For the optogenetic seizure model, fMRI, EEG, and behavioral tests will be conducted to measure the outcome of stimulation efficacy. fMRI will be conducted with 20 s optogenetic stimulation for epilepsy model generation every 1 min for 6 min while electrical stimulation is applied 10 s prior to the optogenetic stimulation onset for 30 s. For the PTZ model, continuous injection of PTZ as 20 mg/ml in saline will be infused at rates of 5.5 mg/kg/min by an infusion pump. Epileptiform EEG discharges usually begin by 5 minutes, with behavioral clonic seizures at about 10 minutes and tonic seizures soon thereafter. The time course can be compressed or expanded by adjusting dose infusion rate. Previously, electrical stimulation of ANT with 0.1-20 V (5-800 µA}, 100 µS bipolar pulses initiated before PTZ infusion has been shown to increase PTZ dose (infusion time) required to generate EEG or behavioral manifestations of seizures. A longer infusion time to first seizure (higher required dose of PTZ) represents an anticonvulsant action of stimulation. For this generalized seizure model, the stimulation efficacy will be measured by the PTZ dose.

Continuous electrical stimulation is commonly employed to treat movement disorders, but electrical stimulation to treat epilepsy has traditionally been done on a clock cycle, such as 1 minute on and 5 minutes off, because intermittent stimulation is believed to be less irritating to tissue and it preserves battery life. Rational determination of interval stimulation should depend upon the duration of a therapeutic effect after stimulation. A study of hippocampal penicillin-induced seizures in sheep showed spike-suppression for 1-2 minutes after 10 seconds of ANT stimulation. In accordance with the present invention, how long the anti-seizure effect endures after an electrical stimulation to ANT may be investigated by using the light-triggered hippocampal seizure model of aim 1. fMRI, behavioral testing and EEG may be employed to measure the impact of stimulation. While specific seizure onset time is controlled with optogenetic stimulation, the therapeutic electrical stimulation may start at 10, 5, 3, 1, 0 min before stimulation onset for 1 min. For the fMRI experiment, the 3 region of interests where therapeutic efficacy was best demonstrated in the aim 3b experiment will be selected and monitored for signal intensity change. To ensure high SNR, 8 measurements will be averaged. EEG and behavior will be assessed with the methods described in aim 1.

Expected Outcome: Electrical stimulation of ANT may show how electrical stimulation parameters change the functional output. With this knowledge, optimal optogenetic target identified in aim 2 may be effectively emulated with electrical stimulation leading to a promising treatment target. The experiments from the temporally precise seizure model from aim 1 may provide a proper systematic understanding of optimal timing for stimulus interval.

Facing the Challenges and the Risks: Potential Pitfalls and Expectations: The transformative research plans outlined above have inherent risks associated with the novelty of the approach. Potential pitfalls and back-up plans are outlined below.

Figure 24:
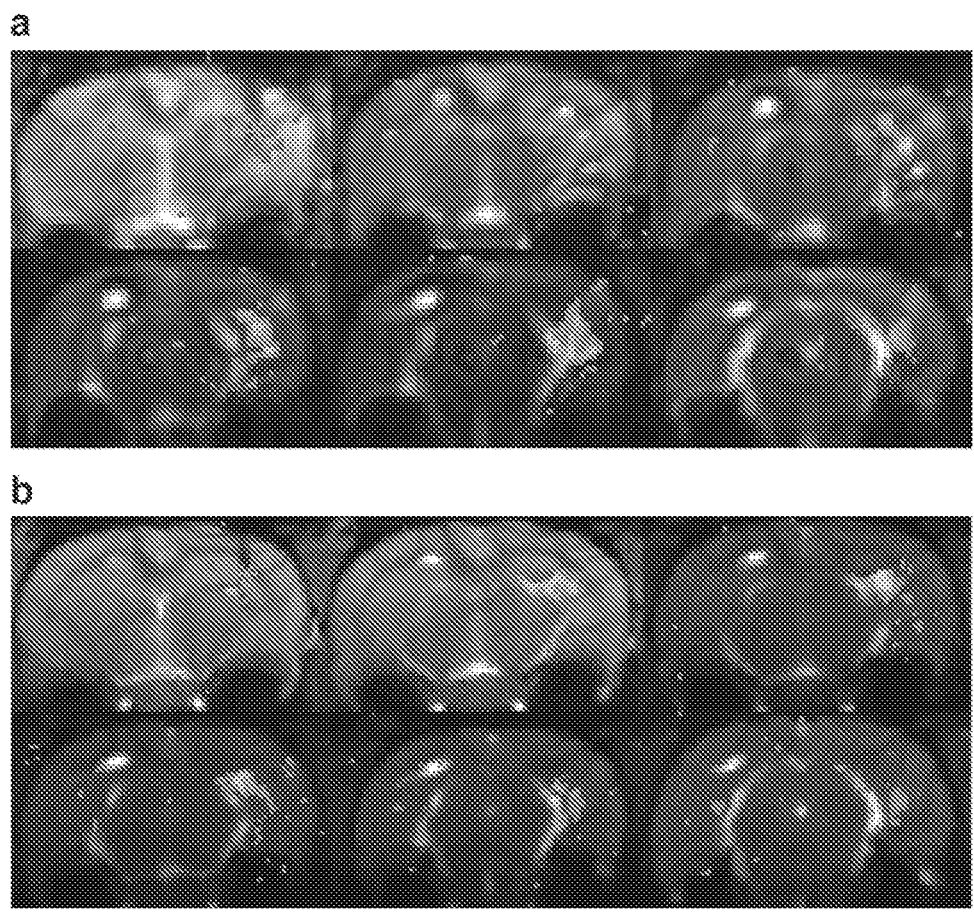
FIG. 24a and FIG. 24b illustrate compressed sensing passband b-SSFP fMRI.

High-Resolution, whole-brain ofMRI. MRI is conventionally limited in temporal and spatial resolution due to the Nyquist sampling rate requirements and serial sampling. To facilitate high-resolution spatial depiction of activity from small brain regions, compressed sensing algorithms were developed. Under-sampled, high-resolution acquisition trajectories were custom designed and compressed sensing reconstruction algorithms, obtaining approximately 6 times voxel volume reduction. In-plane resolution of isotropic 200 µm resolution and 1.3 frames per sec rate is achieved while covering the whole brain (FIG. 24). This unprecedented capability under development in the Lee Lab will further enhance accurate depiction of seizure activity and help our search for inhibition mechanisms.

Anesthesia and Seizures. All our imaging studies are to be conducted with isoflurane anesthesia. Isoflurane is known to inhibit neural activity, but our initial studies nevertheless showed good ofMRI, behavioral and cellular unit evidence of seizure activity. However, if seizures are excessively suppressed by anesthesia, the model starting in aim 1 may be revalidated using ketamine or enfluorane anesthesia, which are known to have less suppressive effect on EEG activation and seizure activity.

Seizure models. Clinical epilepsy is heterogeneous, and no single animal model perfectly models even one of the subtypes of clinical epilepsy. Various aspects of the present invention propose using three models: one novel and produced by hippocampal optogenetic stimulation, a second standard focal seizure model with bicuculline methiodide injected into hippocampus, and a third standard PTZ model of generalized seizures. Various aspects of the present invention study certain types of seizures, and not the global clinical entity of epilepsy, with spontaneously recurrent seizures. It is our belief that starting with these simple models will document the value of optogenetics in making epilepsy therapies more specific and effective. Lessons can then be validated in other models and eventually at the bedside.

Figure 22:
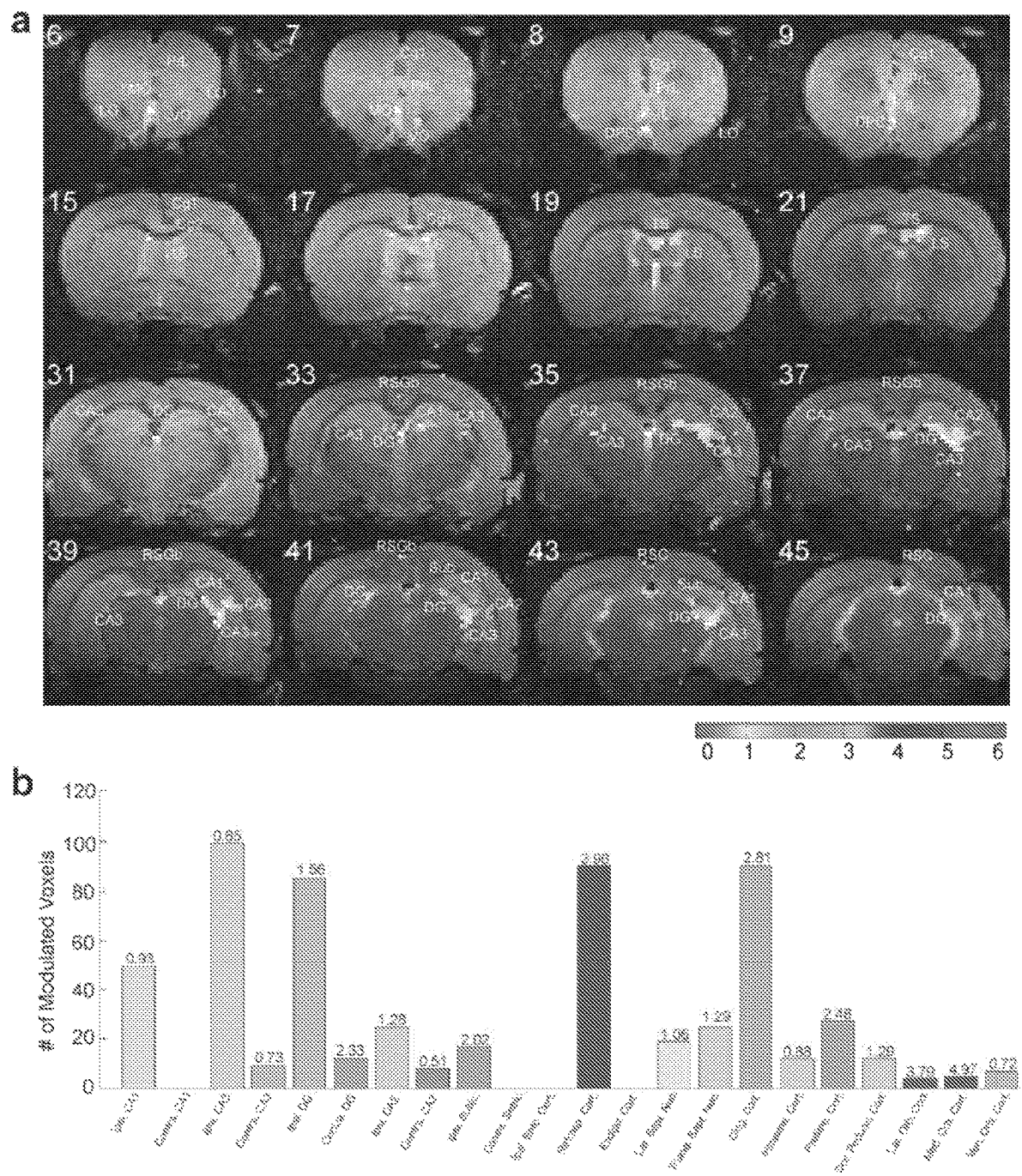
FIG. 22a and FIG. 22b illustrate Pyramidal neuron stimulation in the lateral CA1 recruits the circuit of Papez.

Ancillary pathways of propagation. The Circuit of Papez is not the only outflow tract of hippocampus, which also has efferents via the hippocampal commissures (psalterium) and entorhinal cortex. It is possible that these ancillary pathways might permit seizure spread even when the Papez route is inhibited. It is not known that stimulation of mammillary bodies and anterior thalamus in animals and humans can reduce seizures (FIG. 23) and preliminary data show activation of the Papez circuit (FIG. 22), however, it cannot be ruled out other paths as reasons for incomplete efficacy of ANT stimulation. An important advantage of ofMRI is the ability to directly observe and identify brain regions activated outside the Circuit of Papez. If seen, experiments may be modified to include the observed pathways.

Expectations: Various aspects of the present invention may change the way that clinicians design clinical trials for neurostimulation, not just for epilepsy, but for a variety of neurological and neurosurgical diseases. The platform and methodology of the present invention may reduce much of the guesswork about targets and parameters of stimulation, because optogenetic techniques are much more regionally and cell-type specific and controllable than are electrical stimulation techniques. Solid laboratory work should precede clinical application; this has too rarely been the case in the field of neurostimulation. Our project should be a strong step towards putting trial design for neurostimulation on a rational foundation.

4. Appropriateness for the Transformative Research Projects Program: Neurostimulation is an important area emerging as a useful new therapy for intractable neurological diseases. However, treatment efforts so far have been on an empirical basis, and not fully effective. Simple parameter changes or slight changes of stimulation targets can obliterate a beneficial effect or even make symptoms worse. Since implantation of stimulators is invasive, maximal efficacy is. required. In accordance with the present invention, neurostimulation may be transformed by establishing a new platform to systematically test each neural network elements' contribution to the therapeutic outcome. Epilepsy is to be a first testing ground, but lessons learned will apply to many other diseases potentially ameliorated by neurostimulation. This project will provide. the first development of an epilepsy model that can be rapidly triggered and terminated and that arises from a specific population of neurons. Visualization of the network activated by seizures from medial and lateral hippocampus will be a novel addition to our knowledge of functional seizure anatomy. These experiments will provide the first demonstration of interrupting seizure spread through a defined propagation pathway by use of optogenetic inhibition. Studies of how long an electrical stimulation inhibits seizures after the pulse ends will provide one of the first guides to rational timing of clinical stimulation. The key strategy is to use the precision and replicability of optogenetic techniques to identify the crucial components of a beneficial response to electrical stimulation. Someday, optogenetic neuromodulation may in itself be a useful clinical tool, but for now it is best used as a sharp scalpel to dissect the components of electrical stimulation. Our preliminary results are promising, yet the goals outlined in this proposal are ambitious, spanning molecular and cellular biology, genetics, physics, engineering, neuroanatomy and clinical neurology. This is a project with high potential impact and high risk. The transformative research program is ideally suited to fund such a project, and thereby to bring science closer to the bedside.

5. Exemplary Timeline: In the first year, an optogenetic model of seizures may be generated as outlined in aim 1. Twenty rats may be used to generate a rat model of seizure. In year 2, the same experiments may be repeated for twenty transgenic mice for aim 1. In addition, in year 2, efforts may begin to inhibit seizures by inhibiting pyramidal neurons in the circuit of Papez and inputs to ANT for the rat optogenetic seizure model. In year 3, disruptive stimulation will be applied to the pyramidal neurons. In the same year, experiments may be conducted where electrical stimulation is applied to ANT of rats while imaging, behavior, and EEG are conducted to evaluate the impact of electrical stimulation. In year 4, the optogenetic seizure model of mouse developed in year 2 will be utilized where serotonergic and cholinergic population will be modulated to study their anti-seizure effects. In the same year, emulating the optimal optogenetic anti-seizure effects with electrical stimulation may commence. First the optogenetic modeling of seizures may begin, and then also evaluate the effect in the general seizure model. In the last year, the stimulation duration effects will be evaluated.

Example D

Background Describing Approach to Treatment

An important challenge in drug development for epilepsy, as well as many other neurological diseases, is the accurate pre-clinical predictability of the future clinical efficacy and side effects of the compound. The complexity of the neurological system makes it extremely difficult to infer impact of a candidate compound using surrogate in vitro information, ex vivo data, or simple animal behavior models. Without precise a priori knowledge of disease mechanisms, it is difficult to generate disease models that can be used to accurately test drug efficacy. Our proposal aims to fundamentally transform this process through accurate disease model generation along with in vivo full brain quantification of the drug administration impact utilizing the optogenetic functional magnetic resonance imaging (ofMRI) technology. ofMRI is a novel technology combining a cell-type-specific, temporally precise stimulation method called optogenetics with fMRI readouts. The first proof of concept study published by the PI (Nature 2010) demonstrated ofMRI technology's ability to accurately visualize brain-wide neural activity resulting from cell types specified by its genetic identity, cell body location, axonal projection target, and temporal signaling patterns.

Using optogenetics, the PI's lab has data showing that a wide array of seizure activity can be repeatedly and reliably generated. Unlike seizure models generated with electrical shock, chemical injections, kindling, inbreeding of genetic strains, or physical trauma, precise knowledge of the original cell type, location, and time of seizure onset may be determined.

Furthermore, through ofMRI readouts, exact pathways of how neural signaling propagates through the network to create the observed mild partial seizures or full secondarily generalized tonic-clonic seizures can precisely be visualized. Instead of relying on EEG recordings at very limited numbers of brain locations (with deep locations requiring invasive electrodes) or Racine scales that show only coarse behaviors, ofMRI can demonstrate a whole brain therapeutic impact in live, behaving animals. The in vivo nature of the technology also enables longitudinal tracking of the disease where a single animal can be used to track how different doses and course of treatment impacts the animal over time. This is in contrast with conventional ex vivo technology that relies on sacrificing a large number of animals at different time points, thereby increasing variance, cost, and time.

With ofMRI's ability to generate and visualize the seizure network with unprecedented precision, a platform for quantitative anticonvulsant drug screening may be established. While observing the network engagement during a precisely generated seizure, we will administer several commercial drugs with relatively well-known, distinct efficacy and side effect profiles. We aim to demonstrate ofMRI-based observation of seizure inhibition by these known drugs. The inhibition could be fully or partially effective and we will be able to directly observe locations of the decreased or increased activity in live animal brains. In future work, we will further investigate ofMRI's ability to predict neurological side effects of a drug by highlighting patterns of activation and inactivation of certain areas of brain (for example, cerebellar inactivation as a marker for ataxia). Once ofMRI in the optogenetically-generated seizure model is validated for these three known AEDs, we will be in a better position to develop the system as a screen for putative new AEDs.

Procedures.

Three commercially available antiepileptic drugs (AEDs): phenytoin (PHT), lorazepam, and levetiracetam (LEV) may be used. They were chosen for their distinct preclinical anticonvulsant effects and distinct drug action mechanisms. In addition, they exhibit different profiles of efficacy in common epilepsy models, such as maximal electroshock (MES), systemic pentylenetetrazol (PTZ) and amygdala-kindling. PHT affects the refractory period of Na+ channels, lorazepam GABAergic efficiency and LEV a novel presynaptic A2 protein. Lorazepam shows efficacy in all three conventional models; whereas, LEV showed efficacy only in amygdala-kindling. Clinically, PHT and lorazepam show efficacy in partial and generalized tonic-clonic seizures, while LEV shows efficacy for partial, tonic-clonic and non-convulsive generalized seizures. Different drugs show clear differences in efficacy on different animal models, but clinical efficacy is not necessarily predicted by the animal model studies. Furthermore, if only MES and PTZ models were used, LEV would likely never have made it to the clinic. Therefore, utilizing proper animal models that represent the target epilepsy patient group that can provide predictability into the clinic is of great importance. For this, we need to have accurate understanding of the seizure that the animal model provides as well as a comprehensive readout on what the drug impacts in the animal model.

The animal models and their seizures are conventionally evaluated and categorized by videos of behavior and EEG recorded via bone screws. During evaluation, numbers grading the seizures based on pre-defined patterns are generated. For example, video clippings are classified according to the modified Racine scale (Dr. Fisher) for seizures: 0=normal, A=arrest of activity, 1=mouth and facial movements, 2=head nodding, 3=forelimb clonus, 4=rearing, S=rearing and falling, a full motor seizure, with loss of postural control. EEG are classified into one best category: 0=normal, 1=abnormal but no epileptiform activity, 2=interictal epileptiform (spikes) activity, 3=ictal epileptiform (EEG seizures or spike waves) activity.

However, such classifications are often not sufficient to fully characterize the seizures. It shows severity of the seizures on a linear scale but does not elucidate, for example, how different brain regions are involved, potentially missing the subtle differences associated with distinct seizure mechanisms and treatment options. Where and how the seizures originate and where they propagate to are important questions in designing treatment, especially considering the great amount of heterogeneity in epilepsy. Having a model with precise knowledge of the seizure origin, the ability to track the seizure propagation, therefore will transform how AEDs are developed.

Figure 26:
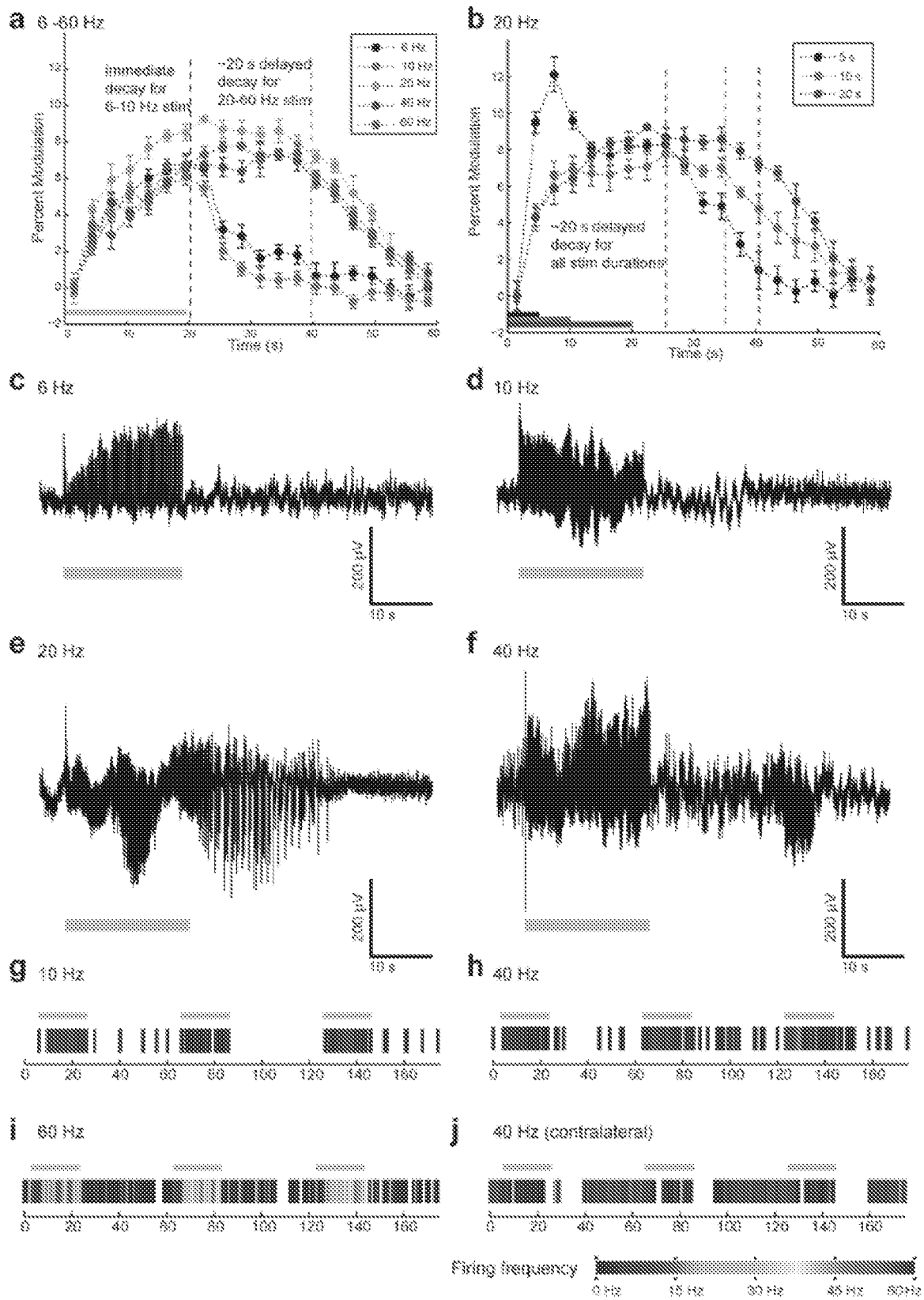
FIG. 26a, FIG. 26b, FIG. 26c, FIG. 26d, FIG. 26e, FIG. 26f, FIG. 26g, FIG. 26h, FIG. 26i and FIG. 26j illustrate electrophysiological recordings at ofMRI activity sites that show accurate spatio-temporal measurement capabilities of ofMRI.
Figure 27:
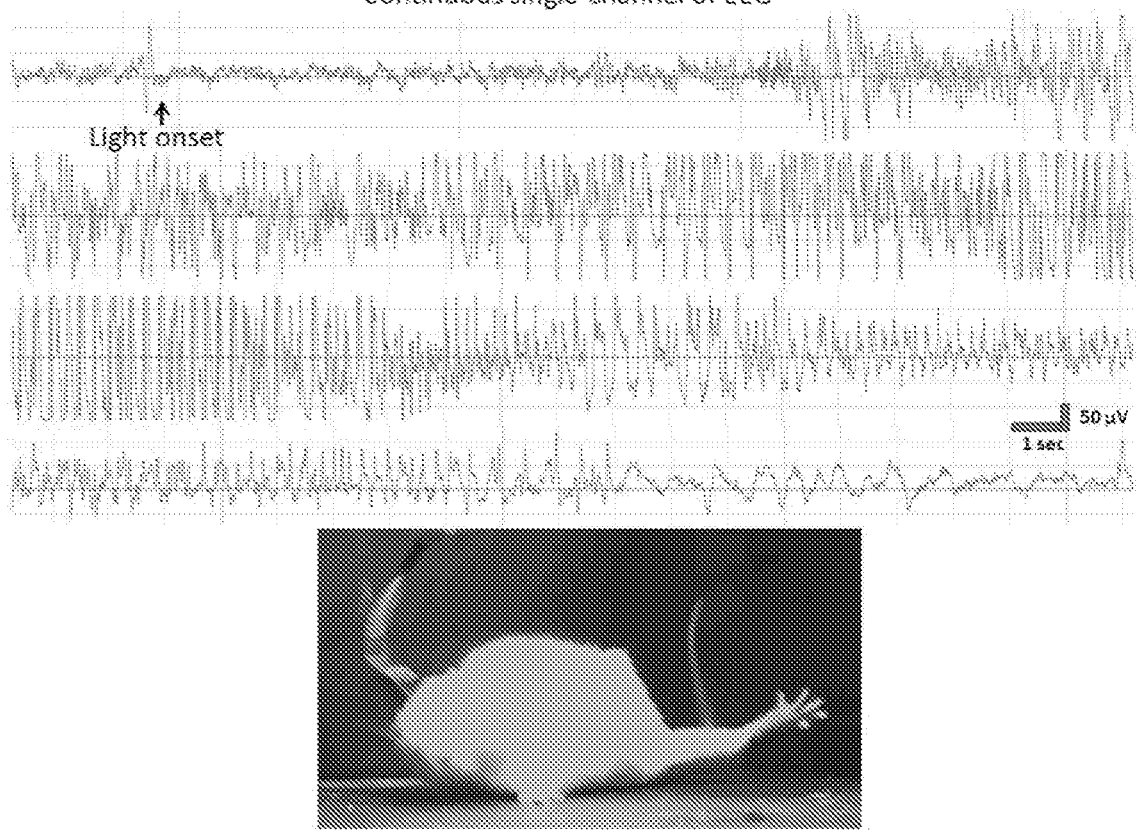
FIG. 27 illustrates EEG and behavior during optogenetic stimulation of dorsa-medial CA1. The top 4 traces show continuous EEG briefly before, during and after optogenetic light stimulation of transfected hippocampus. Light stimulation was applied at "light onset" time marked with a black arrow and lasted for 40 s. The overall trace shows 80 s of EEG recording. The bottom image shows a screen shot of the video during seizure.
Figure 28:
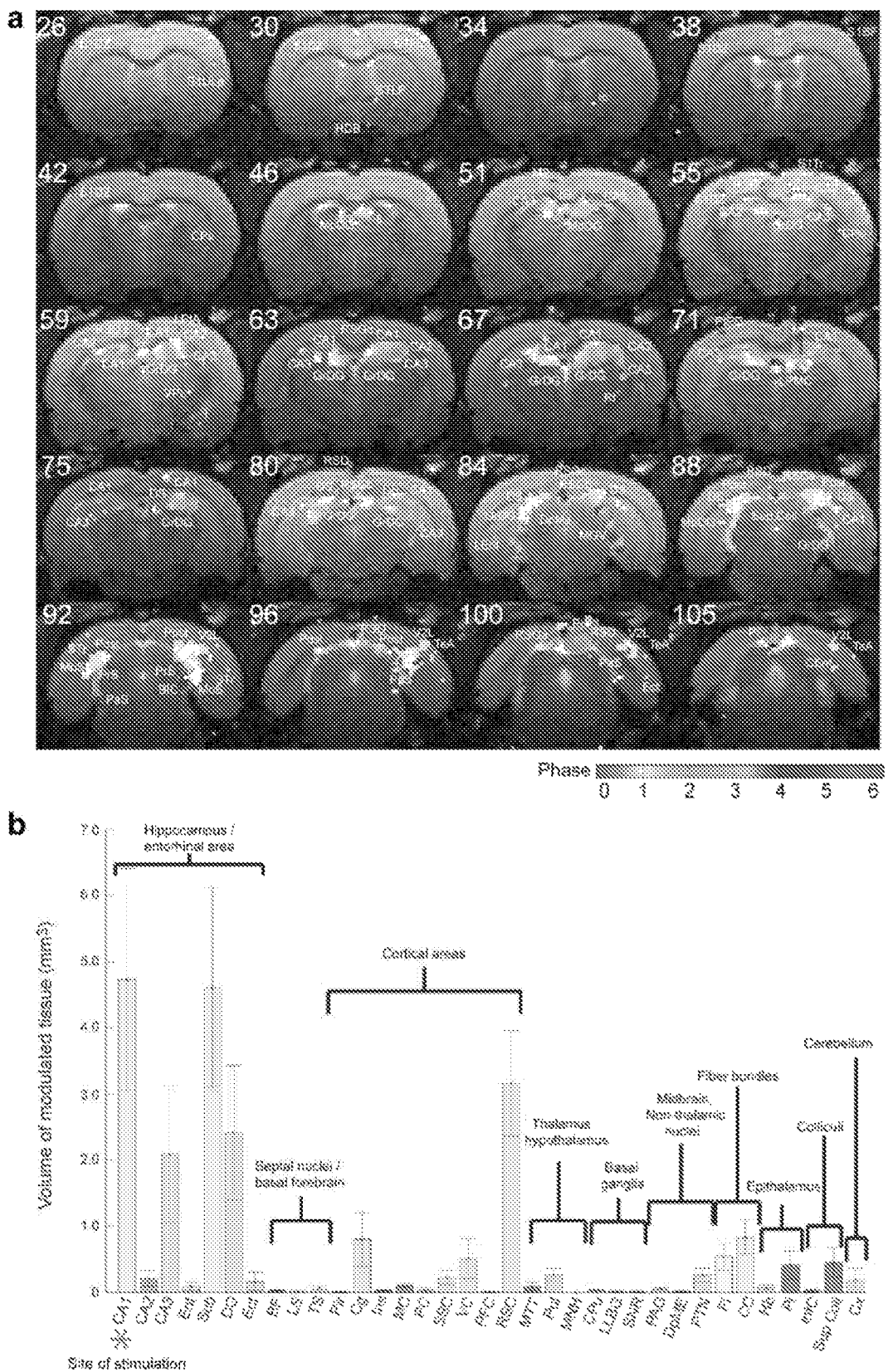
FIG. 28a and FIG. 28b illustrate Seizure Model #1: High frequency stimulation of pyramidal neurons in dorso-medial CA1 evokes seizures with limited neural activity propagation through the hippocampus.
Figure 29:
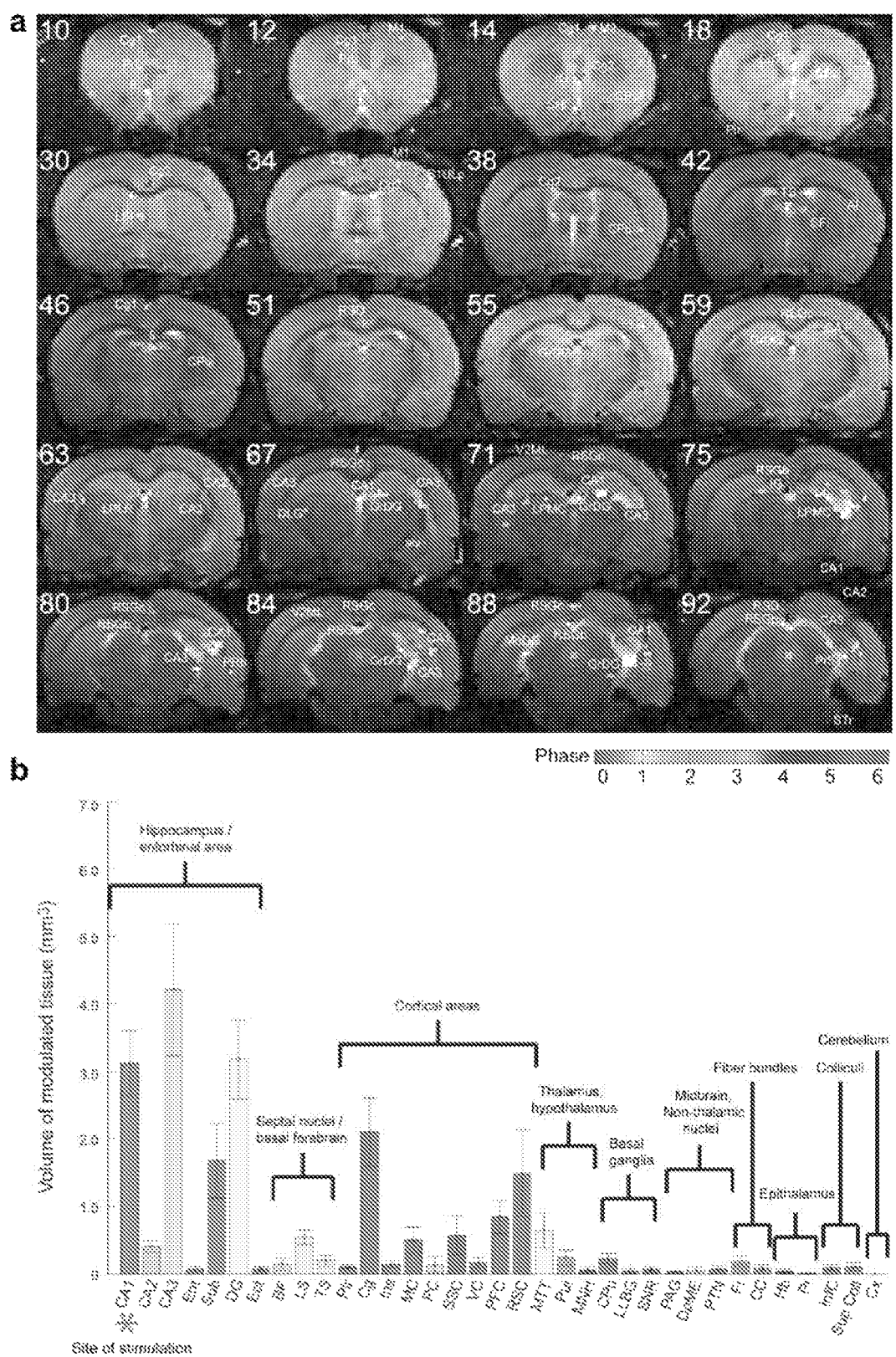
FIG. 29a and FIG. 29b illustrate Seizure Model #2: High frequency stimulation of pyramidal neurons in ventro-lateral CA1 evokes seizures with neural activity propagation through the classical circuit of Papez.
Figure 30:
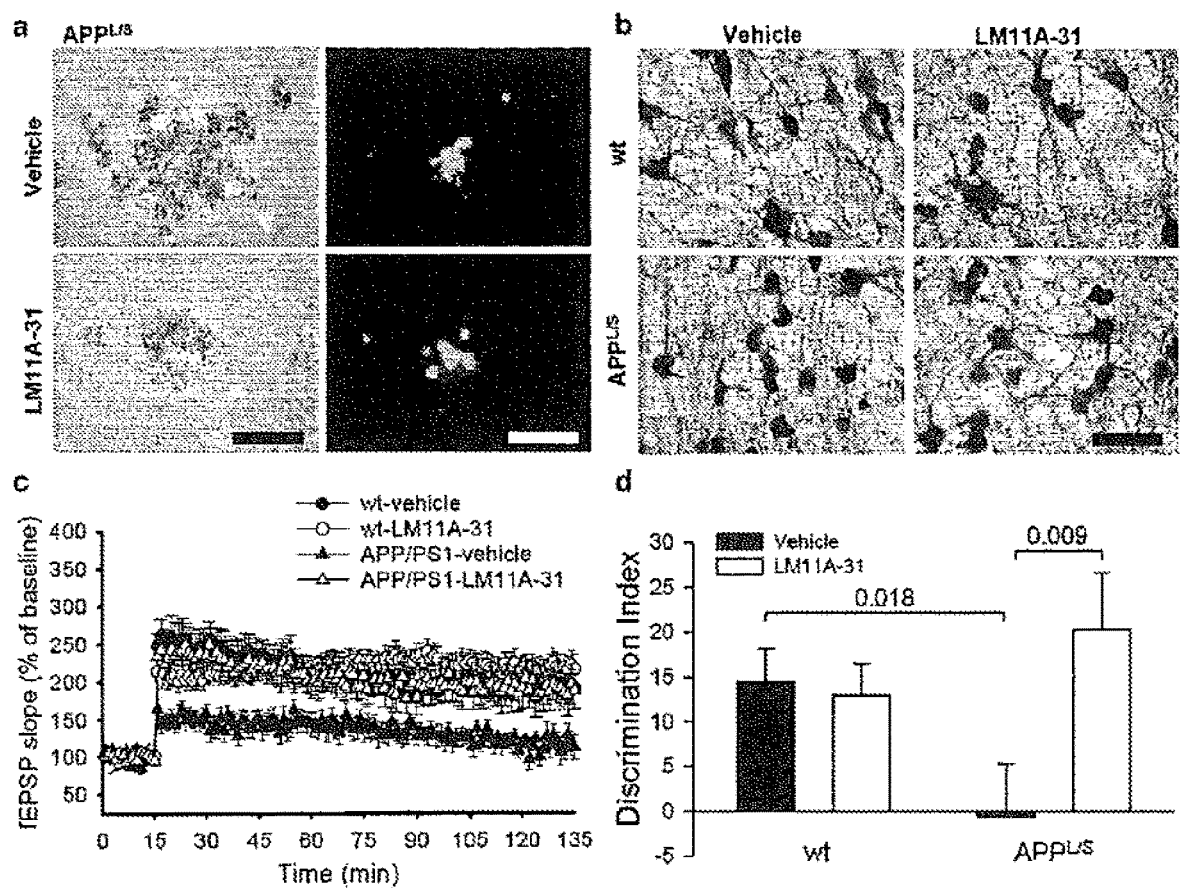
FIG. 30a, FIG. 30b, FIG. 30c, and FIG. 30d illustrate a transgenic mouse model of AD that shows dystrophic neurites and amyloid plaque formation in the hippocampus, reduction of cholinergic neurite length, volume and branching in the basal forebrain, reduction in LTP in the hippocampus, and object recognition deficits, which are all rescued significantly by the administration of a novel drug candidate, LM11A-31.
Figure 31:
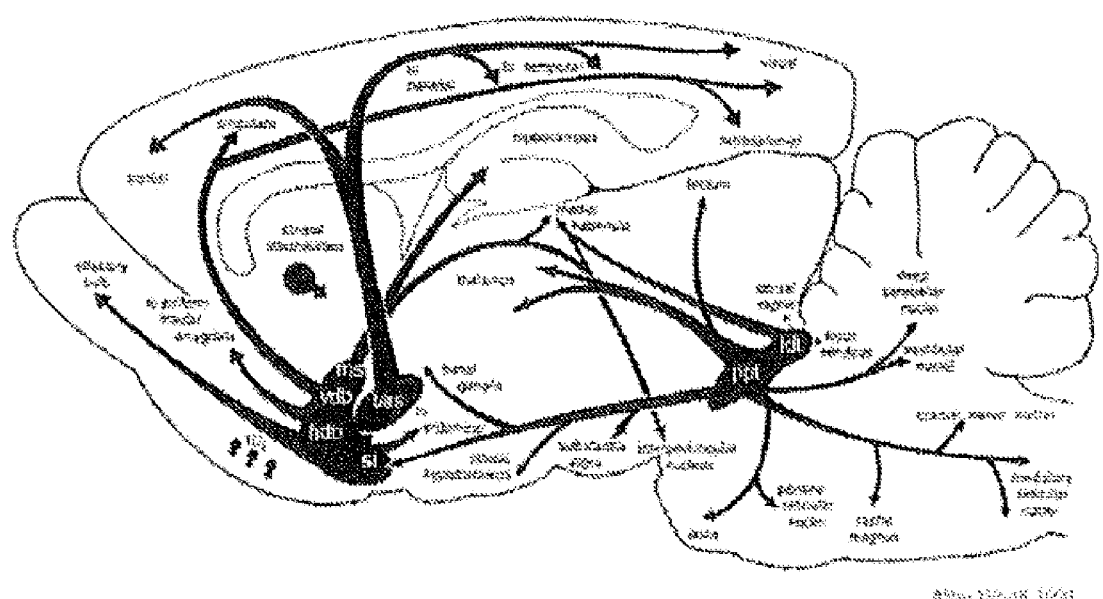
FIG. 31a illustrates a mouse brain cholinergic system. MSDBB in the basal forebrain is known to anatomically project to the hippocampus. In accordance with the present invention, cholinergic neurons were stimulated in MSDBB due to the significant memory loss related to hippocampus in AD.

To this end, the PI's lab have already shown that distinct seizures can be generated with subtle changes in parameters such as the original cell type, location, and temporal firing rate. Optogenetically generated seizure models show repeatable, and precise temporal onset characteristics. Out of several different optogenetically-generated seizures, two will be employed in the proposed study, as shown in FIG. 28, FIG. 29. These will include 40 Hz light stimulation of pyramidal neurons in dorsa-medial CA1 and in ventro-medial CA1 after injecting the AAV virus in the rat (Sprague-Dawley, male, 250-350 g) hippocampus. Dorsa-medial CA1 region in rats is an analog of posterior CA1 in humans and ventro-lateral CA1 region corresponds to anterior CA1. With optogenetics, precise control of temporal firing frequency is possible. OfMRI studies in the PI's lab show that for hippocampal stimulation of pyramidal neurons, higher-grade seizures are generated with longer lasting activity (FIG. 26) and larger area recruitment with higher frequency stimulation above 20 Hz. Therefore, for this first study, two higher frequency stimulation models with anatomical difference in stimulation location were selected. FIG. 27 shows an example of EEG and behavior during a seizure triggered by blue light to the dorsa-medial CA1. Preliminary work has shown different behavioral patterns during seizures corresponding with these models: mainly activity arrest with 40 Hz dorsa-medial stimulation and rearing, falling and wet-dog shakes with 40 Hz stimulation of ventro-lateral hippocampus.

Through ofMRI studies, the seizures can not only be generated with precision but also mapped and defined with accurate knowledge of the brain areas involved and the temporal dynamics. ofMRI hemodynamic response functions (HRFs) (FIG. 26a, b) and the corresponding LFP (FIG. 26c-f) and single unit recordings (FIG. 26g-j) demonstrate the accuracy of the ofMRI technology in providing proper spatio-temporal dynamics. When LFP and single unit recordings were made at locations identified as active regions with ofMRI, neural activity driven by the optogenetic stimulation could be clearly measured. In particular, it shows accurate distinction of short lasting activity generated through low frequency stimulation (FIG. 26a 6-10 Hz traces, c, g) and long lasting activity generated through higher frequency stimulation (FIG. 26a 20-60 Hz traces, b, d-f, h-j). With the ofMRI spatial activity maps and HRF, one can accurately determine the duration and pattern of activity across the whole brain. This level of accuracy has never been observed with regular fMRI. In contrast to the corresponding Racine scale and EEG recordings from which one has to carefully look for subtle differences, which still doesn't necessarily quantitatively define the nature of the seizure, whole brain images depicting all the brain regions involved and the temporal dynamics of the neural activity makes it trivial to quantitatively define the seizures. The two models (FIG. 28, FIG. 29) that will be used for this proposal, clearly depicts the different nature of the two seizures.

Moving the stimulation within CA1 from dorsa-medial to ventro-lateral area shows striking changes in circuit recruitment. Cingulate and prelimbic, infralimbic structures are part of the classical circuit of Papez. Ventro-lateral CA1 stimulation generated seizures propagate through this circuit (FIG. 29) while dorsa-medial seizures do not, and recruits larger, longer lasting activity in areas including CA1, subiculum, and retrosplenial cortex (FIG. 28). Seizures originating from both areas can generate Racine level 5 seizures, but with very different underlying patterns of brain activation. The different activation and propagation patterns could not be identified without ofMRI, except possibly with multiple depth electrode recordings, and those still would entail brain region sampling problems.

The models of dorsa-medial and ventro-lateral optogenetic hippocampal stimulation previously studied may be used and after administration of PHT, lorazepam and LEV, in order to visualize drug efficacy using ofMRI. The efficacy of the drug will first be evaluated by the conventional tests including video and EEG. Then, ofMRI studies will be conducted to visualize details of how the drug impacts the brain network. Drugs will be injected during the ofMRI scans. The goal is to specifically pinpoint the areas of decreased or increased activity involved in the two different seizure models and the three different drugs. We hypothesize that the different nature of the two seizures will reveal different efficacy with the three drugs in terms of which brain area activity is reduced from the drug. The conventional video and EEG tests will be compared with the ofMRI-based results to demonstrate the sensitivity and richness of information ofMRI can provide in terms of the drug efficacy and its mechanism. It will be similar to the difference between seizure classification based on Racine and EEG scales compared to visualizing the whole brain network as in FIG. 28, FIG. 29 to define the seizures. The go/no go decision will be made based on whether we can quantitatively distinguish differences between before and after drug administration for each brain areas. While our ultimate goal is to visualize the distinct impact of each drug on each seizure model, it is possible that the combination of the drugs and models selected for this experiment will show similar effects. However, as long as we can show brain area dependent activity change in any of the 6 cases, it would be sufficient evidence that one can start a systematic search for novel AEDs using ofMRI. The two seizure models in FIG. 28, FIG. 29 were generated with different seizure onset location within CA1. Many other seizures, for example, stimulating small thalamic nuclei with cell type specificity have been developed in the PI's lab. The success of the proposed study in distinguishing drug impact in these models will enable visual inspection of brain activity to define distinct seizure models as well as quantitatively define the drug impact.

Potential Pitfalls and Expectations. We will first administer half of the ED50 for each of PHT, lorazepam and LEV. It is possible that at sufficiently high dose, complete inactivation of all brain areas is observed. In this case, it would be difficult to get more specific information on which brain areas the drug under test impacts. Therefore, we will adjust the dose to half of the initial dose. If any of the drugs display discernible increase/decrease in distinct brain areas, we will consider this a go. If no differences before and after the drug injection can be observed in any of the seizure models or drugs, we will increase AED dosage to the ED50 or a multiple of this dose. If there are still no discernible differences, it will be considered a no go. However, given the level of detail we can detect with ofMRI, and the fact that these drugs are clinically approved drugs which showed efficacy in other animal models, it is highly unlikely that we will get a no go result.

Milestones: OfMRI testing of the 3 drugs will start immediately and finish within the first year, validating the technology's ability to comprehensively evaluate AEDs. We will provide this data, as well as our business development effort generating contracts as our milestone of achievement in the first year. If successful, during the second year, we will start generating revenue by testing novel compounds from pharmaceutical companies. At the end of the second year, we hope to have become a fully functional business entity.

Sample Size and Statistical Analysis Plan.

We will perform repeated testing on the same animals, allowing at least 5 half-lives of each drug to pass (e.g., more than a week) between testing different drugs. We also will evaluate seizure thresholds to rule out a significant "kindling" effect over time. Ability to repeat testing on the same animals will greatly enhance future attractiveness of the model for drug testing. From our experience conducting ofMRI studies, and considering the reliability, the ability to perform sequential experiments in the same animal due to precise repeatability in vivo, non-invasive imaging capabilities, we will need only 5 animals per group. With two models, this will lead to a total of 10 animals, assuming no wastage. Using 10 animals, first the ofMRI of the seizure propagation will be mapped out as in FIG. 28, FIG. 29. In the same animal, drugs will then be administered. Segmenting all the brain regions as shown in FIG. 28, FIG. 29 and looking at the statistical significance of the difference between before and after drug injection, we will analyze how the drugs impact each brain region. Furthermore, the differences in drug efficacy for the two models will be evaluated by how much the overall active volume has changed as well as the specific characteristics regarding which brain region activities change. In summary, two models and three drugs, pre- and post-injection will give 2 datasets on pre-injection for the two models, 6 datasets on post-injection of the three drugs in the two seizure models. The 8 cases. will be compared through statistical comparison of regional data in total of 10 animals. We will also conduct repeated testing of the same experiment condition in the same animal 3 times, adding to the statistical power. This gives a total of 5 animals with 3 repeats, leading to 15 trials per scenario (6 cases) with only 10 animals. We will analyze the data using ANOVA with repeated measure statistics on the continuous variable marking volume of regional activation, in order to evaluate significance of drug treatment versus other important causes of variance. We also will perform Chi Square tests (or proportional difference tests for bin sizes smaller than 5) on the nonparametric measure of regions activated versus non-activated before and after drug administration.

The outcome of this methodology will be a new method for evaluating drugs and doses of potential new AEDs (or devices). We aim to link certain profiles of brain system activations/deactivations to predict efficacy for particular seizure types, and eventually also neurological side effects.

Example E

Neurostimulation methods including deep brain stimulation (DBS), responsive neurostimulation (RNS), vagus nerve stimulation (VNS), are promising new therapies for a wide range of brain disorders, including Parkinson's disease, tremor, depression, obsessive-compulsive disorder, pain, and epilepsy. However, the rudimentary understanding of neurostimulation mechanisms limits its effectiveness. While many therapies approved and under clinical trials demonstrate significant effectiveness, it is unclear what the underlying mechanism of action is. Therefore, currently utilized stimulation parameters and locations involve significant amount of guesswork, resulting in heterogeneous outcome and limited efficacy. While developing a platform to systematically understand neurostimulation mechanisms has paradigm shifting potential, such process has been hindered so far by the extreme complexity of the brain. To parse out the mechanisms, there are major necessary requirements that, until now, could not be satisfied. First, since the brain forms an integrated circuit with even single neurons making connections across large areas of the brain, it is of crucial importance that the data conveys information across the whole brain. Second, in order to obtain the granular details of the temporal dynamics, we need access to individual cell-type specific network elements with high temporal precision. Third, it is crucial to obtain the information in vivo so that the network dynamics can be correlated with behavior.

In this proposal, we aim to put forth our attempts based on key insights and technological developments that were not available before. Using the optogenetic fMRI (ofMRI) technology, combining optogenetic control with high-field fMRI readout, we are able to precisely control brain circuit elements with cell type and temporal precision while visualizing the corresponding response across the whole brain in vivo. Without the need to sacrifice animals to test function, the same individual animals can be tested longitudinally repeatedly, and tracked for functional response in parallel and in series. In this proposal, we aim to develop ofMRI into a platform technology that can enable systematic design of neurostimulation devices. As the original inventor and leader of the ofMRI technology with a unique vision, we have recently made important technological advances. They include the development of high-resolution, distortion-free, awake, high-throughput interactive ofMRI. In addition, as a first step towards understanding neurological disease mechanisms to aid therapeutics development, we have shown that well-defined seizure network pathways with precise origins can be successfully visualized. These initial studies are already giving us key insights into the source of variable efficacy in current clinical trials. The proposed research, upon success, will have a groundbreaking impact in our understanding of the neurological disease mechanisms and the accurate prediction of clinical outcome combined with the ability to systematically design and test neurostimulation strategies will accelerate developments of new therapeutics.

The proposed project takes a radically new approach integrating novel technology from multiple disciplines based on my bold, innovative, grand-scale vision. Due to the daunting nature of this task, it is not a project suitable for traditional hypothesis-driven research funded by NIH R01 or R21 mechanisms. What makes this proposal unique and perfectly suited for the W.M. Keck foundation research programs is that the project is based on my vision identifying the overwhelming need, and that the major achievements I hold to date show great promise in making this project a success.

Example F

An important challenge in drug development for Alzheimer's Disease (AD), as well as many other neurological diseases, is the accurate pre-clinical predictability of the future clinical efficacy and side effects of the compound. The complexity of the neurological system makes it extremely difficult to infer impact of the candidate compound using surrogate in vitro information, ex vivo data, or simple animal behavior models. Our proposal aims to fundamentally transform this process through accurate disease model characterization along with in vivo full brain quantification of the drug administration impact longitudinally over time in the same animals utilizing the optogenetic functional magnetic resonance imaging (ofMRI) technology. ofMRI is a novel technology combining cell type specific, temporally precise stimulation method called optogenetics with fMRI readouts. The first proof of concept study published by the PI (Nature 2010) demonstrated ofMRI technology's ability to accurately visualize brain-wide neural activity resulting from cell types specified by its genetic identity, cell body location, axonal projection target, and temporal signaling patterns.

With further developments in ofMRI technology to achieve high spatial resolution and awake scanning, the PI's lab has preliminary data showing the ability to characterize whole brain network response specifically associated with cholinergic neurons. Selective stimulation of cholinergic neurons in the basal forebrain with defined temporal patterns was shown to elicit widespread neural activity including the hippocampal region. Such direct functional visualization of the network activity with the ability to longitudinally track in vivo can be used to monitor how different doses and course of treatment impacts each individual animal over time with disease progress. This is in contrast with conventional ex vivo technology that relies on sacrificing a large number of animals at different time points, which increases variance, cost, and time while only obtaining surrogate markers of function. In addition, the added ability to evoke responses to specific pathways, rather than isolated passive physiologic recordings, makes the signaling exponentially more robust.

With our preliminary findings showing ofMRI's ability to visualize important network associated with AD with unprecedented precision, we will establish it as a platform for quantitative drug design. With the ability to observe network engagement associated with key neural circuit elements implicated in AD, we will administer a candidate drug that has already shown good electrophysiological, behavioral, and anatomical efficacy. We aim to demonstrate ofMRI-based observation of therapeutic effects. The reversal of AD features could be fully or partially effective and we will be able to directly observe locations of the changes in live animal brains during progress of disease and drug therapy. In addition, side effects will be indicated by increase or decrease in activity as a result of drug administration in areas of the brain unrelated to the disease in question Example G This proposal introduces a technology and associated methodology to provide predictability of the future clinical efficacy and side effects of drug candidates through visualization of the whole-brain dynamic network changes associated with Alzheimer's disease (AD).

Figure 14:
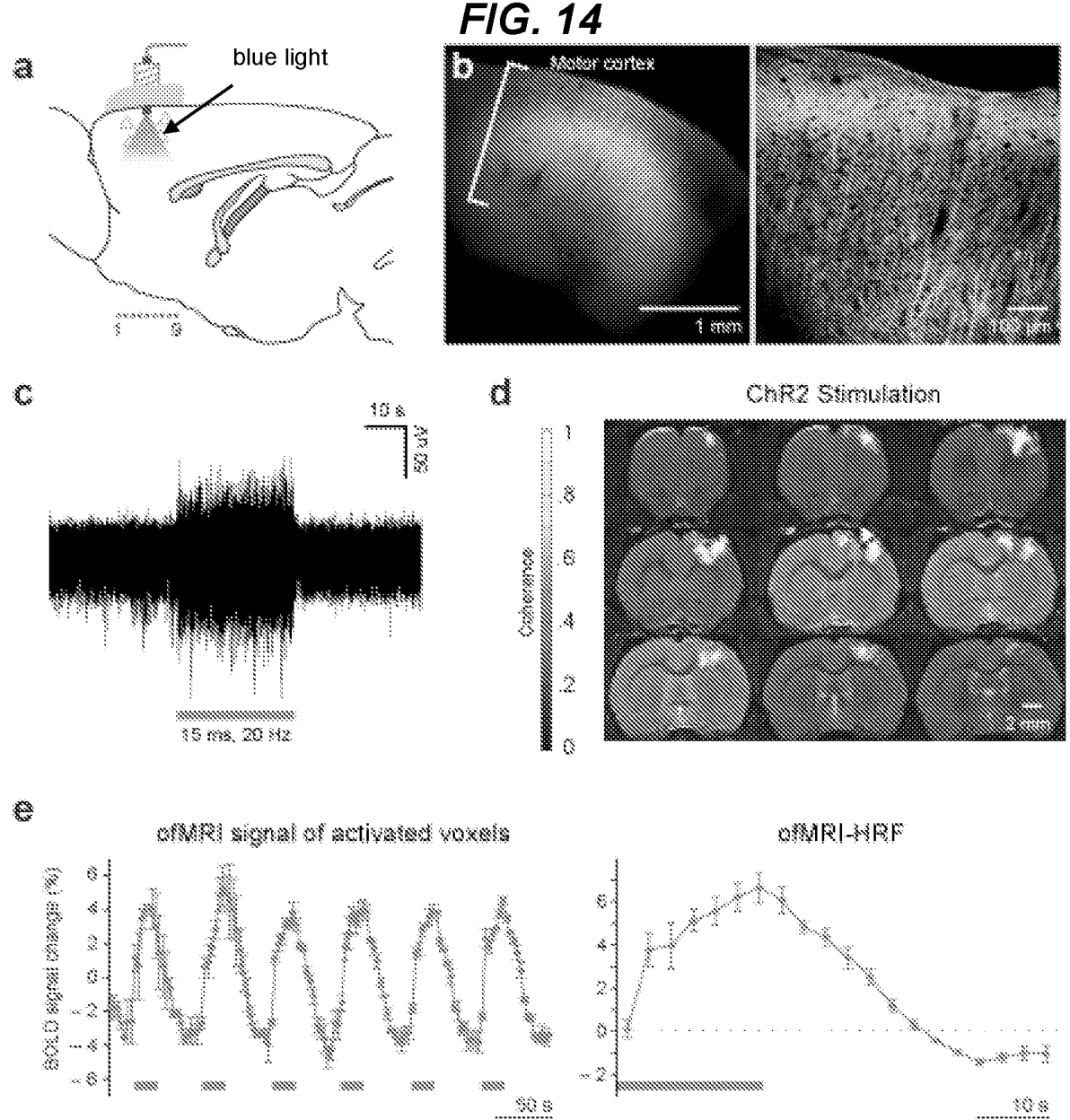

Our approach will utilize a technology that was recently developed by the PI called optogenetic functional magnetic resonance imaging (ofMRI) (FIG. 14). Optogenetics introduces single-component microbial light-activated transmembrane conductance regulators into specific cells using cell type specific promoters to allow millisecond-scale, targeted, activity modulation in vivo. Channelrhodopsin (ChR2), in particular, will trigger neurons expressing ChR2 to be excited with high temporal precision upon exposure to blue light. The ofMRI technology combines optogenetic control with high-field fMRI. In the initial study, it was shown that precise cell type-based fMRI responses could be measured throughout the brain with high temporal precision. We propose to develop ofMRI to enable direct, longitudinal, and systematic evaluation of the network dysfunction associated with AD, which will then be used for quantitative screening and in vivo physiologic feedback for AD drugs.

Various aspects of the present invention aim to:

Aim 1. Evaluate cholinergic neuron's network function in normal mice. Decline of acetylcholine with progressive cholinergic basal forebrain (CBF) neuron degradation is one of the key features of AD (FIG. 30b). So far, these characteristics have been observed and quantified locally in small scale and ex vivo post-mortem studies (FIG. 30b), which makes it difficult to fully understand its functional role and changes with disease in the overall system. Using ofMRI, we will directly visualize the network function associated with cholinergic neurons. We envision that quantitative visualization of the role of cholinergic neurons in the overall brain network in vivo will provide key insights in defining their normal function as well as changes temporal associated with AD in the same mice followed longitudinally. In this aim, we will start by investigating the normal function.

For selective stimulation of cholinergic neurons, two strategies can be used. ChaT-CbR2 transgenic mice with cholinergic neurons selectively expressing ChR2 and Chat-Cre transgenic mice in combination with (DIO) ChR2-EYFP virus. For the ChaT-ChR2 transgenic mice, optical guides need to be surgically implanted to deliver blue light stimulation at the target site. For the Chat-Cre transgenic mice, surgery needs to include viral injection in. order to express ChR2 in cholinergic neurons, in addition to implantation of optical implantation guide. For this aim, we will utilize the ChaT-ChR2 mice that we recently obtained from Dr. Guoping Feng at MIT. However, preliminary studies were conducted using the Chat-Cre mice with Cre dependent AAV virus injection. ChaT-ChR2 mice will enable more stable expression of ChR2 in cholinergic neurons and shorten experiment time since viral expression usually requires approximately 1-month lead-time before experiments.

We will first surgically implant 6 ChaT-CbR2 mice with optical guides targeting the medical septum diagonal band of broca (MSDBB), which is known to project to the hippocampus. This area was chosen for its important anatomical location of having projections to the hippocampal area (FIG. 31), implicated in AD in relations to memory loss. Then, after 3-4 days of recovery from surgery, taking advantage of the non-invasive, in vivo nature of ofMRI, we will scan the mice repeatedly at 3, 6, 9 months from birth. Blue lights will be used to optically stimulate at theta and gamma frequency bands for 20 sec every 1 min. This will be repeated 6 times for statistical significance. Theta and gamma frequencies of stimulations were selected based on altered theta rhythms for AD patients in theta and gamma bands. Immediately prior to the ofMRI experiments, novel object recognition tests will also be conducted as control experiment for aim 2. After ofMRI and behavioral tests are completed, in vivo electrophysiological measurement of local field potential and spiking activity will be performed in ofMRI active regions to confirm the source of the ofMRI signal. Then, the brain will be perfused, photomicrographed for dystrophic neuritis, amyloid plaques, and cholinergic neurites.

Figure 32:
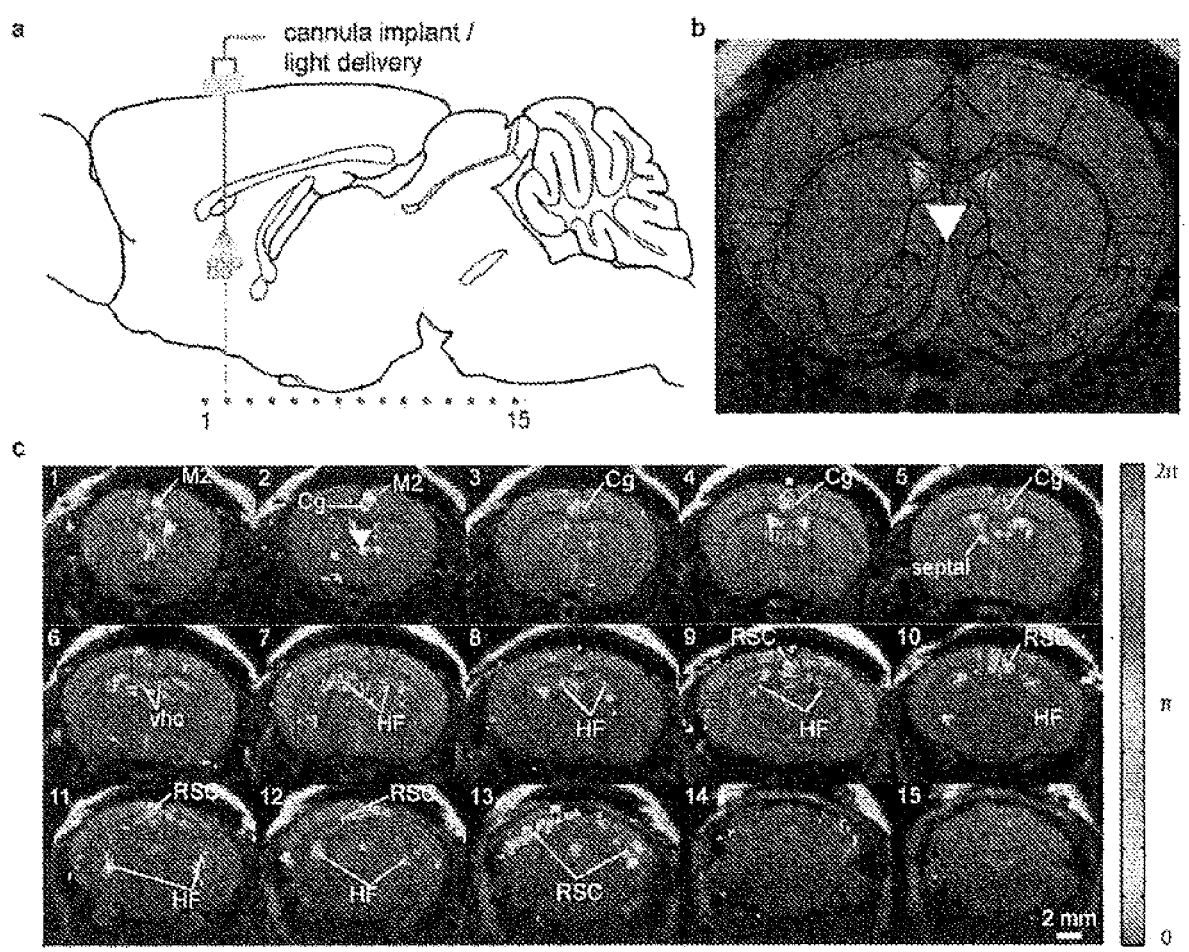
FIG. 32a, FIG. 32b and FIG. 32c illustrate ofMRI with Cholinergic neuron specific stimulation in the basal forebrain reveals global network recruitment including the hippocampus.
Figure 33:
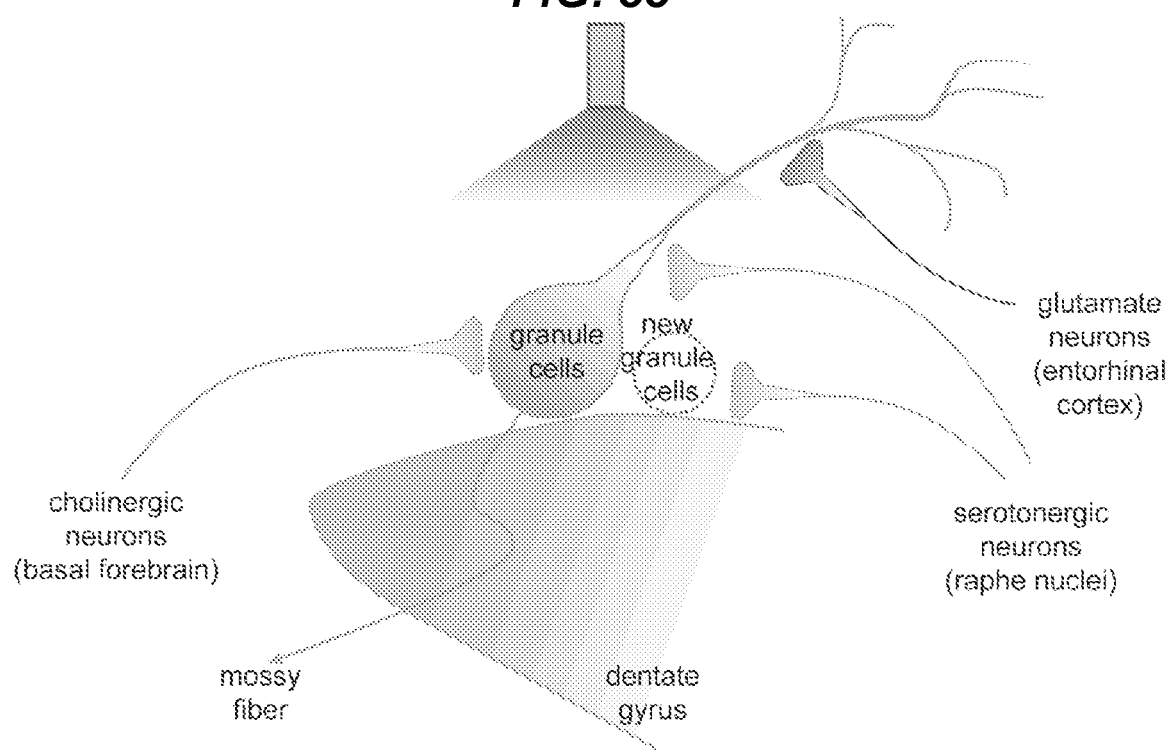
FIG. 33 illustrates inputs to granule cells of the dentate gyms. Granule cell dendrites in the molecular layer receive excitatory input from the entorhinal cortical pyramidal cells. In addition, serotonin input from the raphe and cholinergic input from the basal forebrain nuclei innervate granule cells. Using transgenic animals selectively expressing ChR2 in cholinergic or serotonergic neurons (indicated by green axons) and by placing the optical stimulation fiber in dentate gyms (blue light), cholinergic or serotonergic neurons that specifically project to the dentate gyms will be selectively activated.
Figure 34:
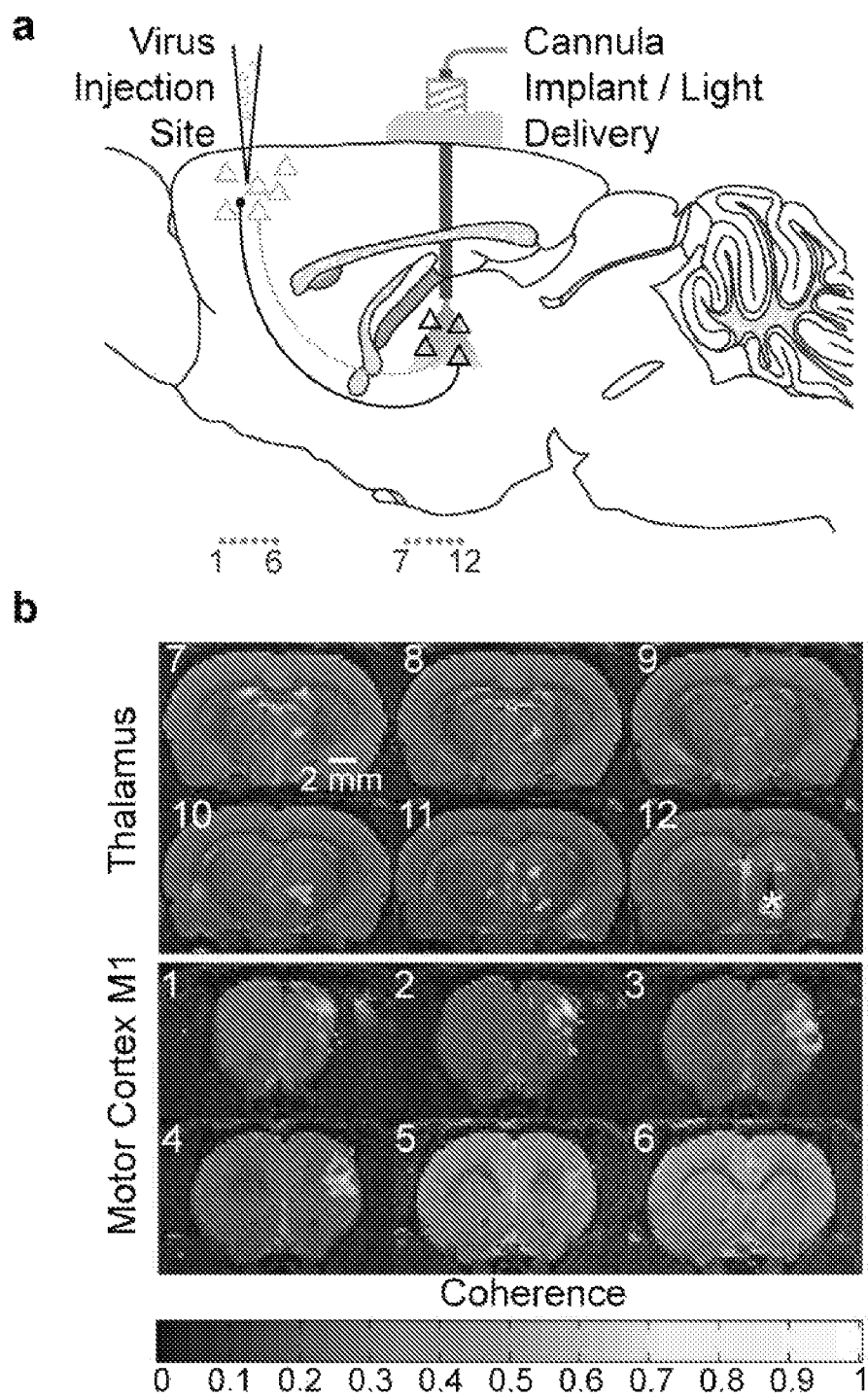
FIG. 34a and FIG. 34b illustrate control of cells defined by location, genetic identity, and wiring during ofMRI.
Figure 35:
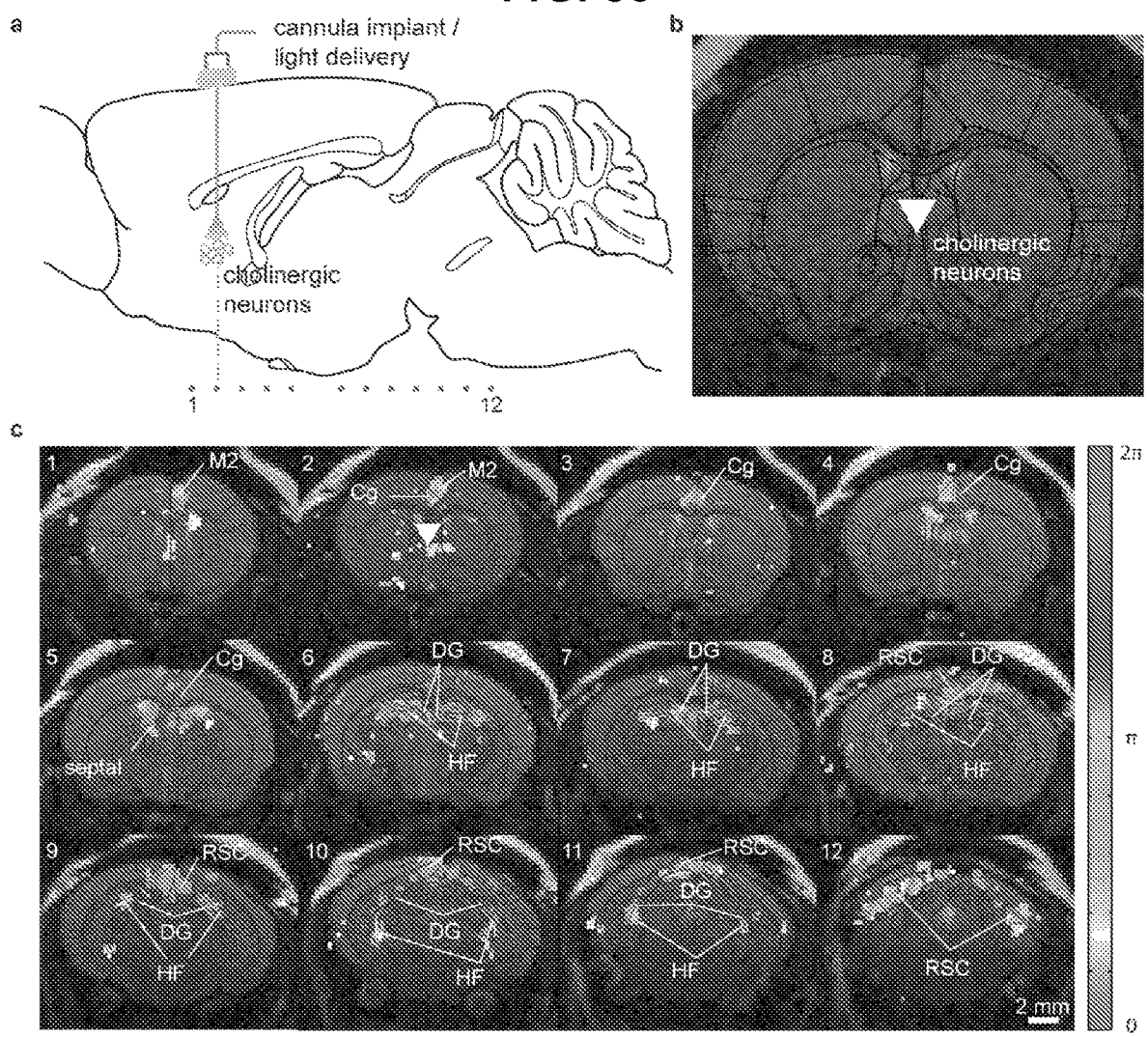
FIG. 35a, FIG. 35b and FIG. 35c illustrate ofMRI with cholinergic neuron specific stimulation in the basal forebrain reveals global network recruitment including the hippocampus.

In our preliminary study using ChaT-Cre mice, cholinergic neurons in MSDBB were targeted using ere-dependent viral injections in addition to optical fiber implantations. With the stimulation of the cholinergic neurons at theta and gamma frequency, we found widespread activity including the hippocampus at the gamma frequency (FIG. 32). In contrast, theta frequency stimulation showed involvement of a much smaller area.

Expected outcome: ofMRI spatial activity map, and hemodynamic response function (HRF) resulting from the selective stimulation of cholinergic neurons at theta and gamma frequencies in MSDBB will reveal key communication partners that are potentially altered in AD. Behavioral experiments are expected to show no signs of memory deficit and we expect to see no abnormality in photomicrographies. We also expect the ofMRI and behavioral data to be largely consistent across 3, 6, 9 months of age, which will only reflect changes due to normal aging which we don't expect to be significant.

Aim 2. Establish ofMRI response to cholinergic stimulation as a bio-marker for AD using transgenic mouse model of AD. A well-characterized mouse model of AD, APPL/S will be used to study the difference in ofMRI response compared to normal mice. APPL/S mice express human amyloid precursor protein (APP) under the Thy1 promoter and are a well-established animal model for AD. This animal model developed in the Masliaha lab was provided to us under an MTA and they will be bred, crossed with the ChaT-ChR2 mice.

We will surgically implant 6 ChaT-ChR2, APPL/S double transgenic mice with optical guides targeting the medical septum diagonal band of broca (MSDBB) as in aim 1. Then, after 3-4 days of recovery from surgery, we will scan the mice repeatedly at 3, 6, 9 months from birth. Stimulation parameters will be matched to the experiments in aim 1. Immediately prior to the ofMRI experiments, novel object recognition tests will be conducted to characterize memory deficits. After ofMRI and behavioral tests are completed, in vivo electrophysiological measurements matching aim 1 will also be conducted. Then, the brain will again be perfused, photomicrographed for dystrophic neuritis, amyloid plaques, and cholinergic neurites.

Expected outcome: ofMRI response resulting from stimulation of cholinergic neurons in MSDBB will be altered in animal model of AD compared to normal mice as measured in aim 1. With ofMRI's proven capability to measure cholinergic, frequency dependent responses (FIG. 32), the progressive functional degeneration will be captured with good sensitivity across different disease state when measured at 3, 6, 9 months of age. Difference will be quantified through statistical tests on the active volume size and peak time of the HRF that reflects timing of resulting neural activity. Novel object recognition tests will show progressive memory deficit that will correlate with ofMRI response changes. Behavioral tests will also be statistically analyzed for differences from normal mice in aim 1 as in FIG. 30d. The photomicrographies will show progressive buildup of dystrophic neuritis, amyloid plaques, and reduction in length, volume, and branching of cholinergic neurites.

Aim 3. Develop ofMRI as a platform to test promising drug candidates. A promising drug candidate for AD, LM11A-31 (FIG. 30) will be used to test ofMRI's capability to predict and evaluate treatment outcome. The p75 neurotrophin receptor (p75NTR) is one of a few specific receptors associated with multiple mechanisms related to AD and modulating its function might constitute an important therapeutic strategy. Previous in vitro studies demonstrated that a small molecule p75NTR ligand, LM11A-31, prevented a number of amyloid-P-induced neurodegenerative mechanisms. Recent studies in the Longo lab also demonstrated the effects of LM11A-31 on neuronal dysfunction and degeneration in the APPL/S transgenic AD mouse model. After oral administration, LM11A-31 was found to cross the blood brain barrier and reach brain concentrations known to provide neuroprotection in vitro. LM11A-31 reversed synaptic impairment in hippocampal slice preparations (FIG. 32c) derived from AD model mice and prevented deficits in novel object recognition (FIG. 32d) and Y-maze performance. Furthermore, LM11A-31 prevented cholinergic neuritic dystrophy in the basal forebrain and hippocampus (FIG. 32a, b), without affecting amyloid levels. These findings indicate that p7SNTR might serve as an important therapeutic target for AD, and that LM11A-31 or its derivatives represent a class of compounds with potential applications in neurodegenerative disease. LM11A-31 was developed in the Longo Lab and will be utilized for this aim to test ofMRI's capability to quantitatively describe drug efficacy by visualizing network function changes.

LM11A-31 will be continuous& administered to 6 ChaT-ChR2, APP s double transgenic mice at 50 mg/kg dose via oral gavages, starting at 2 months of age. Then, we will surgically implant them with the optical guide as in aim 2. After 3-4 days of recovery from surgery, we will scan the mice repeatedly at 3, 6, 9 months from birth. Stimulation parameters will be matched to the experiments in aim 1 and 2. Immediately prior to the of. MRI experiments, novel object recognition tests will be conducted to characterize changes in memory deficits. After ofMRI and behavioral tests are completed, in vivo electrophysiological measurements matching aim 1 will also be conducted. Then, the brain will again be perfused, photomicrographed for dystrophic neuritis, amyloid plaques, and cholinergic neurons and processes.

Expected outcome: Treatment will reverse changes in ofMRI response seen in aim 2 compared to aim 1. Any unintended changes such as activity increase in amygdala, for example, might represent side effects such as anxiety increase. Longitudinal monitoring capability will elucidate the critical therapy time points, and key functional elements related to the behavioral outcome. This will in turn serve as design feedback for further improved drug candidates and timing of dose. Such process will greatly accelerate design and evaluation of AD treatment.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method for modeling brain dynamics in normal and diseased states, the method comprising:
   generating a plurality of distinct seizure types by optogenetic stimulation of neurons at distinct brain regions of one or more first subjects;
   obtaining distinct electroencephalography (EEG) signatures and distinct functional magnetic resonance imaging (fMRI) images for each of the plurality of distinct seizure types;
   generating a plurality of distinct models based on the distinct electroencephalography (EEG) signatures and the distinct functional magnetic resonance imaging (fMRI) images, wherein each of the plurality of distinct models corresponds to a distinct seizure type of the plurality of distinct seizure types, and each of the plurality of distinct models identifies distinct brain networks activated during an onset of the distinct seizure type;
   obtaining a first image of a seizure in a second subject; and identifying a seizure type for the seizure in the second subject based at least in part, on a comparison of the first image to the plurality of distinct models.

2. A method for modeling brain dynamics in normal and diseased states, the method comprising:

optogenetically stimulating pyramidal neurons to generate a seizure in a subject;

monitoring a seizure activity through brain networks of the subject using optogenetic functional magnetic resonance imaging (ofMRI) to map a plurality of seizure activity locations;

measuring local field potentials at the plurality of seizure activity locations to create a diseased state model of the subject's brain; and categorizing the diseased state model to determine an underlying neural activity for the seizure based on the optogenetic stimulation and the optogenetic functional magnetic resonance imaging (ofMRI).

3. The method according to claim 2, further comprising making further measurements of the diseased state model.

4. The method according to claim 3, wherein the further measurements are made using electroencephalography (EEG).

5. The method according to claim 2, wherein the diseased state model is a model of a seizure.

6. The method according to claim 2, wherein the diseased state model is an animal model of a seizure.

7. The method according to claim 6, wherein the seizure is generated by at least one of: dorsal CA1 stimulation, intermediate CA1 stimulation, ventral CA1 stimulation, and subiculum stimulation.

8. The method according to claim 6, further comprising using the animal model of the seizure for neurostimulation and drug design.

9. A system for modeling brain dynamics in normal and diseased states, comprising:

a light-generating component configured for optogenetically stimulating pyramidal neurons to generate a seizure in a subject;

an imaging component configured for monitoring the seizure through linked brain networks with optogenetic functional magnetic resonance imaging (ofMRI) to map a plurality of seizure activity locations; and a measuring component configured for measuring local field potentials at the plurality of seizure activity locations.

10. The system according to claim 9, wherein the light-generating component is configured for optogenetically stimulating pyramidal neurons without incurring direct stimulation of inhibitory interneurons or fibers of passage.

11. The system according to claim 9, wherein the light-generating component is configured for optogenetically stimulating pyramidal neurons utilizing frequency stimulation of below 20 Hz to generate short lasting activity.

12. The system according to claim 11, wherein the light-generating component is configured for optogenetically stimulating pyramidal neurons utilizing frequency stimulation of 6-10 Hz to generate short lasting activity.

13. The system according to claim 9, wherein the light-generating component is configured for optogenetically stimulating pyramidal neurons with frequency stimulation above 20 Hz.

14. The system according to claim 13, wherein the light-generating component is configured for optogenetically stimulating pyramidal neurons utilizing frequency stimulation of 20-60 Hz to generate long lasting activity.

15. The system according to claim 14, wherein the light-generating component is configured for optogenetically stimulating pyramidal neurons with 40 Hz light stimulation.

16. The system according to claim 9, wherein the light-generating component is configured for applying at least one of blue and yellow light to optogenetically stimulate the pyramidal neurons.

17. The system according to claim 16, wherein the light-generating component is configured for delivering blue light in 1, 10, 60, or 100 cycles per second.

18. The system according to claim 17, wherein the light-generating component is configured for delivering blue light in 1, 10, 60, or 100 cycles per second for 20 seconds every minute for a total of six minutes.

* * * * *